US012203092B2

(12) United States Patent
Tripodi et al.

(10) Patent No.: US 12,203,092 B2
(45) Date of Patent: Jan. 21, 2025

(54) SELF-INACTIVATING RABIES VIRUS VECTOR ENCODING A NUCLEOPROTEIN AND DEGRON

(71) Applicant: United Kingdom Research and Innovation, Swindon (GB)

(72) Inventors: Marco Tripodi, Cambridge (GB); Ernesto Ciabatti, Cambridge (GB)

(73) Assignee: Mironid Limited, North Lanark (GB)

( * ) Notice: Subject to any disclaimer, the term of this patent is extended or adjusted under 35 U.S.C. 154(b) by 931 days.

(21) Appl. No.: 16/607,980

(22) PCT Filed: May 2, 2018

(86) PCT No.: PCT/GB2018/051166
§ 371 (c)(1),
(2) Date: Oct. 24, 2019

(87) PCT Pub. No.: WO2018/203049
PCT Pub. Date: Nov. 8, 2018

(65) Prior Publication Data

US 2021/0115472 A1 Apr. 22, 2021

(30) Foreign Application Priority Data

May 2, 2017 (GB) ..................................... 1706945

(51) Int. Cl.
*C12N 15/86* (2006.01)
*C07K 14/145* (2006.01)
*A61K 38/00* (2006.01)

(52) U.S. Cl.
CPC ............ *C12N 15/86* (2013.01); *C07K 14/145* (2013.01); *A61K 38/00* (2013.01); *C07K 2319/50* (2013.01); *C07K 2319/95* (2013.01); *C12N 2760/20143* (2013.01); *C12N 2770/00022* (2013.01); *C12N 2810/609* (2013.01)

(58) Field of Classification Search
CPC ...................... C12N 15/86; C12N 2760/20143
See application file for complete search history.

(56) References Cited

U.S. PATENT DOCUMENTS

2018/0195085 A1 7/2018 Saeki

FOREIGN PATENT DOCUMENTS

| | | | | |
|---|---|---|---|---|
| WO | 2004042352 | A1 | | 5/2004 |
| WO | 2012177499 | A1 | | 12/2012 |
| WO | WO 2016/125364 | A | * | 6/2016 |
| WO | WO 2016/125364 | A1 | * | 8/2016 |
| WO | 2017004022 | A2 | | 1/2017 |
| WO | WO 2017/004022 | A | * | 1/2017 |

OTHER PUBLICATIONS

Luh. L. M., et al., 2020, Prey for the proteasome: Targeted protein degradation-a medicinal chemist's perspective, Angew. Chem. Int. Ed. 59:2-21.*
Timms, R. T., and I. Koren, 2020, Tying up loose ends: the N-degron and C-degron pathways of protein degradation, Biochem. Society Trans. 48:1557-1567.*
Shepherd, J. G., et al., 2023, Emerging Rhabdoviruses and Human Infection, Biology 12:878, pp. 1-12.*
Dietzgen, R. G., et al., 2017, The family Rhabdoviridae: mono- and bipartite negative-sense RNA viruses with diverse genome organization and common evolutionary origins, Vir. Res. 227: 158-170.*
Timms, R. T. and I. Koren, 2020, Tying up loose ends: teh N-degron and C-degron pathways of protein degradation, Biochem. Society Transactions 48:1557-1567.*
Marrero, M. C., and Barrio-Hernandez, I., 2021, Toward Understanding the Biochemical Determinants of Protein Degradation Rates, ACS Omega 6:5091-5100.*
Gray et al., "Activation of Specific Apoptotic Caspases with an Engineered Small-Molecule-Activated Protease", Cell 142(4):637-646, 2010.
Atasoy et al., "A Flex Switch Targets Channelrhodopsin-2 to Multiple Cell Types for Imaging and Long-Range Circuit Mapping," The Journal of Neuroscience 28(28):7025-7030, 2008.
Finke et al., "Replication strategies of rabies virus," Virus Research 111(2):120-131, 2005.
Ciabatti et al., "Life-Long Genetic and Functional Access to Neural Circuits using Self-Inactivating Rabies Virus," Cell, 170(2):382-392, 2017.
International Search Report and Written Opinion issued in PCT/GB2018/051166, dated Jun. 28, 2018, 11 pages.
Search Report issued in GB 1706945.1, dated Feb. 5, 2018, 3 pages.
Benucci et al., "Coding of stimulus sequences by population responses in visual cortex" Nat Neurosci 12(10): 1317-1324 (2009).
Buzsaki et al., "Editorial overview: brain rhythms and dynamic coordination" Current Opinion Neurobiology 31: v-ix, 5 pages (2015).
Callaway, E. "Transneuronal circuit tracing with neurotropic viruses" Current Opinion in Neurobiology 18(6): 617-623 (2008).
Cardona et al., "An integrated micro- and macroarchitectural analysis of the Drosophila brain by computer-assisted serial section electron microscopy" PLoS Biol 8(10): 1-17 (2010).
Emiliani et al. "All-Optical Interrogation of Neural Circuits" J Neurosci 35(41): 13917-13926 (2015).
Komarova et al., "Rabies virus matrix protein interplay with eIF3, new insights into rabies virus pathogenesis" Nucleic Acids Res 35(5): 1522-1532 (2007).
Li et al., "Generation of Destabilized Green Fluorescent Protein as a Transcription Reporter", Journal of Biological Chemistry, 273(52): 34970-34975 (1998).
Livet et al., "Transgenic strategies for combinatorial expression of fluorescent proteins in the nervous system" Nature 450: 56-62 (2007).

(Continued)

*Primary Examiner* — Jeffrey S Parkin
(74) *Attorney, Agent, or Firm* — McNeill PLLC

(57) ABSTRACT

The invention relates to vectors based on a virus from the order Mononegavirales, and in particular a rabies virus. More specifically, it relates to a rabies virus vector which, having transfected a target cell, is switchable between replication-competent and replication-incompetent forms. Amongst other applications, the invention avoids the cytotoxicity associated with current vectors based on rabies virus.

29 Claims, 26 Drawing Sheets

Specification includes a Sequence Listing.

(56) References Cited

OTHER PUBLICATIONS

Luo et al., "Genetic dissection of neural circuits" Neuron 57(5): 634-660 (2008).
Mcintosh et al., "Towards a network theory of cognition" Neural Networks 13: 861-870 (2000).
Mebatsion et al., "Budding of rabies virus particles in the absence of the spike glycoprotein" Cell 84: 941-951 (1996).
Miyamichi et al., "Cortical representations of olfactory input by trans-synaptic tracing" Nature 472(7342): 191-196 (2010).
Winih et al., "Human-level control through deep reinforcement learning" Nature 518:529-533, and Supplementary Information, 13 pages (Feb. 26, 2015).
Namburi et al., "A circuit mechanism for differentiating positive and negative associations" Nature 520(7549):675-678 (2015).
Osakada et al., "Design and generation of rabies virus vectors", Nature Protocols 8(8): 1583-1601 (2013).
Osten et al., "Mapping brain circuitry with a light microscope" Nat Methods 10(6): 1-19 (2013).
Packer et al., "Simultaneous all-optical manipulation and recording of neural circuit activity with cellular resolution in vivo" Nat Methods 12(2): 1-21 (2015).
Packer et al., "Targeting neurons and photons for optogenetics" Nat Neurosci 16(7): 1-28 (2013).
Reardon et al., "Rabies Virus CVS-N2c Strain Enhances Retrograde Synaptic Transfer and Neuronal Viability" Neuron 89(4): 1-29 (2016).
Roselli et al., "A circuit mechanism for neurodegeneration" Cell 151: 250-252 (2012).
Rubinov et al., "Fledgling pathoconnectomics of psychiatric disorders" Trends in cognitive sciences 17(12): 641-647 (2013).
Shockett et al., "Diverse strategies for tetracycline-regulated inducible gene expression" Proceedings of the National Academy of Sciences of the United States of America 93: 5173-5176 (1996).
Silver et al., "Mastering the game of Go with deep neural networks and tree search" Nature 529: 1-37 (2016).
Stepien et al., "Monosynaptic rabies virus reveals premotor network organization and synaptic specificity of cholinergic partition cells" Neuron 68: 456-472 (2010).
Tian et al., "Distributed and Mixed Information in Monosynaptic Inputs to Dopamine Neurons" Neuron 91(5): 1-32 (2016).
Tripodi et al., "Motor antagonism exposed by spatial segregation and timing of neurogenesis" Nature, 479: 61-66 (2011).
Van den Heuvel, "Comparative Connectomics" Trends in cognitive sciences 20(5): 345-361 (2016).
Wertz et al., "Single-cell-initiated monosynaptic tracing reveals layer-specific cortical network modules" Science 349: 70-74 (2015).
Wickersham et al., "Monosynaptic restriction of transsynaptic tracing from single, genetically targeted neurons" Neuron 53(5): 1-16 (2007).
Zhang Huizhan "Expression of Fusion Recombinant Heterologous Protein" Genetic Engineering, 4th Edition, East China University of Science and Technology Press (2017); pp. 111-112 (5 pages).
Partial English translation of Chinese Office Action and Search Report mailed Feb. 23, 2023, in Chinese Application No. 201880029221.8 (12 pages), see reference to Zhang 2017 on p. 5 of the Office Action and p. 1 of the Search Report.
Chinese office action and English translation issued in corresponding application No. 201880029221.8; dated Nov. 23, 2023; 13 pages.
Yu Yuanxun et al., "Ubiquitin Proteasome Signaling Pathway and Nerve Disease," China Molecular Neurology, Anhui Science and Technology Publishing House; pp. 194-197, Aug. 31, 2015.
Zhang Huizhan et al., "Expression of the Fusion Recombinant Heterologous Protein," Genetic Engineering the 4th Edition, East China University of Science and Technology Press; pp. 111-112, Jan. 31, 2017.
Chowdhry et al., "Nrf2 is controlled by two distinct β-TrCP recognition motifs in its Neh6 domain, one of which can be modulated by GSK-3 activity" Oncogene 32(3): pp. 3765-3781 (2013).
Ghoda et al., "Prevention of Rapid Intracellular Degradation of ODC by a Carboxyl-Terminal Truncation" Science vol. 243, pp. 1493-1495 (1989).
Marrero et al., "Sequence-based analysis of protein degradation rates" Proteins, 85:1593-1601 (2017).
Meyer et al., "PEST Motif Serine and Tyrosine Phosphorylation Controls Vascular Endothelial Growth Factor Receptor 2 Stability and Downregulation" Molecular and Cellular Biology 31(10), pp. 2010-2025 (2011).
Spencer et al., "NPDC-1, a Novel Regulator of Neuronal Proliferation, Is Degraded by the Ubiquitin/Proteasome System through a PEST Degradation Motif" The Journal of Biological Chemistry 279(35) pp. 37069-37078 (2004).

* cited by examiner

GACATTGATTATTGACTAGTTATTAATAGTAATCAATTACGGGGTCATTAGTTCATAGCCCATATATGGA
GTTCCGCGTTACATAACTTACGGTAAATGGCCCGCCTGGCTGACCGCCCAACGACCCCCGCCCATTGACG
TCAATAATGACGTATGTTCCCATAGTAACGCCAATAGGGACTTTCCATTGACGTCAATGGGTGGAGTATT
TACGGTAAACTGCCCACTTGGCAGTACATCAAGTGTATCATATGCCAAGTACGCCCCCTATTGACGTCAA
TGACGGTAAATGGCCCGCCTGGCATTATGCCCAGTACATGACCTTATGGGACTTTCCTACTTGGCAGTAC
ATCTACGTATTAGTCATCGCTATTACCATGGTGATGCGGTTTTGGCAGTACATCAATGGGCGTGGATAGC
GGTTTGACTCACGGGGATTTCCAAGTCTCCACCCCATTGACGTCAATGGGAGTTTGTTTTGGCACCAAAA
TCAACGGGACTTTCCAAAATGTCGTAACAACTCCGCCCCATTGACGCAAATGGGCGGTAGGCGTGTACGG
TGGGAGGTCTATATAAGCAGAGCTCTCTGGCTAACTAGAGAACCCACTGCTTACTGGCTTATCGAAATTA
ATACGACTCACTATAGGGAGACCCAAGCTGGCTAGATTAAGCGTCTGATGAGTCCGTGAGGACGAAACCC
GGAGTCCCGGGTCACGCTTAACAACCAGATCAAAGAAAAAACAGACATTGTCAATTGCAAAGCAAAAATG
TAACACCCCTACAATGGATGCCGACAAGATTGTATTCAAAGTCAATAATCAGGTGGTCTCTTTGAAGCCT
GAGATTATCGTGGATCAATATGAGTACAAGTACCCTGCCATCAAAGATTTGAAAAAGCCCTGTATAACCC
TAGGAAAGGCTCCCGATTTAAATAAAGCATACAAGTCAGTTTTGTCAGGCATGAGCGCCGCCAAACTTAA
TCCTGACGATGTATGTTCCTATTTGGCAGCGGCAATGCAGTTTTTTGAGGGGACATGTCCGGAAGACTGG
ACCAGCTATGGAATTGTGATTGCACGAAAAGGAGATAAGATCACCCCAGGTTCTCTGGTGGAGATAAAAC
GTACTGATGTAGAAGGGAATTGGGCTCTGACAGGAGGCATGGAACTGACAAGAGACCCCACTGTCCCTGA
GCATGCGTCCTTAGTCGGTCTTCTCTTGAGTCTGTATAGGTTGAGCAAAATATCCGGGCAAAACACTGGT
AACTATAAGACAAACATTGCAGACAGGATAGAGCAGATTTTTGAGACAGCCCCTTTTGTTAAAATCGTGG
AACACCATACTCTAATGACAACTCACAAAATGTGTGCTAATTGGAGTACTATACCAAACTTCAGATTTTT
GGCCGGAACCTATGACATGTTTTTCTCCCGGATTGAGCATCTATATTCAGCAATCAGAGTGGGCACAGTT
GTCACTGCTTATGAAGACTGTTCAGGACTGGTATCATTTACTGGGTTCATAAAACAAATCAATCTCACCG
CTAGAGAGGCAATACTATATTTCTTCCACAAGAACTTTGAGGAAGAGATAAGAAGAATGTTTGAGCCAGG
GCAGGAGACAGCTGTTCCTCACTCTTATTTCATCCACTTCCGTTCACTAGGCTTGAGTGGGAAATCTCCT
TATTCATCAAATGCTGTTGGTCACGTGTTCAATCTCATTCACTTTGTAGGATGCTATATGGGTCAAGTCA
GATCCCTAAATGCAACGGTTATTGCTGCATGTGCTCCTCATGAAATGTCTGTTCTAGGGGGCTATCTGGG
AGAGGAATTCTTCGGGAAAGGGACATTTGAAAGAAGATTCTTCAGAGATGAGAAAGAACTTCAAGAATAC
GAGGCGGCTGAACTGACAAAGACTGACGTAGCACTGGCAGATGATGGAACTGTCAACTCTGACGACGAGG
ACTACTTTTCAGGTGAAACCAGAAGTCCGGAGGCTGTTTATACTCGAATCATGATGAATGGAGGTCGACT
AAAGAGATCTCACATACGGAGATATGTCTCAGTCAGTTCCAATCATCAAGCCCGTCCAAACTCATTCGCC
GAGTTTCTAAACAAGACATATTCGAGTGACTCAGGTTCCGGAGAGAACCTCTACTTCCAATCGGGATCCG
GTAGCCATGGCTTCCCGCCGGAGGTGGAGGAGCAGGATGATGGCACGCTGCCCATGTCTTGTGCCCAGGA
GAGCGGGATGGACCGTCACCCTGCAGCCTGTGCTTCTGCTAGGATCAATGTGTAAGAAGTTGAATAACAA
AATGCCGGAAATCTACGGATTGTGTATATCCATCATGAAAAAAACTAACACCCCTCCTTTCGAACCATCC
CAAACATGAGCAAGATCTTTGTCAATCCTAGTGCTATTAGAGCCGGTCTGGCCGATCTTGAGATGGCTGA
AGAAACTGTTGATCTGATCAATAGAAATATCGAAGACAATCAGGCTCATCTCCAAGGGGAACCCATAGAG
GTGGACAATCTCCCTGAGGATATGGGGCGACTTCACCTGGATGATGGAAAATCGCCCAACCATGGTGAGA
TAGCCAAGGTGGGAGAAGGCAAGTATCGAGAGGACTTTCAGATGGATGAAGGAGAGGATCCTAGCTTCCT
GTTCCAGTCATACCTGGAAAATGTTGGAGTCCAAATAGTCAGACAAATGAGGTCAGGAGAGAGATTTCTC
AAGATATGGTCACAGACCGTAGAAGAGATTATATCCTATGTCGCGGTCAACTTTCCCAACCCTCCAGGAA
AGTCTTCAGAGGATAAATCAACCCAGACTACTGGCCGAGAGCTCAAGAAGGAGACAACACCCACTCCTTC
TCAGAGAGAAAGCCAATCATCGAAAGCCAGGATGGCGGCTCAAATTGCTTCTGGCCCTCCAGCCCTTGAA
TGGTCGGCTACCAATGAAGAGGATGATCTATCAGTGGAGGCTGAGATCGCTCACCAGATTGCAGAAAGTT
TCTCCAAAAAATATAAGTTTCCCTCTCGATCCTCAGGGATACTCTTGTATAATTTTGAGCAATTGAAAAT
GAACCTTGATGATATAGTTAAAGAGGCAAAAAATGTACCAGGTGTGACCCGTTTAGCCCATGACGGGTCC
AAACTCCCCCTAAGATGTGTACTGGGATGGGTCGCTTTGGCCAACTCTAAGAAATTCCAGTTGTTAGTCG
AATCCGACAAGCTGAGTAAAATCATGCAAGATGACTTGAATCGCTATACATCTTGCTAACCGAACCTCTC
CCCTCAGTCCCTCTAGACAATAAAATCCGAGATGTCCCAAAG (SEQ ID NO: 19)

Fig. 11B

TCAACATGAAAAAAACAGGCAACACCACTGATAAATCGATGAACCTCCTACGTAAGATAGTGAAAAACCG
CAGGGACGAGGACACTCAAAAATCCTCTCCCGCGTCAGCCCCTCTGGATGACGATGACTTGTGGCTTCCA
CCCCCTGAATACGTCCCGCTGAAAGAACTTACAGGCAAGAAGAACATGAGGAACTTTTGTATCAACGGAA
GGGTTAAAGTGTGTAGCCCGAATGGTTACTCGTTCAGGATCCTGCGGCACATTCTGAAATCATTCGACGA
GATATATTCTGGGAATCATAGGATGATCGGGTTAGTCAAAGTGGTTATTGGACTGGCTTTGTCAGGATCT
CCAGTCCCTGAGGGCCTGAACTGGGTATACAAATTGAGGAGAACCTTTATCTTCCAGTGGGCTGATTCCA
GGGGCCCTCTTGAAGGGGAGGAGTTGGAATACTCTCAGGAGATCACTTGGGATGATGATACTGAGTTCGT
CGGATTGCAAATAAGAGTGATTGCAAAACAGTGTCATATCCAGGGCAGAGTCTGGTGTATCAACATGAAC
CCGAGAGCATGTCAACTATGGTCTGACATGTCTCTTCAGACACAAAGGTCCGAAGAGGACAAAGATTCCT
CTCTGCTTCTAGAATAACGTACGTCAGATTATATCCCGCAAATTTATCACTTGTTTACCTCTGGAGGAGA
GAACATATGGGCTCAACTCCAACCCTTGGGAGCAATATAACAAAAAACATGTTATGGTGCCATTAAACCG
CTGCATTTCATCAAAGTCAAGTTGATTACCTTTACATTTTGATCCTCTTGGATGTGAAAAAAACTATTAA
CATCCCTCAAAGGACCTGCAGGTACGCGGCCGCGGTACCGCCACCATGGTGCCCAAGAAGAAGAGGAAAG
TCTCCAACCTGCTGACTGTGCACCAAAACCTGCCTGCCCTCCCTGTGGATGCCACCTCTGATGAAGTCAG
GAAGAACCTGATGGACATGTTCAGGGACAGGCAGGCCTTCTCTGAACACACCTGGAAGATGCTCCTGTCT
GTGTGCAGATCCTGGGCTGCCTGGTGCAAGCTGAACAACAGGAAATGGTTCCCTGCTGAACCTGAGGATG
TGAGGGACTACCTCCTGTACCTGCAAGCCAGAGGCCTGGCTGTGAAGACCATCCAACAGCACCTGGGCCA
GCTCAACATGCTGCACAGGAGATCTGGCCTGCCTCGCCCTTCTGACTCCAATGCTGTGTCCCTGGTGATG
AGGAGAATCAGAAAGGAGAATGTGGATGCTGGGGAGAGAGCCAAGCAGGCCCTGGCCTTTGAACGCACTG
ACTTTGACCAAGTCAGATCCCTGATGGAGAACTCTGACAGATGCCAGGACATCAGGAACCTGGCCTTCCT
GGGCATTGCCTACAACACCCTGCTGCGCATTGCCGAAATTGCCAGAATCAGAGTGAAGGACATCTCCCGC
ACCGATGGTGGGAGAATGCTGATCCACATTGGCAGGACCAAGACCCTGGTGTCCACAGCTGGTGTGGAGA
AGGCCCTGTCCCTGGGGGTTACCAAGCTGGTGGAGAGATGGATCTCTGTGTCTGGTGTGGCTGATGACCC
CAACAACTACCTGTTCTGCCGGGTCAGAAAGAATGGTGTGGCTGCCCCTTCTGCCACCTCCCAACTGTCC
ACCCGGGCCCTGGAAGGGATCTTTGAGGCCACCCACCGCCTGATCTATGGTGCCAAGGATGACTCTGGGC
AGAGATACCTGGCCTGGTCTGGCCACTCTGCCAGAGTGGGTGCTGCCAGGGACATGGCCAGGGCTGGTGT
GTCCATCCCTGAAATCATGCAGGCTGGTGGCTGGACCAATGTGAACATTGTGATGAACTACATCAGAAAC
CTGGACTCTGAGACTGGGGCCATGGTGAGGCTGCTCGAGGATGGGGACGGCAGTGGAGGATCCGGAGCCA
CGAACTTCTCTCTGTTAAAGCAAGCAGGAGACGTGGAAGAAAACCCCGGTCCTACCGGTGTGAGCAAGGG
CGAGGAGGATAACATGGCCATCATCAAGGAGTTCATGCGCTTCAAGGTGCACATGGAGGGCTCCGTGAAC
GGCCACGAGTTCGAGATCGAGGGCGAGGGCGAGGGCCGCCCCTACGAGGGCACCCAGACCGCCAAGCTGA
AGGTGACCAAGGGTGGCCCCCTGCCCTTCGCCTGGGACATCCTGTCCCCTCAGTTCATGTACGGCTCCAA
GGCCTACGTGAAGCACCCCGCCGACATCCCCGACTACTTGAAGCTGTCCTTCCCCGAGGGCTTCAAGTGG
GAGCGCGTGATGAACTTCGAGGACGGCGGCGTGGTGACCGTGACCCAGGACTCCTCCCTGCAGGACGGCG
AGTTCATCTACAAGGTGAAGCTGCGCGGCACCAACTTCCCCTCCGACGGCCCCGTAATGCAGAAGAAGAC
CATGGGCTGGGAGGCCTCCTCCGAGCGGATGTACCCCGAGGACGGCGCCCTGAAGGGCGAGATCAAGCAG
AGGCTGAAGCTGAAGGACGGCGGCCACTACGACGCTGAGGTCAAGACCACCTACAAGGCCAAGAAGCCCG
TGCAGCTGCCCGGCGCCTACAACGTCAACATCAAGTTGGACATCACCTCCCACAACGAGGACTACACCAT
CGTGGAACAGTACGAACGCGCCGAGGGCCGCCACTCCACCGGCGGCATGGACGAGCTGTACAAGGGATAT
CTCAGCCATGGCTTCCCGCCGGAGGTGGAGGAGCAGGATGATGGCACGCTGCCCATGTCTTGTGCCCAGG
AGAGCGGGATGGACCGTCACCCTGCAGCCTGTGCTTCTGCTAGGATCAATGTGTGA

(SEQ ID NO: 19)

Fig. 11B (cont.)

CTCGAGGGCGCGCCTACCCGCGGTAGCTTTTCAGTCGAGAAAAAAACATTAGATCAGAAGAACAACTGGC
AACACTTTCTCAACCTGAGACTTACTTCAAGATGCTCGATCCTGGAGAGGTCTATGATGACCCTATTGAC
CCAATCGAGTTAGAGGCTGAACCCAGAGGAACCCCCATTGTCCCCAACATCTTGAGGAACTCTGACTACA
ATCTCAACTCTCCTTTGATAGAAGATCCTGCTAGACTAATGTTAGAATGGTTAAAAACAGGGAATAGACC
TTATCGGATGACTCTAACAGACAATTGCTCCAGGTCTTTCAGAGTTTTGAAAGATTATTTCAAGAAGGTA
GATTTGGGTTCTCTCAAGGTGGGCGGAATGGCTGCACAGTCAATGATTTCTCTCTGGTTATATGGTGCCC
ACTCTGAATCCAACAGGAGCCGGAGATGTATAACAGACTTGGCCCATTTCTATTCCAAGTCGTCCCCCAT
AGAGAAGCTGTTGAATCTCACGCTAGGAAATAGAGGGCTGAGAATCCCCCCAGAGGGAGTGTTAAGTTGC
CTTGAGAGGGTTGATTATGATAATGCATTTGGAAGGTATCTTGCCAACACGTATTCCTCTTACTTGTTCT
TCCATGTAATCACCTTATACATGAACGCCCTAGACTGGGATGAAGAAAAGACCATCCTAGCATTATGGAA
AGATTTAACCTCAGTGGACATCGGGAAGGACTTGGTAAAGTTCAAAGACCAAATATGGGGACTGCTGATC
GTGACAAAGGACTTTGTTTACTCCCAAAGTTCCAATTGTCTTTTTGACAGAAACTACACACTTATGCTAA
AAGATCTTTTCTTGTCTCGCTTCAACTCCTTAATGGTCTTGCTCTCTCCCCCAGAGCCCCGATACTCAGA
TGACTTGATATCTCAACTATGCCAGCTGTACATTGCTGGGGATCAAGTCTTGTCTATGTGTGGAAACTCC
GGCTATGAAGTCATCAAAATATTGGAGCCATATGTCGTGAATAGTTTAGTCCAGAGAGCAGAAAAGTTTA
GGCCTCTCATTCATTCCTTGGGAGACTTTCCTGTATTTATAAAAGACAAGGTAAGTCAACTTGAAGAGAC
GTTCGGTCCCTGTGCAAGAAGGTTCTTTAGGGCTCTGGATCAATTCGACAACATACATGACTTGGTTTTT
GTGTTTGGCTGTTACAGGCATTGGGGGCACCCATATATAGATTATCGAAAGGGTCTGTCAAAACTATATG
ATCAGGTTCACCTTAAAAAAATGATAGATAAGTCCTACCAGGAGTGCTTAGCAAGCGACCTAGCCAGGAG
GATCCTTAGATGGGGTTTTGATAAGTACTCCAAGTGGTATCTGGATTCAAGATTCCTAGCCCGAGACCAC
CCCTTGACTCCTTATATCAAAACCCAAACATGGCCACCCAAACATATTGTAGACTTGGTGGGGATACAT
GGCACAAGCTCCCGATCACGCAGATCTTTGAGATTCCTGAATCAATGGATCCGTCAGAAATATTGGATGA
CAAATCACATTCTTTCACCAGAACGAGACTAGCTTCTTGGCTGTCAGAAAACCGAGGGGGGCCTGTTCCT
AGCGAAAAAGTTATTATCACGGCCCTGTCTAAGCCGCCTGTCAATCCCCGAGAGTTTCTGAGGTCTATAG
ACCTCGGAGGATTGCCAGATGAAGACTTGATAATTGGCCTCAAGCCAAAGGAACGGGAATTGAAGATTGA
AGGTCGATTCTTTGCTCTAATGTCATGGAATCTAAGATTGTATTTTGTCATCACTGAAAAACTCTTGGCC
AACTACATCTTGCCACTTTTTGACGCGCTGACTATGACAGACAACCTGAACAAGGTGTTTAAAAAGCTGA
TCGACAGGGTCACCGGGCAAGGGCTTTTGGACTATTCAAGGGTCACATATGCATTTCACCTGGACTATGA
AAAGTGGAACAACCATCAAAGATTAGAGTCAACAGAGGATGTATTTTCTGTCCTAGATCAAGTGTTTGGA
TTGAAGAGAGTGTTTTCTAGAACACACGAGTTTTTTCAAAAGGCCTGGATCTATTATTCAGACAGATCAG
ACCTCATCGGGTTACGGGAGGATCAAATATACTGCTTAGATGCGTCCAACGGCCCAACCTGTTGGAATGG
CCAGGATGGCGGGCTAGAAGGCTTACGGCAGAAGGGCTGGAGTCTAGTCAGCTTATTGATGATAGATAGA
GAATCTCAAATCAGGAACACAAGAACCAAAATACTAGCTCAAGGAGACAACCAGGTTTTATGTCCGACAT
ACATGTTGTCGCCAGGGCTATCTCAAGAGGGGCTCCTCTATGAATTGGAGAGAATATCAAGGAATGCACT
TTCGATATACAGAGCCGTCGAGGAAGGGGCATCTAAGCTAGGGCTGATCATCAAGAAAGAAGAGACCATG
TGTAGTTATGACTTCCTCATCTATGGAAAAACCCCTTTGTTTAGAGGTAACATATTGGTGCCTGAGTCCA
AAAGATGGGCCAGAGTCTCTTGCGTCTCTAATGACCAAATAGTCAACCTCGCCAATATAATGTCGACAGT
GTCCACCAATGCGCTAACAGTGGCACAACACTCTCAATCTTTGATCAAACCGATGAGGGATTTTCTGCTC
ATGTCAGTACAGGCAGTCTTTCACTACCTGCTATTTAGCCCAATCTTAAAGGGAAGAGTTTACAAGATTC
TGAGCGCTGAAGGGGAGAGCTTTCTCCTAGCCATGTCAAGGATAATCTATCTAGATCCTTCTTTGGGAGG
GATATCTGGAATGTCCCTCGGAAGATTCCATATACGACAGTTCTCAGACCCTGTCTCTGAAGGGTTATCC
TTCTGGAGAGAGATCTGGTTAAGCTCCCAAGAGTCCTGGATTCACGCGTTGTGTCAAGAGGCTGGAAACC
CAGATCTTGGAGAGAGAACACTCGAGAGCTTCACTCGCCTTCTAGAAGATCCGACCACCTTAAATATCAG
AGGAGGGGCCAGTCCTACCATTCTACTCAAGGATGCAATCAGAAAGGCTTTATATGACGAGGTGGACAAG
GTGGAAAATTCAGAGTTTCGAGAGGCAATCCTGTTGTCCAAGACCCATAGAGATAATTTTATACTCTTCT
TAATATCTGTTGAGCCTCTGTTTCCTCGATTTCTCAGTGAGCTATTCAGTTCGTCTTTTTTGGGAATCCC
CGAGTCAATCATTGGATTGATACAAAACTCCCGAACGATAAGAAGGCAGTTTAGAAAGAGTCTCTCAAAA
ACTTTAGAAGAATCCTTCTACAACTCAGAGATCCACGGGATTAGTCGGATGACCCAGACACCTCAGAGGG
TTGGGGGGTGTGGCCTTGCTCTTCAGAGAGGGCAGATCTACTTAGGGAGATCTCTTGGGGAAGAAAAGT
GGTAGGCACGACAGTTCCTCACCCTTCTGAGATGTTGGGATTACTTCCCAAGTCCTCTATTTCTTGCACT
TGTGGAGCAACAGGAGGAGGCAATCCTAGAGTTTCT (SEQ ID NO: 19)

Fig. 11B (cont.)

GTATCAGTACTCCCGTCCTTTGATCAGTCATTTTTTTCACGAGGCCCCCTAAAGGGATACTTGGGCTCGT
CCACCTCTATGTCGACCCAGCTATTCCATGCATGGGAAAAAGTCACTAATGTTCATGTGGTGAAGAGAGC
TCTATCGTTAAAAGAATCTATAAACTGGTTCATTACTAGAGATTCCAACTTGGCTCAAGCTCTAATTAGG
AACATTATGTCTCTGACAGGCCCTGATTTCCCTCTAGAGGAGGCCCCTGTCTTCAAAAGGACGGGGTCAG
CCTTGCATAGGTTCAAGTCTGCCAGATACAGCGAAGGAGGGTATTCTTCTGTCTGCCCGAACCTCCTCTC
TCATATTTCTGTTAGTACAGACACCATGTCTGATTTGACCCAAGACGGGAAGAACTACGATTTCATGTTC
CAGCCATTGATGCTTTATGCACAGACATGGACATCAGAGCTGGTACAGAGAGACACAAGGCTAAGAGACT
CTACGTTTCATTGGCACCTCCGATGCAACAGGTGTGTGAGACCCATTGACGACGTGACCCTGGAGACCTC
TCAGATCTTCGAGTTTCCGGATGTGTCGAAAAGAATATCCAGAATGGTTTCTGGGGCTGTGCCTCACTTC
CAGAGGCTTCCCGATATCCGTCTGAGACCAGGAGATTTTGAATCTCTAAGCGGTAGAGAAAAGTCTCACC
ATATCGGATCAGCTCAGGGGCTCTTATACTCAATCTTAGTGGCAATTCACGACTCAGGATACAATGATGG
AACCATCTTCCCTGTCAACATATACGGCAAGGTTTCCCCTAGAGACTATTTGAGAGGGCTCGCAAGGGGA
GTATTGATAGGATCCTCGATTTGCTTCTTGACAAGAATGACAAATATCAATATTAATAGACCTCTTGAAT
TGGTCTCAGGGGTAATCTCATATATTCTCCTGAGGCTAGATAACCATCCCTCCTTGTACATAATGCTCAG
AGAACCGTCTCTTAGAGGAGAGATATTTTCTATCCCTCAGAAAATCCCCGCCGCTTATCCAACCACTATG
AAAGAAGGCAACAGATCAATCTTGTGTTATCTCCAACATGTGCTACGCTATGAGCGAGAGATAATCACGG
CGTCTCCAGAGAATGACTGGCTATGGATCTTTTCAGACTTTAGAAGTGCCAAAATGACGTACCTATCCCT
CATTACTTACCAGTCTCATCTTCTACTCCAGAGGGTTGAGAGAAACCTATCTAAGAGTATGAGAGATAAC
CTGCGACAATTGAGTTCTTTGATGAGGCAGGTGCTGGGCGGGCACGGAGAAGATACCTTAGAGTCAGACG
ACAACATTCAACGACTGCTAAAAGACTCTTTACGAAGGACAAGATGGGTGGATCAAGAGGTGCGCCATGC
AGCTAGAACCATGACTGGAGATTACAGCCCCAACAAGAAGGTGTCCCGTAAGGTAGGATGTTCAGAATGG
GTCTGCTCTGCTCAACAGGTTGCAGTCTCTACCTCAGCAAACCCGGCCCCTGTCTCGGAGCTTGACATAA
GGGCCCTCTCTAAGAGGTTCCAGAACCCTTTGATCTCGGGCTTGAGAGTGGTTCAGTGGGCAACCGGTGC
TCATTATAAGCTTAAGCCTATTCTAGATGATCTCAATGTTTTCCCATCTCTCTGCCTTGTAGTTGGGGAC
GGGTCAGGGGGGATATCAAGGGCAGTCCTCAACATGTTTCCAGATGCCAAGCTTGTGTTCAACAGTCTTT
TAGAGGTGAATGACCTGATGGCTTCCGGAACACATCCACTGCCTCCTTCAGCAATCATGAGGGGAGGAAA
TGATATCGTCTCCAGAGTGATAGATCTTGACTCAATCTGGGAAAAACCGTCCGACTTGAGAAACTTGGCA
ACCTGGAAATACTTCCAGTCAGTCCAAAAGCAGGTCAACATGTCCTATGACCTCATTATTTGCGATGCAG
AAGTTACTGACATTGCATCTATCAACCGGATCACCCTGTTAATGTCCGATTTTGCATTGTCTATAGATGG
ACCACTCTATTTGGTCTTCAAAACTTATGGGACTATGCTAGTAAATCCAAACTACAAGGCTATTCAACAC
CTGTCAAGAGCGTTCCCCTCGGTCACAGGGTTTATCACCCAAGTAACTTCGTCTTTTTCATCTGAGCTCT
ACCTCCGATTCTCCAAACGAGGGAAGTTTTTCAGAGATGCTGAGTACTTGACCTCTTCCACCCTTCGAGA
AATGAGCCTTGTGTTATTCAATTGTAGCAGCCCCAAGAGTGAGATGCAGAGAGCTCGTTCCTTGAACTAT
CAGGATCTTGTGAGAGGATTTCCTGAAGAAATCATATCAAATCCTTACAATGAGATGATCATAACTCTGA
TTGACAGTGATGTAGAATCTTTTCTAGTCCACAAGATGGTTGATGATCTTGAGTTACAGAGGGGAACTCT
GTCTAAAGTGGCTATCATTATAGCCATCATGATAGTTTTCTCCAACAGAGTCTTCAACGTTTCCAAACCC
CTAACTGACCCCTCGTTCTATCCACCGTCTGATCCCAAAATCCTGAGGCACTTCAACATATGTTGCAGTA
CTATGATGTATCTATCTACTGCTTTAGGTGACGTCCCTAGCTTCGCAAGACTTCACGACCTGTATAACAG
ACCTATAACTTATTACTTCAGAAAGCAAGTCATTCGAGGGAACGTTTATCTATCTTGGAGTTGGTCCAAC
GACACCTCAGTGTTCAAAAGGGTAGCCTGTAATTCTAGCCTGAGTCTGTCATCTCACTGGATCAGGTTGA
TTTACAAGATAGTGAAGACTACCAGACTCGTTGGCAGCATCAAGGATCTATCCAGAGAAGTGGAAAGACA
CCTTCATAGGTACAACAGGTGGATCACCCTAGAGGATATCAGATCTAGATCATCCCTACTAGACTACAGT
TGCCTGTGAACCGGATACTCCTGGAAGCCTGCCCATGCTAAGACTCTTGTGT (SEQ ID NO: 19)

Fig. 11B (cont.)

GATGTATCTTGAAAAAAACAAGATCACCGGATACTCCTGGAAGCCTGCCCATGCTAAGACTCTTGTGTGA
TGTATCTTGAAAAAAACAAGATCCTAAATCTGAACCTTTGGTTGTTTGATTGTTTTTCTCATTTTTGTTG
TTTATTTGTTAAGCGTGGGTCGGCATGGCATCTCCACCTCCTCGCGGTCCGACCTGGGCATCCGAAGGAG
GACGCACGTCCACTCGGATGGCTAAGGGAGAAGGGCGAATTCCAGCACACTGGCGGCCGTTACTAGTGGA
TCCGAGCTCGGTACCAAGCTTAAGTTTAAACCGCTGATCAGCCTCGACTGTGCCTTCTAGTTGCCAGCCA
TCTGTTGTTTGCCCCTCCCCCGTGCCTTCCTTGACCCTGGAAGGTGCCACTCCCACTGTCCTTTCCTAAT
AAAATGAGGAAATTGCATCGCATTGTCTGAGTAGGTGTCATTCTATTCTGGGGGGTGGGGTGGGGCAGGA
CAGCAAGGGGGAGGATTGGGAAGACAATAGCAGGCATGCTGGGGATGCGGTGGGCTCTATGGCTTCTGAG
GCGGAAAGAACCAGCTGGGGCTCTAGGGGGTATCCCCACGCGCCCTGTAGCGGCGCATTAAGCGCGGCGG
GTGTGGTGGTTACGCGCAGCGTGACCGCTACACTTGCCAGCGCCCTAGCGCCCGCTCCTTTCGCTTTCTT
CCCTTCCTTTCTCGCCACGTTCGCCGGCTTTCCCCGTCAAGCTCTAAATCGGGGGCTCCCTTTAGGGTTC
CGATTTAGTGCTTTACGGCACCTCGACCCCAAAAAACTTGATTAGGGTGATGGTTCACGTAGTGGGCCAT
CGCCCTGATAGACGGTTTTTCGCCCTTTGACGTTGGAGTCCACGTTCTTTAATAGTGGACTCTTGTTCCA
AACTGGAACAACACTCAACCCTATCTCGGTCTATTCTTTTGATTTATAAGGGATTTTGCCGATTTCGGCC
TATTGGTTAAAAAATGAGCTGATTTAACAAAAATTTAACGCGAATTAATTCTGTGGAATGTGTGTCAGTT
AGGGTGTGGAAAGTCCCCAGGCTCCCCAGCAGGCAGAAGTATGCAAAGCATGCATCTCAATTAGTCAGCA
ACCAGGTGTGGAAAGTCCCCAGGCTCCCCAGCAGGCAGAAGTATGCAAAGCATGCATCTCAATTAGTCAG
CAACCATAGTCCCGCCCCTAACTCCGCCCATCCCGCCCCTAACTCCGCCCAGTTCCGCCCATTCTCCGCC
CCATGGCTGACTAATTTTTTTTATTTATGCAGAGGCCGAGGCCGCCTCTGCCTCTGAGCTATTCCAGAAG
TAGTGAGGAGGCTTTTTTGGAGGCCTAGGCTTTTGCAAAAAGCTCCCGGGAGCTTGTATATCCATTTTCG
GATCTGATCAAGAGACAGGATGAGGATCGTTTCGCATGATTGAACAAGATGGATTGCACGCAGGTTCTCC
GGCCGCTTGGGTGGAGAGGCTATTCGGCTATGACTGGGCACAACAGACAATCGGCTGCTCTGATGCCGCC
GTGTTCCGGCTGTCAGCGCAGGGGCGCCCGGTTCTTTTTGTCAAGACCGACCTGTCCGGTGCCCTGAATG
AACTGCAGGACGAGGCAGCGCGGCTATCGTGGCTGGCCACGACGGGCGTTCCTTGCGCAGCTGTGCTCGA
CGTTGTCACTGAAGCGGGAAGGGACTGGCTGCTATTGGGCGAAGTGCCGGGGCAGGATCTCCTGTCATCT
CACCTTGCTCCTGCCGAGAAAGTATCCATCATGGCTGATGCAATGCGGCGGCTGCATACGCTTGATCCGG
CTACCTGCCCATTCGACCACCAAGCGAAACATCGCATCGAGCGAGCACGTACTCGGATGGAAGCCGGTCT
TGTCGATCAGGATGATCTGGACGAAGAGCATCAGGGGCTCGCGCCAGCCGAACTGTTCGCCAGGCTCAAG
GCGCGCATGCCCGACGGCGAGGATCTCGTCGTGACCCATGGCGATGCCTGCTTGCCGAATATCATGGTGG
AAAATGGCCGCTTTTCTGGATTCATCGACTGTGGCCGGCTGGGTGTGGCGGACCGCTATCAGGACATAGC
GTTGGCTACCCGTGATATTGCTGAAGAGCTTGGCGGCGAATGGGCTGACCGCTTCCTCGTGCTTTACGGT
ATCGCCGCTCCCGATTCGCAGCGCATCGCCTTCTATCGCCTTCTTGACGAGTTCTTCTGAGCGGGACTCT
GGGGTTCGAAATGACCGACCAAGCGACGCCCAACCTGCCATCACGAGATTTCGATTCCACCGCCGCCTTC
TATGAAAGGTTGGGCTTCGGAATCGTTTTCCGGGACGCCGGCTGGATGATCCTCCAGCGCGGGGATCTCA
TGCTGGAGTTCTTCGCCCACCCCAACTTGTTTATTGCAGCTTATAATGGTTACAAATAAAGCAATAGCAT
CACAAATTTCACAAATAAAGCATTTTTTTCACTGCATTCTAGTTGTGGTTTGTCCAAACTCATCAATGTA
TCTTATCATGTCTGTATACCGTCGACCTCTAGCTAGAGCTTGGCGTAATCATGGTCATAGCTGTTTCCTG
TGTGAAATTGTTATCCGCTCACAATTCCACACAACATACGAGCCGGAAGCATAAAGTGTAAAGCCTGGGG
TGCCTAATGAGTGAGCTAACTCACATTAATTGCGTTGCGCTCACTGCCCGCTTTCCAGTCGGGAAACCTG
TCGTGCCAGCTGCATTAATGAATCGGCCAACGCGCGGGGAGAGGCGGTTTGCGTATTGGGCGCTCTTCCG
CTTCCTCGCTCACTGACTCGCTGCGCTCGGTCGTTCGGCTGCGGCGAGCGGTATCAGCTCACTCAAAGGC
GGTAATACGGTTATCCACAGAATCAGGGGATAACGCAGGAAAGAACATGTGAGCAAAAGGCCAGCAAAAG
GCCAGGAACCGTAAAAAGGCCGCGTTGCTGGCGTTTTTCCATAGGCTCCGCCCCCCTGACGAGCATCACA
AAAATCGACGCTCAAGTCAGAGGTGGCGAAACCCGACAGGACTATAAAGATACCAGGCGTTTCCCCCTGG
AAGCTCCCTCGTGCGCTCTCCTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGTGTAGGTCGTTCGCTCCAAGC
TGGGCTGTGTGCACGAACCCCCCGTTCAGCCCGACCGCTGCGCCTTATCCGGTAACTATCGTCTTGAGTC
CAACCCGGTAAGACACGACTTATCGCCACTGGCAGCAGCCACTGGTAACAGGATTAGCAGAGCGAGGTAT
GTAGGCGGTGCTACAGAGTTCTTGAAGTGGTGGCCTAACTACGGCTACACTAGAAGAACAGTATTTGGTA
TCTGCGCTCTGCTGAAGCCAGTTACCTTCGGAAAAAGAGTTGGTAGCTCTTGATCCGGCAAACAAACCAC
CGCTGGTAGCGGTGGTTTTTTTGTTTGCAAGCAGCA

(SEQ ID NO: 19)

Fig. 11B (cont.)

GATTACGCGCAGAAAAAAAGGATCTCAAGAAGATCCTTTGATCTTTTCTACGGGGTCTGACGCTCAGTGG
AACGAAAACTCACGTTAAGGGATTTTGGTCATGAGATTATCAAAAAGGATCTTCACCTAGATCCTTTTAA
ATTAAAAATGAAGTTTTAAATCAATCTAAAGTATATATGAGTAAACTTGGTCTGACAGTTACCAATGCTT
AATCAGTGAGGCACCTATCTCAGCGATCTGTCTATTTCGTTCATCCATAGTTGCCTGACTCCCCGTCGTG
TAGATAACTACGATACGGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCAGAAGTGGTCCTGCAAC
TTTATCCGCCTCCATCCAGTCTATTAATTGTTGCCGGGAAGCTAGAGTAAGTAGTTCGCCAGTTAATAGT
TTGCGCAACGTTGTTGCCATTGCTACAGGCATCGTGGTGTCACGCTCGTCGTTTGGTATGGCTTCATTCA
GCTCCGGTTCCCAACGATCAAGGCGAGTTACATGATCCCCCATGTTGTGCAAAAAAGCGGTTAGCTCCTT
CGGTCCTCCGATCGTTGTCAGAAGTAAGTTGGCCGCAGTGTTATCACTCATGGTTATGGCAGCACTGCAT
AATTCTCTTACTGTCATGCCATCCGTAAGATGCTTTTCTGTGACTGGTGAGTACTCAACCAAGTCATTCT
GAGAATAGTGTATGCGGCGACCGAGTTGCTCTTGCCCGGCGTCAATACGGGATAATACCGCGCCACATAG
CAGAACTTTAAAAGTGCTCATCATTGGAAAACGTTCTTCGGGGCGAAAACTCTCAAGGATCTTACCGCTG
TTGAGATCCAGTTCGATGTAACCCACTCGTGCACCCAACTGATCTTCAGCATCTTTTACTTTCACCAGCG
TTTCTGGGTGAGCAAAAACAGGAAGGCAAAATGCCGCAAAAAAGGGAATAAGGGCGACACGGAAATGTTG
AATACTCATACTCTTCCTTTTTCAATATTATTGAAGCATTTATCAGGGTTATTGTCTCATGAGCGGATAC
ATATTTGAATGTATTTAGAAAAATAAACAAATAGGGGTTCCGCGCACATTTCCCCGAAAAGTGCCACCTG
ACGTCGACGGATCGGGAGATCTCCCGATCCCCTATGGTGCACTCTCAGTACAATCTGCTCTGATGCCGCA
TAGTTAAGCCAGTATCTGCTCCCTGCTTGTGTGTTGGAGGTCGCTGAGTAGTGCGCGAGCAAAATTTAAG
CTACAACAAGGCAAGGCTTGACCGACAATTGCATGAAGAATCTGCTTAGGGTTAGGCGTTTTGCGCTGCT
TCGCGATGTACGGGCCAGATATACGCGT (SEQ ID NO: 19)

Fig. 11B (cont.)

GACGGATCGGGAGATCTCCCGATCCCCTATGGTGCACTCTCAGTACAATCTGCTCTGATGCCGCATAGTT
AAGCCAGTATCTGCTCCCTGCTTGTGTGTTGGAGGTCGCTGAGTAGTGCGCGAGCAAAATTTAAGCTACA
ACAAGGCAAGGCTTGACCGACAATTGCATGAAGAATCTGCTTAGGGTTAGGCGTTTTGCGCTGCTTCGCG
ATGTACGGGCCAGATATACGCGTTGACATTGATTATTGACTAGTTATTAATAGTAATCAATTACGGGGTC
ATTAGTTCATAGCCCATATATGGAGTTCCGCGTTACATAACTTACGGTAAATGGCCCGCCTGGCTGACCG
CCCAACGACCCCCGCCCATTGACGTCAATAATGACGTATGTTCCCATAGTAACGCCAATAGGGACTTTCC
ATTGACGTCAATGGGTGGAGTATTTACGGTAAACTGCCCACTTGGCAGTACATCAAGTGTATCATATGCC
AAGTACGCCCCCTATTGACGTCAATGACGGTAAATGGCCCGCCTGGCATTATGCCCAGTACATGACCTTA
TGGGACTTTCCTACTTGGCAGTACATCTACGTATTAGTCATCGCTATTACCATGGTGATGCGGTTTTGGC
AGTACATCAATGGGCGTGGATAGCGGTTTGACTCACGGGGATTTCCAAGTCTCCACCCCATTGACGTCAA
TGGGAGTTTGTTTTGGCACCAAAATCAACGGGACTTTCCAAAATGTCGTAACAACTCCGCCCCATTGACG
CAAATGGGCGGTAGGCGTGTACGGTGGGAGGTCTATATAAGCAGAGCTCTCTGGCTAACTAGAGAACCCA
CTGCTTACTGGCTTATCGAAATTAATACGACTCACTATAGGGAGACCCAAGCTGGCTAGATTAAGCGTCT
GATGAGTCCGTGAGGACGAAACCCGGAGTCCCGGGTCacgcttaacaaccagatcaaagaaaaaacagac
attgtcaattgcaaagcaaaaatgtaacacccctacaatggatgccgacaagattgtattcaaagtcaat
aatcaggtggtctctttgaagcctgagattatcgtggatcaatatgagtacaagtaccctgccatcaaag
atttgaaaaagccctgtataaccctaggaaaggctcccgatttaaataaagcatacaagtcagttttgtc
aggcatgagcgccgccaaacttaatcctgacgatgtatgttcctatttggcagcggcaatgcagtttttt
gaggggacatgtccggaagactggaccagctatggaattgtgattgcacgaaaaggagataagatcaccc
caggttctctggtggagataaaacgtactgatgtagaagggaattgggctctgacaggaggcatggaact
gacaagagaccccactgtccctgagcatgcgtccttagtcggtcttctcttgagtctgtataggttgagc
aaaatatccgggcaaaacactggtaactataagacaaacattgcagacaggatagagcagattttgaga
cagcccctttgttaaaatcgtggaacaccatactctaatgacaactcacaaaatgtgtgctaattggag
tactataccaaacttcagattttggccggaacctatgacatgtttttctcccggattgagcatctatat
tcagcaatcagagtgggcacagttgtcactgcttatgaagactgttcaggactggtatcatttactgggt
tcataaaacaaatcaatctcaccgctagagaggcaatactatatttcttccacaagaactttgaggaaga
gataagaagaatgtttgagccagggcaggagacagctgttcctcactcttatttcatccacttccgttca
ctaggcttgagtgggaaatctccttattcatcaaatgctgttggtcacgtgttcaatctcattcacttg
taggatgctatatgggtcaagtcagatccctaaatgcaacggttattgctgcatgtgctcctcatgaaat
gtctgttctaggggggctatctgggagaggaattcttcgggaaagggacatttgaaagaagattcttcaga
gatgagaaagaacttcaagaatacgaggcggctgaactgacaaagactgacgtagcactggcagatgatg
gaactgtcaactctgacgacgaggactacttttcaggtgaaaccagaagtccggaggctgtttatactcg
aatcatgatgaatggaggtcgactaaagagatctcacatacggagatatgtctcagtcagttccaatcat
caagcccgtccaaactcattcgccgagtttctaaacaagacatattcgagtgactca*GGTTCCGGA*gaga
acctctacttccaatcgGGATCCGGTAGCCATGGCTTCCCGCCGGAGGTGGAGGAGCAGGATGATGGCAC
GCTGCCCATGTCTTGTGCCCAGGAGAGCGGGATGGACCGTCACCCTGCAGCCTGTGCTTCTGCTAGGATC
AATGTGtaagaagttgaataacaaaatgccggaaatctacggattgtgtatatccatcatgaaaaaact
aacacccctcctttcgaaccatcccaaacatgagcaagatctttgtcaatcctagtgctattagagccgg
tctggccgatcttgagatggctgaagaaactgttgatctgatcaatagaaatatcgaagacaatcaggct
catctccaaggggaacccatagaggtggacaatctccctgaggatatggggcgacttcacctggatgatg
gaaaatcgcccaaccatggtgagatagccaaggtgggagaaggcaagtatcgagaggactttcagatgga
tgaaggagaggatcctagcttcctgttccagtcatacctggaaaatgttggagtccaaatagtcagacaa
atgaggtcaggagagagatttctcaagatatggtcacagaccgtagaagagattatatcctatgtcgcgg
tcaactttcccaaccctccaggaaagtcttcagaggataaatcaacccagactactggccgagagctcaa
gaaggagacaacacccactccttctcagagagaaagccaatcatcgaaagccaggatggcggctcaaatt
gcttctggccctccagcccttgaatggtcggctaccaatgaagaggatgatctatcagtggaggctgaga
tcgctcaccagattgcagaaagtttctccaaaaaatataagtttccctctcgatcctcaggatactctt
gtataatttgagcaattgaaaatgaaccttgatgatatagttaaagaggcaaaaaatgtaccaggtgtg
acccgtttagcccatgacgggtccaaactcccccctaagatgtgtactgggatgggtcgctttggccaact
ctaagaaattccagttgttagtcgaatccgacaag

(SEQ ID NO: 20)

Fig. 13 ctgagtaaaatcatgcaagatgacttgaatcgctatacatcttgctaaccgaacctctcccctcagtccc
tctagacaataaaatccgagatgtcccaaagtcaacatgaaaaaaacaggcaacaccactgataaaTCGa
tgaacctcctacgtaagatagtgaaaaaccgcagggacgaggacactcaaaaatcctctcccgcgtcagc
ccctctggatgacgatgacttgtggcttccacccccctgaatacgtcccgctgaaagaacttacaggcaag
aagaacatgaggaactttgtatcaacggaagggttaaagtgtgtagcccgaatggttactcgttcagga
tcctgcggcacattctgaaatcattcgacgagatatattctggaatcataggatgatcgggttagtcaa
agtggttattggactggctttgtcaggatctccagtccctgagggcctgaactgggtatacaaattgagg
agaacctttatcttccagtgggctgattccagggggccctcttgaaggggaggagttggaatactctcagg
agatcacttgggatgatgatactgagttcgtcggattgcaaataagagtgattgcaaaacagtgtcatat
ccagggcagagtctggtgtatcaacatgaacccgagagcatgtcaactatggtctgacatgtctcttcag
acacaaaggtccgaagaggacaaagattcctctctgcttctagaataacgtacgtcagattatatcccgc
aaatttatcacttgtttacctctggaggagagaacatatgggctcaactccaacccttgggagcaatata
acaaaaaacatgttatggtgccattaaaccgctgcatttcatcaaagtcaagttgattacctttacattt
tgatcctcttggatgtgaaaaaaactattaacatccctcaaagga*CCTGCAGGTACGCGGCCGCTACGCC*
*CGGGCTACGCTAGC*atgaaaaaaactaacacccctcc*TTAATTAATACGGCGCGCC*taccccgcggtagct
tttcagtcgagaaaaaaacattagatcagaagaacaactggcaacactttctcaacctgagacttacttc
aagatgctcgatcctggagaggtctatgatgaccctattgacccaatcgagttagaggctgaacccagag
gaacccccattgtccccaacatcttgaggaactctgactacaatctcaactctcctttgatagaagatcc
tgctagactaatgttagaatggttaaaaacagggaatagaccttatcggatgactctaacagacaattgc
tccaggtctttcagagttttgaaagattatttcaagaaggtagatttgggttctctcaaggtgggcggaa
tggctgcacagtcaatgatttctctctggttatatggtgcccactctgaatccaacaggagccggagatg
tataacagacttggcccatttctattccaagtcgtcccccatagagaagctgttgaatctcacgctagga
aatagagggctgagaatcccccagagggagtgttaagttgccttgagagggttgattatgataatgcat
ttggaaggtatcttgccaacacgtattcctcttacttgttcttccatgtaatcaccttatacatgaacgc
cctagactgggatgaagaaaagaccatcctagcattatggaaagatttaacctcagtggacatcgggaag
gacttggtaaagttcaaagaccaaatatggggactgctgatcgtgacaaaggactttgtttactcccaaa
gttccaattgtctttttgacagaaactacacacttatgctaaaagatcttttcttgtctcgcttcaactc
cttaatggtcttgctctctcccccagagccccgatactcagatgacttgatatctcaactatgccagctg
tacattgctggggatcaagtcttgtctatgtgtggaaactccggctatgaagtcatcaaaatattggagc
catatgtcgtgaatagtttagtccagagagcagaaaagtttaggcctctcattcattccttgggagactt
tcctgtatttataaaagacaaggtaagtcaacttgaagagacgttcggtccctgtgcaagaaggttcttt
agggctctggatcaattcgacaacatacatgacttggtttttgtgtttggctgttacaggcattggggc
acccatatatagattatcgaaagggtctgtcaaaactatatgatcaggttcaccttaaaaaatgataga
taagtcctaccaggagtgcttagcaagcgacctagccaggaggatccttagatggggttttgataagtac
tccaagtggtatctggattcaagattcctagcccgagaccaccccttgactccttatatcaaaacccaaa
catggccacccaaacatattgtagacttggtgggggatacatggcacaagctcccgatcacgcagatctt
tgagattcctgaatcaatggatccgtcagaaatattggatgacaaatcacattctttcaccagaacgaga
ctagcttcttggctgtcagaaaaccgagggggcctgttcctagcgaaaaagttattatcacggccctgt
ctaagccgcctgtcaatccccgagagtttctgaggtctatagacctcggaggattgccagatgaagactt
gataattggcctcaagccaaaggaacgggaattgaagattgaaggtcgattctttgctctaatgtcatgg
aatctaagattgtattttgtcatcactgaaaaactcttggccaactacatcttgccactttttgacgcgc
tgactatgacagacaacctgaacaaggtgtttaaaaagctgatcgacagggtcaccgggcaagggctttt
ggactattcaagggtcacatatgcatttcacctggactatgaaaagtggaacaaccatcaaagattagag
tcaacagaggatgtattttctgtcctagatcaagtgtttggattgaagagagtgttttctagaacacacg
agtttttcaaaaggcctggatctattattcagacagatcagacctcatcgggttacgggaggatcaaat
atactgcttagatgcgtccaacggcccaacctgttggaatggccaggatggcgggctagaaggcttacgg
cagaagggctggagtctagtcagcttattgatgatagatagagaatctcaaatcaggaacacaagaacca
aaatactagctcaaggagacaaccaggttttatgtccgacatacatgttgtcgccagggctatctcaaga
ggggctcctctatgaattggagagaatatcaaggaatgcactttcgatatacagagccgtcgaggaaggg
gcatctaagctagggctgatcatcaagaaagaagagaccatgtgtagttatgacttcctcatctatggaa
aaacccctttgtttagaggtaacatattggtgcctgagtccaaaagatgggccagagtctcttgcgtctc

(SEQ ID NO: 20)

Fig. 13 (cont.)

taatgaccaaatagtcaacctcgccaatataatgtcgacagtgtccaccaatgcgctaacagtggcacaa
cactctcaatctttgatcaaaccgatgagggatttctgctcatgtcagtacaggcagtctttcactacc
tgctatttagcccaatcttaaagggaagagtttacaagattctgagcgctgaaggggagagctttctcct
agccatgtcaaggataatctatctagatccttctttgggagggatatctggaatgtccctcggaagattc
catatacgacagttctcagaccctgtctctgaagggttatccttctggagagagatctggttaagctccc
aagagtcctggattcacgcgttgtgtcaagaggctggaaacccagatcttggagagagaacactcgagag
cttcactcgccttctagaagatccgaccaccttaaatatcagaggaggggccagtcctaccattctactc
aaggatgcaatcagaaaggctttatatgacgaggtggacaaggtggaaaattcagagtttcgagaggcaa
tcctgttgtccaagacccatagagataatttatactcttcttaatatctgttgagcctctgtttcctcg
atttctcagtgagctattcagttcgtctttttgggaatccccgagtcaatcattggattgatacaaaac
tcccgaacgataagaaggcagtttagaaagagtctctcaaaaactttagaagaatccttctacaactcag
agatccacgggattagtcggatgacccagacacctcagagggttggggggtgtggccttgctcttcaga
gagggcagatctacttagggagatctcttggggaagaaaagtggtaggcacgacagttcctcacccttct
gagatgttgggattacttcccaagtcctctatttcttgcacttgtggagcaacaggaggaggcaatccta
gagtttctgtatcagtactcccgtcctttgatcagtcatttttttcacgaggcccccctaaagggatactt
gggctcgtccacctctatgtcgacccagctattccatgcatgggaaaaagtcactaatgttcatgtggtg
aagagagctctatcgttaaaagaatctataaactggttcattactagagattccaacttggctcaagctc
taattaggaacattatgtctctgacaggccctgatttccctctagaggaggcccctgtcttcaaaaggac
ggggtcagccttgcataggttcaagtctgccagatacagcgaaggagggtattcttctgtctgcccgaac
ctcctctctcatatttctgttagtacagacaccatgtctgatttgacccaagacgggaagaactacgatt
tcatgttccagccattgatgctttatgcacagacatggacatcagagctggtacagagagacacaaggct
aagagactctacgtttcattggcacctccgatgcaacaggtgtgtgagacccattgacgacgtgaccctg
gagacctctcagatcttcgagtttccggatgtgtcgaaaagaatatccagaatggtttctggggctgtgc
ctcacttccagaggcttcccgatatccgtctgagaccaggagatttttgaatctctaagcggtagagaaaa
gtctcaccatatcggatcagctcaggggctcttatactcaatcttagtggcaattcacgactcaggatac
aatgatggaaccatcttccctgtcaacatatacggcaaggtttcccctagagactatttgagagggctcg
caaggggagtattgataggatcctcgatttgcttcttgacaagaatgacaaatatcaatattaatagacc
tcttgaattggtctcaggggtaatctcatatattctcctgaggctagataaccatccctccttgtacata
atgctcagagaaccgtctcttagaggagagatatttctatccctcagaaatccccgccgcttatccaa
ccactatgaaagaaggcaacagatcaatcttgtgttatctccaacatgtgctacgctatgagcgagagat
aatcacggcgtctccagagaatgactggctatggatcttttcagactttagaagtgccaaaatgacgtac
ctatccctcattacttaccagtctcatcttctactccagagggttgagagaaacctatctaagagtatga
gagataacctgcgacaattgagttctttgatgaggcaggtgctgggcgggcacggagaagataccttaga
gtcagacgacaacattcaacgactgctaaaagactctttacgaaggacaagatgggtggatcaagaggtg
cgccatgcagctagaaccatgactggagattacagccccaacaagaaggtgtcccgtaaggtaggatgtt
cagaatgggtctgctctgctcaacaggttgcagtctctacctcagcaaacccggcccctgtctcggagct
tgacataagggccctctctaagaggttccagaacccttgatctcgggcttgagagtggttcagtgggca
accggtgctcattataagcttaagcctattctagatgatctcaatgttttcccatctctctgccttgtag
ttggggacgggtcagggggatatcaagggcagtcctcaacatgtttccagatgccaagcttgtgttcaa
cagtcttttagaggtgaatgacctgatggcttccggaacacatccactgcctccttcagcaatcatgagg
ggaggaaatgatatcgtctccagagtgatagatcttgactcaatctgggaaaaaccgtccgacttgagaa
acttggcaacctggaaatacttccagtcagtccaaaagcaggtcaacatgtcctatgacctcattatttg
cgatgcagaagttactgacattgcatctatcaaccggatcaccctgttaatgtccgattttgcattgtct
atagatggaccactctatttggtcttcaaaacttatgggactatgctagtaaatccaaactacaaggcta
ttcaacacctgtcaagagcgttcccctcggtcacagggtttatcacccaagtaacttcgtctttttcatc
tgagctctacctccgattctccaaacgagggaagtttttcagagatgctgagtacttgacctcttccacc
cttcgagaaatgagccttgtgttattcaattgtagcagccccaagagtgagatgcagagagctcgttcct
tgaactatcaggatcttgtgagaggatttcctgaagaaatcatatcaaatccttacaatgagatgatcat
aactctgattgacagtgatgtagaatcttttctagtccacaagatggttgatgatcttgagttacagagg
ggaactctgtctaaagtggctatcattatagccatcatgatagtttctccaacagagtcttcaacgttt
ccaaacccctaactgacccctcgttctatccaccgtctgatcccaaaatcctgaggcacttcaacatatg

(SEQ ID NO: 20)

Fig. 13 (cont.)

ttgcagtactatgatgtatctatctactgctttaggtgacgtccctagcttcgcaagacttcacgacctg
tataacagacctataacttattacttcagaaagcaagtcattcgagggaacgtttatctatcttggagtt
ggtccaacgacacctcagtgttcaaaagggtagcctgtaattctagcctgagtctgtcatctcactggat
caggttgatttacaagatagtgaagactaccagactcgttggcagcatcaaggatctatccagagaagtg
gaaagacaccttcataggtacaacaggtggatcaccctagaggatatcagatctagatcatccctactag
actacagttgcctgtgaaccggatactcctggaagcctgcccatgctaagactcttgtgtgatgtatctt
gaaaaaaacaagatcctaaatctgaacctttggttgtttgattgtttttctcatttttgttgtttatttg
ttaagcgtGGGTCGGCATGGCATCTCCACCTCCTCGCGGTCCGACCTGGGCATCCGAAGGAGGACGCACG
TCCACTCGGATGGCTAAGGGAGAAGGGCGAATTCCAGCACACTGGCGGCCGTTACTAGTGGATCCGAGCT
CGGTACCAAGCTTAAGTTTAAACCGCTGATCAGCCTCGACTGTGCCTTCTAGTTGCCAGCCATCTGTTGT
TTGCCCCTCCCCCGTGCCTTCCTTGACCCTGGAAGGTGCCACTCCCACTGTCCTTTCCTAATAAAATGAG
GAAATTGCATCGCATTGTCTGAGTAGGTGTCATTCTATTCTGGGGGGTGGGGTGGGGCAGGACAGCAAGG
GGGAGGATTGGGAAGACAATAGCAGGCATGCTGGGGATGCGGTGGGCTCTATGGCTTCTGAGGCGGAAAG
AACCAGCTGGGGCTCTAGGGGGTATCCCCACGCGCCCTGTAGCGGCGCATTAAGCGCGGCGGGTGTGGTG
GTTACGCGCAGCGTGACCGCTACACTTGCCAGCGCCCTAGCGCCCGCTCCTTTCGCTTTCTTCCCTTCCT
TTCTCGCCACGTTCGCCGGCTTTCCCCGTCAAGCTCTAAATCGGGGGCTCCCTTTAGGGTTCCGATTTAG
TGCTTTACGGCACCTCGACCCCAAAAAACTTGATTAGGGTGATGGTTCACGTAGTGGGCCATCGCCCTGA
TAGACGGTTTTTCGCCCTTTGACGTTGGAGTCCACGTTCTTTAATAGTGGACTCTTGTTCCAAACTGGAA
CAACACTCAACCCTATCTCGGTCTATTCTTTTGATTTATAAGGGATTTTGCCGATTTCGGCCTATTGGTT
AAAAAATGAGCTGATTTAACAAAAATTTAACGCGAATTAATTCTGTGGAATGTGTGTCAGTTAGGGTGTG
GAAAGTCCCCAGGCTCCCCAGCAGGCAGAAGTATGCAAAGCATGCATCTCAATTAGTCAGCAACCAGGTG
TGGAAAGTCCCCAGGCTCCCCAGCAGGCAGAAGTATGCAAAGCATGCATCTCAATTAGTCAGCAACCATA
GTCCCGCCCCTAACTCCGCCCATCCCGCCCCTAACTCCGCCCAGTTCCGCCCATTCTCCGCCCCATGGCT
GACTAATTTTTTTTATTTATGCAGAGGCCGAGGCCGCCTCTGCCTCTGAGCTATTCCAGAAGTAGTGAGG
AGGCTTTTTTGGAGGCCTAGGCTTTTGCAAAAAGCTCCCGGGAGCTTGTATATCCATTTTCGGATCTGAT
CAAGAGACAGGATGAGGATCGTTTCGCATGATTGAACAAGATGGATTGCACGCAGGTTCTCCGGCCGCTT
GGGTGGAGAGGCTATTCGGCTATGACTGGGCACAACAGACAATCGGCTGCTCTGATGCCGCCGTGTTCCG
GCTGTCAGCGCAGGGGCGCCCGGTTCTTTTTGTCAAGACCGACCTGTCCGGTGCCCTGAATGAACTGCAG
GACGAGGCAGCGCGGCTATCGTGGCTGGCCACGACGGGCGTTCCTTGCGCAGCTGTGCTCGACGTTGTCA
CTGAAGCGGGAAGGGACTGGCTGCTATTGGGCGAAGTGCCGGGGCAGGATCTCCTGTCATCTCACCTTGC
TCCTGCCGAGAAAGTATCCATCATGGCTGATGCAATGCGGCGGCTGCATACGCTTGATCCGGCTACCTGC
CCATTCGACCACCAAGCGAAACATCGCATCGAGCGAGCACGTACTCGGATGGAAGCCGGTCTTGTCGATC
AGGATGATCTGGACGAAGAGCATCAGGGGCTCGCGCCAGCCGAACTGTTCGCCAGGCTCAAGGCGCGCAT
GCCCGACGGCGAGGATCTCGTCGTGACCCATGGCGATGCCTGCTTGCCGAATATCATGGTGGAAAATGGC
CGCTTTTCTGGATTCATCGACTGTGGCCGGCTGGGTGTGGCGGACCGCTATCAGGACATAGCGTTGGCTA
CCCGTGATATTGCTGAAGAGCTTGGCGGCGAATGGGCTGACCGCTTCCTCGTGCTTTACGGTATCGCCGC
TCCCGATTCGCAGCGCATCGCCTTCTATCGCCTTCTTGACGAGTTCTTCTGAGCGGGACTCTGGGGTTCG
AAATGACCGACCAAGCGACGCCCAACCTGCCATCACGAGATTTCGATTCCACCGCCGCCTTCTATGAAAG
GTTGGGCTTCGGAATCGTTTTCCGGGACGCCGGCTGGATGATCCTCCAGCGCGGGGATCTCATGCTGGAG
TTCTTCGCCCACCCCAACTTGTTTATTGCAGCTTATAATGGTTACAAATAAAGCAATAGCATCACAAATT
TCACAAATAAAGCATTTTTTTCACTGCATTCTAGTTGTGGTTTGTCCAAACTCATCAATGTATCTTATCA
TGTCTGTATACCGTCGACCTCTAGCTAGAGCTTGGCGTAATCATGGTCATAGCTGTTTCCTGTGTGAAAT
TGTTATCCGCTCACAATTCCACACAACATACGAGCCGGAAGCATAAAGTGTAAAGCCTGGGGTGCCTAAT
GAGTGAGCTAACTCACATTAATTGCGTTGCGCTCACTGCCCGCTTTCCAGTCGGGAAACCTGTCGTGCCA
GCTGCATTAATGAATCGGCCAACGCGCGGGGAGAGGCGGTTTGCGTATTGGGCGCTCTTCCGCTTCCTCG
CTCACTGACTCGCTGCGCTCGGTCGTTCGGCTGCGGCGAGCGGTATCAGCTCACTCAAAGGCGGTAATAC
GGTTATCCACAGAATCAGGGGATAACGCAGGAAAGAACATGTGAGCAAAAGGCCAGCAAAAGGCCAGGAA
CCGTAAAAAGGCCGCGTTGCTGGCGTTTTTCCATAGGCTCCGCCCCCCTGACGAGCATCACAAAAATCGA
CGCTCAAGTCAGAGGTGGCGAAACCCGACAGGACTATAAAGATACCAGGCGTTTCCCCCTGGAAGCTCCC
TCGTGCGCTCTCCTGTTCCGACCCTGCCGCTTACCGGATACCTGTCCGCCTTTCTCCCTTCGGGAAGCGT
GGCGCTTTCTCATAGCTCACGCTGTAGGTATCTCA

(SEQ ID NO: 20)

Fig. 13 (cont.)

GTTCGGTGTAGGTCGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACTGGCAGCAGCCACT
GGTAACAGGATTAGCAGAGCGAGGTATGTAGGCGGTGCTACAGAGTTCTTGAAGTGGTGGCCTAACTACG
GCTACACTAGAAGAACAGTATTTGGTATCTGCGCTCTGCTGAAGCCAGTTACCTTCGGAAAAAGAGTTGG
TAGCTCTTGATCCGGCAAACAAACCACCGCTGGTAGCGGTggtTTTTTTGTTTGCAAGCAGCAGATTACG
CGCAGAAAAAAAGGATCTCAAGAAGATCCTTTGATCTTTTCTACGGGGTCTGACGCTCAGTGGAACGAAA
ACTCACGTTAAGGGATTTTGGTCATGAGATTATCAAAAAGGATCTTCACCTAGATCCTTTTAAATTAAAA
ATGAAGTTTTAAATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCCCCGTCGTGTAGATAA
CTACGATACGGGAGGGCTTACCATCTGGCCCCAGTGCTGCAATGATACCGCGAGACCCACGCTCACCGGC
TCCAGATTTATCAGCAATAAACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGTATGGCTTCATTCAGCTCCGG
TTCCCAACGATCAAGGCGAGTTACATGATCCCCCATGTTGTGCAAAAAAGCGGTTAGCTCCTTCGGTCCT
CCGATCGTTGTCAGAAGTAAGTTGGCCGCAGTGTTATCACTCATGGTTATGGCAGCACTGCATAATTCTC
TTACTGTCATGCCATCCGTAAGATGCTTTTCTGTGACTGGTGAGTACTCAACCAAGTCATTCTGAGAATA
GTGTATGCGGCGACCGAGTTGCTCTTGCCCGGCGTCAATACGGGATAATACCGCGCCACATAGCAGAACT
TTAAAAGTGCTCATCATTGGAAAACGTTCTTCGGGGCGAAAACTCTCAAGGATCTTACCGCTGTTGAGAT
CCAGTTCGATGTAACCCACTCGTGCACCCAACTGATCTTCAGCATCTTTTACTTTCACCAGCGTTTCTGG
GTGAGCAAAAACAGGAAGGCAAAATGCCGCAAAAAAGGGAATAAGGGCGACACGGAAATGTTGAATACTC
ATACTCTTCCTTTTTCAATATTATTGAAGCATTTATCAGGGTTATTGTCTCATGAGCGGATACATATTTG
AATGTATTTAGAAAAATAAACAAATAGGGGTTCCGCGCACATTTCCCCGAAAAGTGCCACCTGACGTC

(SEQ ID NO: 20)

Fig. 13 (cont.)

5'-
ACGCUUAACAAAUAAACAACAAAAAUGAGAAAAACAAUCAAACAACCAAAGGUUCAGAUUUAGGAUCUUG
UUUUUUUCAAGAUACAUCACACAAGAGUCUUAGCAUGGGCAGGCUUCCAGGAGUAUCCGGUUCACAGGCA
ACUGUAGUCUAGUAGGGAUGAUCUAGAUCUGAUAUCCUCUAGGGUGAUCCACCUGUUGUACCUAUGAAGG
UGUCUUUCCACUUCUCUGGAUAGAUCCUUGAUGCUGCCAACGAGUCUGGUAGUCUUCACUAUCUUGUAAA
UCAACCUGAUCCAGUGAGAUGACAGACUCAGGCUAGAAUUACAGGCUACCCUUUUGAACACUGAGGUGUC
GUUGGACCAACUCCAAGAUAGAUAAACGUUCCCUCGAAUGACUUGCUUUCUGAAGUAAUAAGUUAUAGGU
CUGUUAUACAGGUCGUGAAGUCUUGCGAAGCUAGGGACGUCACCUAAAGCAGUAGAUAGAUACAUCAUAG
UACUGCAACAUAUGUUGAAGUGCCUCAGGAUUUUGGGAUCAGACGGUGGAUAGAACGAGGGGUCAGUUAG
GGGUUUGGAAACGUUGAAGACUCUGUUGGAGAAAACUAUCAUGAUGGCUAUAAUGAUAGCCACUUUAGAC
AGAGUUCCCCUCUGUAACUCAAGAUCAUCAACCAUCUUGUGGACUAGAAAAGAUUCUACAUCACUGUCAA
UCAGAGUUAUGAUCAUCUCAUUGUAAGGAUUUGAUAUGAUUUCUUCAGGAAAUCCUCUCACAAGAUCCUG
AUAGUUCAAGGAACGAGCUCUCUGCAUCUCACUCUUGGGGCUGCUACAAUUGAAUAACACAAGGCUCAUU
UCUCGAAGGGUGGAAGAGGUCAAGUACUCAGCAUCUCUGAAAAACUUCCCUCGUUUGGAGAAUCGGAGGU
AGAGCUCAGAUGAAAAAGACGAAGUUACUUGGGUGAUAAACCCUGUGACCGAGGGGAACGCUCUUGACAG
GUGUUGAAUAGCCUUGUAGUUUGGAUUUACUAGCAUAGUCCCAUAAGUUUUGAAGACCAAAUAGAGUGGU
CCAUCUAUAGACAAUGCAAAAUCGGACAUUAACAGGGUGAUCCGGUUGAUAGAUGCAAUGUCAGUAACUU
CUGCAUCGCAAAUAAUGAGGUCAUAGGACAUGUUGACCUGCUUUUGGACUGACUGGAAGUAUUUCCAGGU
UGCCAAGUUUCUCAAGUCGGACGGUUUUUCCCAGAUUGAGUCAAGAUCUAUCACUCUGGAGACGAUAUCA
UUUCCUCCCCUCAUGAUUGCUGAAGGAGGCAGUGGAUGUGUUCCGGAAGCCAUCAGGUCAUUCACCUCUA
AAAGACUGUUGAACACAAGCUUGGCAUCUGGAAACAUGUUGAGGACUGCCCUUGAUAUCCCCCCUGACCC
GUCCCCAACUACAAGGCAGAGAGAUGGGAAAACAUUGAGAUCAUCUAGAAUAGGCUUAAGCUUAUAAUGA
GCACCGGUUGCCCACUGAACCACUCUCAAGCCCGAGAUCAAAGGGUUCUGGAACCUCUUAGAGAGGGCCC
UUAUGUCAAGCUCCGAGACAGGGGCCGGGUUUGCUGAGGUAGAGACUGCAACCUGUUGAGCAGAGCAGAC
CCAUUCUGAACAUCCUACCUUACGGGACACCUUCUUGUUGGGGCUGUAAUCUCCAGUCAUGGUUCUAGCU
GCAUGGCGCACCUCUUGAUCCACCCAUCUUGUCCUUCGUAAAGAGUCUUUUAGCAGUCGUUGAAUGUUGU
CGUCUGACUCUAAGGUAUCUUCUCCGUGCCCGCCCAGCACCUGCCUCAUCAAAGAACUCAAUUGUCGCAG
GUUAUCUCUCAUACUCUUAGAUAGGUUUCUCUCAACCCUCUGGAGUAGAAGAUGAGACUGGUAAGUAAUG
AGGGAUAGGUACGUCAUUUUGGCACUUCUAAAGUCUGAAAAGAUCCAUAGCCAGUCAUUCUCUGGAGACG
CCGUGAUUAUCUCUCGCUCAUAGCGUAGCACAUGUUGGAGAUAACACAAGAUUGAUCUGUUGCCUUCUUU
CAUAGUGGUUGGAUAAGCGGCGGGGAUUUUCUGAGGGAUAGAAAAUAUCUCUCCUCUAAGAGACGGUUCU
CUGAGCAUUAUGUACAAGGAGGGAUGGUUAUCUAGCCUCAGGAGAAUAUAUGAGAUUACCCCUGAGACCA
AUUCAAGAGGUCUAUUAAUAUUGAUAUUUGUCAUUCUUGUCAAGAAGCAAAUCGAGGAUCCUAUCAAUAC
UCCCCUUGCGAGCCCUCUCAAAUAGUCUCUAGGGGAAACCUUGCCGUAUAUGUUGACAGGGAAGAUGGUU
CCAUCAUUGUAUCCUGAGUCGUGAAUUGCCACUAAGAUUGAGUAUAAGAGCCCCUGAGCUGAUCCGAUAU
GGUGAGACUUUUCUCUACCGCUUAGAGAUUCAAAAUCUCCUGGUCUCAGACGGAUAUCGGGAAGCCUCUG
GAAGUGAGGCACAGCCCCAGAAACCAUUCUGGAUAUUCUUUUCGACACAUCCGGAAACUCGAAGAUCUGA
GAGGUCUCCAGGGUCACGUCGUCAAUGGGUCUCACACACCUGUUGCAUCGGAGGUGCCAAUGAAACGUAG
AGUCUCUUAGCCUUGUGUCUCUCUGUACCAGCUCUGAUGUCCAUGUCUGUGCAUAAAGCAUCAAUGGCUG
GAACAUGAAAUCGUAGUUCUUCCCGUCUUGGGUCAAAUCAGACAUGGUGUCUGUACUAACAGAAAUAUGA
GAGAGGAGGUUCGGGCAGACAGAAGAAUACCCUCCUUCGCUGUAUCUGGCAGACUUGAACCUAUGCAAGG
CUGACCCCGUCCUUUUGAAGACAGGGGCCUCCUCUAGAGGGAAAUCAGGGCCUGUCAGAGACAUAAUGUU
CCUAAUUAGAGCUUGAGCCAAGUUGGAAUCUCUAGUAAUGAACCAGUUUAUAGAUUCUUUUAACGAUAGA
GCUCUCUUCACCACAUGAACAUUAGUGACUUUUUCCCAUGCAUGGAAUAGCUGGGUCGACAUAGAGGUGG
ACGAGCCCAAGUAUCCCUUUAGGGGGCCUCGUGAAAAAAAUGACUGAUCAAAGGACGGAGUACUGAUAC
AGAAACUCUAGGAUUGCCUCCUCCUGUUGCUCCACAAGUGCAAGAAAUAGAGGACUUGGGAAGUAAUCCC
AACAUCUCAGAAGGGUGAGGAACUGUCGUGCCUACCACUUUUCUUCCCCAAGAGAUCUCCCUAAGUAGAU
CUGCCCUCUCUGAAGAGCAAGGCCACACCCCCCCAACCCUCUGAGGUGUCUGGGUCAUCCGACUAAUCCC
GUGGAUCUCUGAGUUGUAGAAGGAUUCUUCUAAAGUUUUGAGAGACUCUUUCUAAACUGCCUUCUUAUC
GUUCGGGAGUUUUGUAUCAAUCCAAUGAUUGACUCGGGGAUUCCCAAAAAAGACGAACUGAAUAGCUCAC
UGAGAAAUCGAGGAAACAGAGGCUCAACAGAUAUU

(SEQ ID NO: 21)

Fig. 14

AAGAAGAGUAUAAAAUUAUCUCUAUGGGUCUUGGACAACAGGAUUGCCUCUCGAAACUCUGAAUUUUCCA
CCUUGUCCACCUCGUCAUAUAAAGCCUUUCUGAUUGCAUCCUUGAGUAGAAUGGUAGGACUGGCCCCUCC
UCUGAUAUUUAAGGUGGUCGGAUCUUCUAGAAGGCGAGUGAAGCUCUCGAGUGUUCUCUCUCCAAGAUCU
GGGUUUCCAGCCUCUUGACACAACGCGUGAAUCCAGGACUCUUGGGAGCUUAACCAGAUCUCUCUCCAGA
AGGAUAACCCUUCAGAGACAGGGUCUGAGAACUGUCGUAUAUGGAAUCUUCCGAGGGACAUUCCAGAUAU
CCCUCCCAAAGAAGGAUCUAGAUAGAUUAUCCUUGACAUGGCUAGGAGAAAGCUCUCCCCUUCAGCGCUC
AGAAUCUUGUAAACUCUUCCCUUUAAGAUUGGGCUAAAUAGCAGGUAGUGAAAGACUGCCUGUACUGACA
UGAGCAGAAAAUCCCUCAUCGGUUUGAUCAAAGAUUGAGAGUGUUGUGCCACUGUUAGCGCAUUGGUGGA
CACUGUCGACAUUAUAUUGGCGAGGUUGACUAUUUGGUCAUUAGAGACGCAAGAGACUCUGGCCCAUCUU
UUGGACUCAGGCACCAAUAUGUUACCUCUAAACAAAGGGGUUUUUCCAUAGAUGAGGAAGUCAUAACUAC
ACAUGGUCUCUUCUUUCUUGAUGAUCAGCCCUAGCUUAGAUGCCCCUUCCUCGACGGCUCUGUAUAUCGA
AAGUGCAUUCCUUGAUAUUCUCUCCAAUUCAUAGAGGAGCCCCUCUUGAGAUAGCCCUGGCGACAACAUG
UAUGUCGGACAUAAAACCUGGUUGUCUCCUUGAGCUAGUAUUUUGGUUCUUGUGUUCCUGAUUUGAGAUU
CUCUAUCUAUCAUCAAUAAGCUGACUAGACUCCAGCCCUUCUGCCGUAAGCCUUCUAGCCCGCCAUCCUG
GCCAUUCCAACAGGUUGGGCCGUUGGACGCAUCUAAGCAGUAUAUUUGAUCCUCCCGUAACCCGAUGAGG
UCUGAUCUGUCUGAAUAAUAGAUCCAGGCCUUUUGAAAAAACUCGUGUGUUCUAGAAAACACUCUCUUCA
AUCCAAACACUUGAUCUAGGACAGAAAAUACAUCCUCUGUUGACUCUAAUCUUUGAUGGUUGUUCCACUU
UUCAUAGUCCAGGUGAAAUGCAUAUGUGACCCUUGAAUAGUCCAAAAGCCCUUGCCCGGUGACCCUGUCG
AUCAGCUUUUUAAACACCUUGUUCAGGUUGUCUGUCAUAGUCAGCGCGUCAAAAAGUGGCAAGAUGUAGU
UGGCCAAGAGUUUUUCAGUGAUGACAAAAUACAAUCUUAGAUUCCAUGACAUUAGAGCAAAGAAUCGACC
UUCAAUCUUCAAUUCCCGUUCCUUUGGCUUGAGGCCAAUUAUCAAGUCUUCAUCUGGCAAUCCUCCGAGG
UCUAUAGACCUCAGAAACUCUCGGGGAUUGACAGGCGGCUUAGACAGGGCCGUGAUAAUAACUUUUUCGC
UAGGAACAGGCCCCCCUCGGUUUUCUGACAGCCAAGAAGCUAGUCUCGUUCUGGUGAAAGAAUGUGAUUU
GUCAUCCAAUAUUUCUGACGGAUCCAUUGAUUCAGGAAUCUCAAAGAUCUGCGUGAUCGGGAGCUUGUGC
CAUGUAUCCCCCACCAAGUCUACAAUAUGUUUGGGUGGCCAUGUUUGGGUUUUGAUAUAAGGAGUCAAGG
GGUGGUCUCGGGCUAGGAAUCUUGAAUCCAGAUACCACUUGGAGUACUUAUCAAAACCCCAUCUAAGGAU
CCUCCUGGCUAGGUCGCUUGCUAAGCACUCCUGGUAGGACUUAUCUAUCAUUUUUUUAAGGUGAACCUGA
UCAUAUAGUUUUGACAGACCCUUUCGAUAAUCUAUAUAUGGGUGCCCCCAAUGCCUGUAACAGCCAAACA
CAAAAACCAAGUCAUGUAUGUUGUCGAAUUGAUCCAGAGCCCUAAAGAACCUUCUUGCACAGGGACCGAA
CGUCUCUUCAAGUUGACUUACCUUGUCUUUUAUAAAUACAGGAAAGUCUCCCAAGGAAUGAAUGAGAGGC
CUAAACUUUUCUGCUCUCUGGACUAAACUAUUCACGACAUAUGGCUCCAAUAUUUUGAUGACUUCAUAGC
CGGAGUUUCCACACAUAGACAAGACUUGAUCCCCAGCAAUGUACAGCUGGCAUAGUUGAGAUAUCAAGUC
AUCUGAGUAUCGGGGCUCUGGGGGAGAGAGCAAGACCAUUAAGGAGUUGAAGCGAGACAAGAAAAGAUCU
UUUAGCAUAAGUGUGUAGUUUCUGUCAAAAAGACAAUUGGAACUUUGGGAGUAAACAAAGUCCUUUGUCA
CGAUCAGCAGUCCCCAUAUUUGGUCUUUGAACUUUACCAAGUCCUUCCCGAUGUCCACUGAGGUUAAAUC
UUUCCAUAAUGCUAGGAUGGUCUUUUCUUCAUCCCAGUCUAGGGCGUUCAUGUAUAAGGUGAUUACAUGG
AAGAACAAGUAAGAGGAAUACGUGUUGGCAAGAUACCUUCCAAAUGCAUUAUCAUAAUCAACCCUCUCAA
GGCAACUUAACACUCCCUCUGGGGGGAUUCUCAGCCCUCUAUUUCCUAGCGUGAGAUUCAACAGCUUCUC
UAUGGGGGACGACUUGGAAUAGAAAUGGGCCAAGUCUGUUAUACAUCUCCGGCUCCUGUUGGAUUCAGAG
UGGGCACCAUAUAACCAGAGAGAAAUCAUUGACUGUGCAGCCAUUCCGCCCACCUUGAGAGAACCCAAAU
CUACCUUCUUGAAAUAAUCUUUCAAAACUCUGAAAGACCUGGAGCAAUUGUCUGUUAGAGUCAUCCGAUA
AGGUCUAUUCCCUGUUUUUAACCAUUCUAACAUUAGUCUAGCAGGAUCUUCUAUCAAAGGAGAGUUGAGA
UUGUAGUCAGAGUUCCUCAAGAUGUUGGGGACAAUGGGGGUUCCUCUGGGUUCAGCCUCUAACUCGAUUG
GGUCAAUAGGGUCAUCAUAGACCUCUCCAGGAUCGAGCAUCUUGAAGUAAGUCUCAGGUUGAGAAAGUGU
UGCCAGUUGUUCUUCUGAUCUAAUGUUUUUUUCUCGACUGAAAAGCUACCGCGGGUAGGCGCGCCGUAUU
AAUUAAGGAGGGGUGUUAGUUUUUUUCAUGCUAGCGUAGCCCGGGCGUAGCGGCCGCGUACCUGCAGGUC
CUUUGAGGGAUGUUAAUAGUUUUUUUCACAUCCAAGAGGAUCAAAAUGUAAAGGUAAUCAACUUGACUUU
GAUGAAAUGCAGCGGUUUAAUGGCACCAUAACAUGUUUUUUGUUAUAUUGCUCCCAAGGGUUGGAGUUGA
GCCCAUAUGUUCUCUCCUCCAGAGGUAAACAAGUGAUAAAUUUGCGGGAUAUAAUCUGACGUACGUUAUU
CUAGAAGCAGAGAGGAAUCUUUGUCCUCUUCGGACCUUUGUGUCUGAAGAGACAUGUCAGACCAUAGUUG
ACAUGCUCUCGGGUUCAUGUUGAUACACCAGACUCUGCCCUGGAUAUGACACUGUUUUGCAAUCACUCUU
AUUUGCAAUCCGACGAACUCAGUAUCAUCAUCCCAAGUGAUCUCCUGAGAGUAUUCCAACUCCUCCCCUU

(SEQ ID NO: 21)

Fig. 14 (cont.)

CAAGAGGGCCCCUGGAAUCAGCCCACUGGAAGAUAAAGGUUCUCCUCAAUUUGUAUACCCAGUUCAGGCC
CUCAGGGACUGGAGAUCCUGACAAAGCCAGUCCAAUAACCACUUUGACUAACCCGAUCAUCCUAUGAUUC
CCAGAAUAUAUCUCGUCGAAUGAUUUCAGAAUGUGCCGCAGGAUCCUGAACGAGUAACCAUUCGGGCUAC
ACACUUUAACCCUUCCGUUGAUACAAAAGUUCCUCAUGUUCUUCUUGCCUGUAAGUUCUUUCAGCGGGAC
GUAUUCAGGGGGUGGAAGCCACAAGUCAUCGUCAUCCAGAGGGGCUGACGCGGGAGAGGAUUUUUGAGUG
UCCUCGUCCCUGCGGUUUUUCACUAUCUUACGUAGGAGGUUCAUCGAUUUAUCAGUGGUGUUGCCUGUUU
UUUUCAUGUUGACUUUGGGACAUCUCGGAUUUUAUUGUCUAGAGGGACUGAGGGGAGAGGUUCGGUUAGC
AAGAUGUAUAGCGAUUCAAGUCAUCUUGCAUGAUUUUACUCAGCUUGUCGGAUUCGACUAACAACUGGAA
UUUCUUAGAGUUGGCCAAAGCGACCCAUCCCAGUACACAUCUUAGGGGGAGUUUGGACCCGUCAUGGGCU
AAACGGGUCACACCUGGUACAUUUUUUGCCUCUUUAACUAUAUCAUCAAGGUUCAUUUUCAAUUGCUCAA
AAUUAUACAAGAGUAUCCCUGAGGAUCGAGAGGGAAACUUAUAUUUUUUGGAGAAACUUUCUGCAAUCUG
GUGAGCGAUCUCAGCCUCCACUGAUAGAUCAUCCUCUUCAUUGGUAGCCGACCAUUCAAGGGCUGGAGGG
CCAGAAGCAAUUUGAGCCGCCAUCCUGGCUUUCGAUGAUUGGCUUUCUCUCUGAGAAGGAGUGGGUGUUG
UCUCCUUCUUGAGCUCUCGGCCAGUAGUCUGGGUUGAUUUAUCCUCUGAAGACUUUCCUGGAGGGUUGGG
AAAGUUGACCGCGACAUAGGAUAUAAUCUCUUCUACGGUCUGUGACCAUAUCUUGAGAAAUCUCUCUCCU
GACCUCAUUUGUCUGACUAUUUGGACUCCAACAUUUUCCAGGUAUGACUGGAACAGGAAGCUAGGAUCCU
CUCCUUCAUCCAUCUGAAAGUCCUCUCGAUACUUGCCUUCUCCCACCUUGGCUAUCUCACCAUGGUUGGG
CGAUUUUCCAUCAUCCAGGUGAAGUCGCCCCAUAUCCUCAGGGAGAUUGUCCACCUCUAUGGGUUCCCCU
UGGAGAUGAGCCUGAUUGUCUUCGAUAUUUCUAUUGAUCAGAUCAACAGUUUCUUCAGCCAUCUCAAGAU
CGGCCAGACCGGCUCUAAUAGCACUAGGAUUGACAAAGAUCUUGCUCAUGUUUGGGAUGGUUCGAAAGGA
GGGGUGUUAGUUUUUUUCAUGAUGGAUAUACACAAUCCGUAGAUUUCCGGCAUUUUGUUAUUCAACUUCU
UACACAUUGAUCCUAGCAGAAGCACAGGCUGCAGGGUGACGGUCCAUCCCGCUCUCCUGGGCACAAGACA
UGGGCAGCGUGCCAUCAUCCUGCUCCUCCACCUCCGGCGGGAAGCCAUGGCUACCGGAUCCCGAUUGGAA
GUAGAGGUUCUCUCCGGAACCUGAGUCACUCGAAUAUGUCUUGUUUAGAAACUCGGCGAAUGAGUUUGGA
CGGGCUUGAUGAUUGGAACUGACUGAGACAUAUCUCCGUAUGUGAGAUCUCUUUAGUCGACCUCCAUUCA
UCAUGAUUCGAGUAUAAACAGCCUCCGGACUUCUGGUUUCACCUGAAAAGUAGUCCUCGUCGUCAGAGUU
GACAGUUCCAUCAUCUGCCAGUGCUACGUCAGUCUUUGUCAGUUCAGCCGCCUCGUAUUCUUGAAGUUCU
UUCUCAUCUCUGAAGAAUCUUCUUUCAAAUGUCCCUUUCCCGAAGAAUUCCUCUCCCAGAUAGCCCCCUA
GAACAGACAUUUCAUGAGGAGCACAUGCAGCAAUAACCGUUGCAUUUAGGGAUCUGACUUGACCCAUAUA
GCAUCCUACAAAGUGAAUGAGAUUGAACACGUGACCAACAGCAUUUGAUGAAUAAGGAGAUUUCCCACUC
AAGCCUAGUGAACGGAAGUGGAUGAAAUAAGAGUGAGGAACAGCUGUCUCCUGCCCUGGCUCAAACAUUC
UUCUUAUCUCUUCCUCAAAGUUCUUGUGGAAGAAAUAUAGUAUUGCCUCUCUAGCGGUGAGAUUGAUUUG
UUUUAUGAACCCAGUAAAUGAUACCAGUCCUGAACAGUCUUCAUAAGCAGUGACAACUGUGCCCACUCUG
AUUGCUGAAUAUAGAUGCUCAAUCCGGGAGAAAAACAUGUCAUAGGUUCCGGCCAAAAAUCUGAAGUUUG
GUAUAGUACUCCAAUUAGCACACAUUUUGUGAGUUGUCAUUAGAGUAUGGUGUUCCACGAUUUUAACAAA
AGGGGCUGUCUCAAAAAUCUGCUCUAUCCUGUCUGCAAUGUUUGUCUUAUAGUUACCAGUGUUUUGCCCG
GAUAUUUUGCUCAACCUAUACAGACUCAAGAGAAGACCGACUAAGGACGCAUGCUCAGGGACAGUGGGGU
CUCUUGUCAGUUCCAUGCCUCCUGUCAGAGCCCAAUUCCCUUCUACAUCAGUACGUUUUAUCUCCACCAG
AGAACCUGGGGUGAUCUUAUCUCCUUUUCGUGCAAUCACAAUUCCAUAGCUGGUCCAGUCUUCCGGACAU
GUCCCCUCAAAAAACUGCAUUGCCGCUGCCAAAUAGGAACAUACAUCGUCAGGAUUAAGUUUGGCGGCGC
UCAUGCCUGACAAAACUGACUUGUAUGCUUUAUUUAAAUCGGGAGCCUUUCCUAGGGUUAUACAGGGCUU
UUUCAAAUCUUUGAUGGCAGGGUACUUGUACUCAUAUUGAUCCACGAUAAUCUCAGGCUUCAAAGAGACC
ACCUGAUUAUUGACUUUGAAUACAAUCUUGUCGGCAUCCAUUGUAGGGGUGUUACAUUUUUGCUUUGCAA
UUGACAAUGUCUGUUUUUUCUUUGAUCUGGUUGUUAAGCGU-3′

(SEQ ID NO: 21)

Fig. 14 (cont.)

SELF-INACTIVATING RABIES VIRUS VECTOR ENCODING A NUCLEOPROTEIN AND DEGRON

This application is a national phase entry pursuant to 35 U.S.C. § 371 of International Application No. PCT/GB2018/051166, filed May 2, 2018, which claims the benefit of priority from GB Application No. 1706945.1, filed 2 May 2017, the contents and elements of each of which are herein incorporated by reference for all purposes.

FIELD OF THE INVENTION

The invention relates to a vector based on a virus from the order Mononegavirales, such as a rhabdovirus, and in particular a rabies virus vector. More specifically, it relates to a vector which, having transfected a target cell, is switchable between replication-competent and replication-incompetent forms. Amongst other applications, the invention avoids the cytotoxicity associated with current vectors based on Mononegavirales such as rabies virus vectors.

BACKGROUND TO THE INVENTION

Vectors based on viruses of the order Mononegavirales have considerable potential in various therapeutic, diagnostic and research contexts. Although these vectors can be engineered such that they do not propagate from a transfected cell, or are able to propagate only in a tightly controlled manner, they still show significant cytotoxicity to transfected cells which limits their application.

For example, neurotropic viruses, particularly G-deleted rabies (ΔG-Rabies) (12, 13), by spreading from neuron to neuron along circuit paths, provide a potential tool to gain genetic access to topologically defined neurons (13-16).

However, despite the transformative role of ΔG-Rabies based approaches in the anatomical investigation of neuronal circuits, viral induced cytotoxicity prevents their use to follow network dynamics or manipulate functional properties of neural networks in vivo for periods longer than 5-15 days following the rabies infection (17-19). One possible solution to eliminate viral cytotoxicity would be to silence viral transcription after the primary infection. With DNA based viruses, such as Adeno-Associated Viruses (AAVs), this is traditionally achieved by inverting the viral genomic cassette in a CRE-recombinase dependent manner; flipping the genomic cassette effectively toggles the virus ON or OFF (20). Such an approach is currently precluded for RNA-based viruses, such as the rabies virus, due to the absence of reliable RNA recombinases.

Thus there remains a need for improved mononegaviral vectors which address the issue of cytoxicity.

SUMMARY OF THE INVENTION

Given the coupled nature of transcription and replication in viruses of the order Mononegavirales, the inventors hypothesised that conditional modulation of viral protein stability might act as a switch for the viral transcription-replication cycle within infected cells, turning the virus on or off when specific conditions are met.

Thus the inventors have designed a viral vector which is capable of transfecting (and hence delivering a genetic payload to) a target cell, and which is switchable between an active state in which viral protein expression is possible and an inactive state in which viral protein expression is inhibited. Continued maintenance of the inactive state will typically result in the vector being eliminated from the host cell.

In particular, the vector encodes a "replication modulator protein" which comprises a mononegaviral protein required for replication of the vector genome, and which is capable of adopting two configurations.

The mononegaviral protein which forms part of the replication modulator protein is referred to here as the "viral protein moiety".

In one configuration, referred to as the "targeted" configuration, the replication modulator protein is targeted for degradation in the target cell. Thus the "targeted" configuration is unstable. While the replication modulator protein maintains this configuration, expression from the vector genome and/or replication of the vector genome is inhibited or completely suppressed.

The second configuration of the modulator protein, referred to as the "untargeted" configuration, is more stable than the "targeted" configuration. As a result, it supports higher levels of expression from the vector and/or replication of the vector genome, typically because the viral protein moiety accumulates in the host cell cytosol to higher levels than the targeted configuration.

References to "stability" in this context relate only to the half life of the relevant proteins in the target cell and their propensity to be degraded by the target cell's protein degradation pathways. The targeted configuration has a shorter half life than the untargeted configuration and is thus regarded as being less stable than the untargeted configuration.

Thus the replication modulator protein provides a switch which enables strictly regulated expression from the vector genome and/or replication of the vector genome.

Typically, the "targeted" configuration of the modulator protein displays a degradation targeting signal or "degron", i.e. a moiety that marks the protein for degradation within the cell. The terms "degron" and "degradation targeting signal" are used interchangeably in this specification.

The "untargeted" configuration of the modulator protein differs from the targeted configuration in that it either does not comprise or does not display the degron responsible for the lower stability of the targeted configuration. As a result, the untargeted configuration typically has a longer half-life within the cell than the targeted configuration.

Degrons which may be employed in the context of the invention are discussed in more detail below.

The default state of the replication modulator protein may be the targeted configuration. That is to say, the targeted configuration may be encoded by the vector genome, such that the replication modulator protein is synthesised in the targeted configuration. Adoption of the untargeted configuration is stimulated by contact with an agent which may be referred to as an "activating agent" or "stabilising agent", since it supports production of sufficient functional protein to activate vector expression and/or replication. As result, may it permit the on-going persistence or survival of the vector within the cell.

A replication modulator protein having the targeted configuration as its default state may be referred to as an "inhibitory" replication modulator protein, since expression from a vector encoding such a modulator protein (or replication of such a vector) will tend to be inhibited except in the presence of the cognate activating agent. Thus an "inhibitory" modulator protein is constitutively unstable.

When a vector encoding a replication modulator protein having a default targeted configuration first infects a target cell, the initial level of protein synthesis may be sufficient to support a period of replication and potentially production of infectious progeny virions (depending on the payload of the vector and any other proteins provided in trans by the target cell). Thereafter, due to the instability of the replication modulator protein, replication is inhibited or completely suppressed in the absence of the activating agent.

Alternatively, the default state of the replication modulator protein may be the untargeted configuration. That is to say, the untargeted configuration of the replication modulator may be encoded by the vector genome, such that the replication modulator protein is synthesised in the untargeted configuration. Adoption of the targeted configuration is stimulated by contact with an agent which may be referred to as a "inhibitory agent" or "destabilising agent", since its presence will tend to inhibit or suppress expression from the vector and/or replication of the vector genome.

A replication modulator protein having the untargeted configuration as its default state may be referred to as an "inhibitable" replication modulator protein since expression from a vector comprising such a modulator protein will tend to proceed except in the presence of the cognate inhibitory agent.

In many embodiments, the replication modulator protein comprises a viral protein moiety and a regulator moiety. The viral protein moiety and the regulator moiety may form distinctly folded domains of the modulator protein, although this may not always be necessary. The viral protein moiety is typically capable of exerting all the biological functions of the native form of the relevant viral protein.

The nature and identity of the regulator moiety (when present) determines whether the modulator protein is an inhibitory modulator protein (i.e. vector expression or replication is inhibited in the absence of the cognate activating agent) or an inhibitable modulator protein (i.e. vector expression or replication proceeds as normal in the absence of the cognate inhibitory agent).

For an inhibitory modulator protein, the regulator moiety comprises or consists of the degron, and in the default state of the modulator protein, the degron is displayed such that the protein is targeted for degradation. The cognate activating agent will therefore act to remove, mask or otherwise disable the degron, e.g. by covalent or non-covalent modification. For example, the cognate activating agent may cleave the regulator moiety from the viral protein moiety. Thus the activating agent may be a protease which is capable of acting on the modulator protein to cleave the regulator moiety from the viral protein moiety. This mechanism may be described as "cleavage-induced stabilisation" of the replication modulator protein (or of the viral protein moiety). Alternatively, the activating agent may bind to the modulator protein, e.g. to the regulator moiety, to mask or otherwise inactivate the degron. Thus the activating agent may be a ligand for the modulator protein, e.g. for the regulator moiety of the modulator protein. This mechanism may be described as "ligand-induced stabilisation" of the replication modulator protein (or of the viral protein moiety).

For an inhibitable modulator protein, the regulator moiety does not comprise or does not display the degron in its default state. Rather, the cognate inhibitory agent will interact with the modulator protein to create or reveal the degron, typically by covalent or non-covalent interaction with the regulator moiety. Thus the cognate inhibitory agent may cleave the regulator moiety from the viral protein moiety in order to reveal or create the degron in the viral protein moiety. This mechanism may be described as "cleavage-induced destabilisation" (or "cleavage-induced degradation") of the replication modulator protein. Alternatively the inhibitory agent may bind to the replication modulator protein, e.g. to the regulator moiety, so as to create or reveal the degron. Thus the inhibitory agent may be a ligand for the modulator protein, e.g. for the regulator moiety of the modulator protein. This mechanism may be described as "ligand-induced destabilisation" (or "ligand-induced degradation") of the replication modulator protein. Thus, the regulator moiety and the inhibitory agent may respectively represent first and second components of an inducible degron system, wherein association of the first and second components generates a degron.

Thus, the invention provides a mononegaviral vector genome comprising a gene encoding a replication modulator protein, wherein the replication modulator protein comprises a mononegaviral protein moiety which is required for replication of the viral genome, the replication modulator protein being capable of adopting a targeted configuration displaying a degron, and an untargeted configuration which does not display the degron.

The vector genome is typically a negative-sense, single stranded RNA molecule.

As described above, the replication modulator protein encoded by the vector genome may be an inhibitory modulator. It may comprise a viral protein moiety and a regulator moiety, wherein the regulator moiety comprises or consists of the degron.

The replication modulator protein may be switchable to an untargeted configuration on contact with a cognate activating agent. In some embodiments, the activating agent is capable of cleaving the regulator moiety from the modulator protein. In other embodiments, the activating agent is a ligand for the modulator protein, e.g. for the regulator moiety. The ligand may mask or otherwise inactivate the degron, e.g. sterically or via a conformational change.

Alternatively, the replication modulator protein encoded by the vector genome may be an inhibitable modulator which is switchable to a targeted configuration displaying a degron on contact with a cognate inhibitory agent. It may comprise a viral protein moiety and a regulator moiety.

In some embodiments, the inhibitory agent is capable of cleaving the regulator moiety from the modulator protein to create or reveal the degron. In other embodiments, the inhibitory agent is a ligand for the regulator moiety and creates or reveals the degron on binding to the regulator moiety.

Thus the activating agent or inhibitory agent, as appropriate, may act by cleaving the regulator moiety from the viral protein moiety in order to remove or reveal the degron respectively. In such embodiments, the activating or inhibitory agent is typically a protease. In such embodiments, the regulator moiety comprises a cleavage site for the protease.

The protease may be orthogonal to the target cell. That is to say, the protease recognises a cleavage site which is not found in the proteome of the target cell, i.e. the cleavage site is not found in native proteins encoded by and expressed in the target cell. Thus the particular protease may vary depending on the target cell. Examples of suitable proteases include viral proteases, especially proteases from viruses which are not mononegaviruses (e.g. Tobacco Etch Virus protease (TEVp) and human rhinovirus (HRV) 3C protease), Factor Xa, enterokinase and thrombin. Any of these may be suitable when the target cell is a neural cell.

Preferably, the protease selected does not act on any other proteins encoded by the vector genome, e.g. amongst the proteins encoded by the vector genome, only the replication modulator comprises a cleavage site recognised by the relevant protease.

The activating agent or inhibitory agent may itself be encoded by the vector genome. In such cases, expression or function of the agent will be inducible, typically by contacting a cell containing the vector genome with an appropriate inducer. For example, the vector may comprise one or more genes encoding an agent which is expressed in functionally inactive form and wherein function is induced on contact with an inducer.

Thus, the agent may be expressed as two or more separate protein moieties which require the presence of a functional inducer in order to associate into a functional form. Each of the component agent moieties may be expressed as a fusion with a partner protein, wherein the partner proteins associate on contact with the functional inducer.

More detail regarding inducible agents is provided below.

Any mononegavirus may be used as the basis for a vector as described. Those having non-segmented genomes are particularly appropriate. For many applications, it may be desirable that the virus is capable of infecting and replicating in mammalian cells. For example, the mononegavirus may be a rhabdovirus (e.g. a lyssavirus, such as a rabies virus) or a vesiculovirus (such as a vesicular stomatitis virus (VSV)).

The viral protein moiety of the replication modulator may comprise or consist of any one of the proteins common to the majority of mononegaviruses. These include the large protein (L), nucleoprotein (N or NP), phosphoprotein (P), matrix protein (M), or glycoprotein (G; also referred to as simply the "envelope" protein). This terminology is commonly used for rhabdoviruses, and is used in the present specification also to refer to their equivalents by function or sequence homology in other mononegaviruses. However, it is necessary to identify an appropriate viral protein moiety which provides adequate control over viral replication.

The viral protein moiety of the replication modulator protein is a protein which is required for expression from the viral genome (e.g. for transcription of mRNA from the viral genome) and/or for replication of the viral genome. Thus, the viral protein moiety is typically not the viral envelope protein (e.g. the glycoprotein or G protein) as, for most mononegaviruses, replication of the other viral proteins and the genome proceeds in the absence of the envelope protein.

Thus the large protein (L), nucleoprotein (N or NP), phosphoprotein (P) or matrix protein (M) may be preferred, e.g. the large protein (L), nucleoprotein (N or NP) or phosphoprotein (P).

The nucleoprotein (N or NP protein) may be particularly preferred, especially in rhabdoviral vectors such as rabies viral vectors. Indeed, the present inventors have found that only the N protein provides adequate control over viral replication in vectors based on the rabies virus.

Whichever mononegaviral protein represents the viral protein moiety of the replication modulator protein, it will be understood that the replication modulator protein represents the only copy of that mononegaviral protein in the vector genome. To put it another way, the vector genome does not contain a gene encoding a version of the same protein which exists only in the untargeted configuration.

Thus the vector genome may comprise genes encoding one, two, three or all four of an N protein, a P protein, an M protein and an L protein, wherein one of these proteins is provided as the viral protein moiety of a replication modulator protein.

The vector genome may comprise a gene encoding a replication modulator protein comprising an N protein as the viral protein moiety, and may optionally further comprise one, two, or three of a P protein, an M protein and an L protein.

The vector genome may comprise genes encoding:

(i) a replication modulator protein comprising an N protein as the viral protein moiety;

(ii) a P protein;

(iii) an M protein; and (iv) an L protein.

The vector genome may also comprise a gene encoding an envelope protein. The envelope protein may be native to the mononegaviral vector. For example, when the vector is a rabies virus, it may be a rabies virus G protein.

Alternatively, a different envelope protein may be incorporated to modulate infectivity of virions produced by the vector. Incorporation of alternative envelope proteins may be referred to as "pseudotyping". In such cases, the envelope protein may comprise an intracellular domain and optionally also a trans-membrane domain of an envelope protein native to the vector, and a heterologous extracellular domain, i.e. the extracellular domain is not from the same mononegaviral envelope protein as the intracellular domain. The extracellular domain may be from a different viral envelope protein (e.g. from an envelope protein from a different mononegavirus species, family or genus, or from an envelope protein from a different viral order), or may be any protein domain capable of binding to a receptor expressed on the surface of a target cell, as long as the envelope protein remains capable of mediating infection of the target cell by the virion.

For example, a rabies virus vector may comprise an envelope protein having at least the extracellular domain from a VSV envelope protein, avian sarcoma leukosis virus (ASLV) type A envelope protein, or ASLV type B envelope protein. It may comprise an entire envelope protein from VSV, ASLV type A, or ASLV type B. Alternatively, it may comprise an intracellular domain and optionally also a trans-membrane domain from a rabies virus G protein.

In some embodiments, the vector genome does not encode an envelope protein. Such virions are particularly useful for so-called "monosynaptic tracing" in neuronal cells.

In addition to any pseudotyped envelope protein, the vector genome may comprise one or more heterologous genes, i.e. a gene encoding an expression product (typically a protein or RNA molecule) which is not native to the vector genome, i.e. is not present encoded by a wild type virus of the same virus type as the vector. The heterologous gene or genes may be regarded as the "payload" which is to be delivered to the target cell by the vector. Thus the heterologous gene(s) may encode any expression product (whether RNA or protein) which it is desired to express in the target cell. The identity and function of the heterologous gene(s) will thus depend on the intended role of the vector. In many embodiments, the heterologous gene does not encode a mononegaviral expression product, or a viral expression product.

The heterologous gene may be located at any suitable site within the vector genome. In some embodiments, it is located between the genes encoding the M and L proteins, e.g. replacing the gene encoding the endogenous G protein.

The heterologous gene(s) may, for example, encode one or more of the following:

a marker protein, e.g. a fluorescent protein or a protein conferring antibiotic resistance;

a protein against which it is desirable to raise an immune response;

a recombinase, e.g. a CRE recombinase, e.g. where the genome of the target cell contains recognition sites for the recombinase;

- a nuclease, e.g. an RNA-guided endonuclease such as Cas9;
- a guide RNA (gRNA) molecule, e.g. for use in conjunction with an RNA-guided endonuclease;
- a repair template RNA, e.g. for use in conjunction with an RNA-guided endonuclease;
- a nucleic acid modulator of gene expression, such as a siRNA, RNAi, anti-sense RNA or ribozyme.

The heterologous gene or genes will be under the control of viral transcription regulatory sequences such as transcription initiator and terminator signals.

Where two or more heterologous genes are included, they will typically each have their own associated regulatory sequences. Heterologous gene expression may be affected by factors such as the transcriptional start site employed by the heterologous gene, and its spacing from the end of the gene located immediately upstream in the viral genome, i.e. the length of the intergenic region (IGR) between the end of the gene immediately upstream and the start of the heterologous gene. The N protein has the highest level of transcription in a rabies virus, so it may be desirable that the heterologous gene employs the transcriptional start site from the N protein. The transcriptional start site may, for example, have the sequence AACACCCCT (e.g. as seen in strains B19 and N2C) or AACACCTCT. Finke et al. (2000) have demonstrated that the length of IGR upstream of a gene affects its expression, and that shorter IGR sequences correlate with increased expression. Thus it may be desirable that the IGR sequence upstream of the heterologous gene is 5 nucleotides or fewer in length, e.g. 2 nucleotides. Where the IGR is 2 nucleotides in length, its sequence may be CT.

It may be desirable to include two or more heterologous genes, especially if they have complementary functions. For example, it may be desirable to include heterologous genes encoding an RNA-guided endonuclease, a guide RNA for that endonuclease (to direct the endonuclease to the desired site of the target cell chromosome), and optionally also a repair template RNA to direct the particular modification to be achieved at the target site. The heterologous genes may be adjacent to one another in the viral genome. The IGR sequence between the heterologous genes may, for example, be 5 nucleotides or fewer in length, e.g. 2 nucleotides. It may be desirable that each heterologous gene employs the N protein transcriptional start site from the N protein.

The endonuclease may be a Cas9 enzyme, such as Cas9 from *Streptococcus aureus* (saCas9), *Streptococcus pyogenes* (SpCas9), *Neisseria meningitidis* (NM Cas9), *Streptococcus thermophilus* (ST Cas9), *Treponema denticola* (TD Cas9), or variants thereof such as the D1135E, VRER, EQR or VQR variants of SpCas9. Due to its relatively smaller size, saCas9 and its variants may be preferred.

The term Cas9 is used here to include functional variants of Cas9 endonucleases such as Cas9 nickase and nuclease-dead Cas9 (dCas9).

The size of the heterologous genes which can be incorporated into the vector will depend on various factors, such as the specific virus on which the vector is based, the packaging capacity of the virion and which (if any) of the native viral genes have been deleted from the vector.

For example, in a rabies viral vector in which the G gene has been deleted, it is possible to include at least 3.7 kb of heterologous coding sequence without substantial effect on packaging efficiency, and even up to 4.0 kb, up to 4.5 kb, or up to 5.0 kb. See ref. 32.

The heterologous gene may also be heterologous to the target cell, i.e. the target cell does not naturally encode or express the product of the gene. Alternatively, the target cell may encode or express the gene product but under different regulatory control, such that the expression pattern of the gene product in the target cell is modulated by introduction of the heterologous gene.

The invention further provides a ribonucleoprotein complex comprising the vector genome in association with one or more viral proteins, e.g. one or more of N, P and L proteins. The vector genome may be in association with all of N, P and L proteins. The ribonucloprotein complex may be a functional viral nucleocapsid, capable of initiating transcription on introduction to the cytoplasm of a target cell. It may additionally comprise an M protein.

The invention further provides a mononegaviral vector virion comprising a mononegaviral vector genome as described herein. The virion typically comprises an L protein, an N protein, a P protein and an M protein, and also comprises an envelope protein. The envelope protein may be a native mononegaviral envelope protein. Alternatively, the virion may have been pseudotyped with a different envelope protein as described above to modulate its infectivity.

The virion typically takes the form of a ribonucleoprotein complex (comprising genome, L, N, M and P proteins) surrounded by a membrane envelope containing the envelope protein.

The virion is capable of delivering the genome to the target cell and of initiating transcription of the genome.

For the avoidance of doubt, the virion typically does not contain a replication modulator protein; i.e. the proteins in the virion are not switchable between targeted and untargeted configurations.

The invention further provides a positive sense nucleic acid molecule encoding a viral vector genome as described herein. The positive sense nucleic acid may be an RNA or DNA molecule. When it is a DNA molecule, it may be provided as part of an expression construct, comprising transcriptional regulatory sequences capable of directing synthesis of viral genome molecules. The expression construct may be provided as part of an episome (e.g. a plasmid) or may be integrated into the chromosome of a host cell.

The invention further provides a packaging cell comprising a nucleic acid construct encoding a vector genome and capable of producing virions as described herein.

Thus the packaging cell expresses L, N, M and P proteins and an envelope protein. The proteins are capable of forming infective virions also comprising the vector genome.

Depending on the structure and coding content of the vector genome itself, these proteins may be encoded by the vector genome or provided in trans by other nucleic acid constructs within the cell.

The proteins in the virion particle itself are typically not linked to degrons. Typically, the packaging cell will encode (and be capable of expressing) functional versions of all of the virion proteins, without degrons. However, if one of the virion proteins is only expressed in the context of an inhibitory replication modulator as described here, then the packaging cell must also contain (e.g. express) the cognate activating agent so that viral replication can proceed.

The constructs encoding any proteins to be provided in trans are typically DNA constructs, and may independently be chromosomally integrated or present as episomes such as plasmids.

The nature of the packaging cell will depend on the particular viral vector, but may be a mammalian cell such as a primate or rodent cell. It may be a fibroblast or any other suitable cell type, such as a HEK (Human embryonic kidney) 293 cell or a BHK (baby hamster kidney) cell.

Construction of packaging cells for rabies viral vectors, and other aspects of viral vector design, are described in Osakada and Callaway (2013) Design and generation of rabies virus vectors, Nature Protocols 8(8): 1583-1601. See also Wickersham et al. (2010) Production of glycoprotein-deleted rabies viruses for monosynaptic tracing and high level gene expression in neurons, Nature Protocols 5(3): 595-606.

The invention further provides a method of gene delivery to a target cell, comprising contacting the target cell with a ribonucleoprotein complex or a virion of the invention.

When a ribonucleoprotein complex is employed, it may be desirable to deliver it directly into the cell cytosol, e.g. by microinjection, or in conjunction with a carrier, such as a polymer or lipid, to facilitate transit into the cell.

In many embodiments, the target cell does not naturally express the agent responsible for the switch between the targeted and untargeted configurations of the modulator protein. When the vector encodes an inhibitory replicator protein, the activating agent is required for continued replication and propagation of the vector after initial primary infection. Thus, when further replication and propagation is desirable, the vector will often be employed alongside a delivery system for the activating agent, or the activating agent itself.

Where the vector encodes an inhibitable modulator protein, it may not be necessary to provide the inhibitory agent. However, it may be desirable that vector expression and replication should not proceed immediately, in which case the vector may be employed alongside a delivery system for the inhibitory agent, or the inhibitory agent itself.

Thus the method may comprise the step of contacting the target cell with the cognate activating agent or inhibitory agent, as appropriate. The target cell may be contacted with the cognate activating agent periodically, e.g. at repeated intervals of 1 day to 1 month, e.g. at intervals of 1 day to 14 days, e.g. at intervals of 5 to 10 days, for an indefinite period of time. Such periodic administration may be useful to maintain viable vector within a target cell without permitting sufficient transcription and viral replication to compromise the cell.

Where the agent is a protein, the method may further comprise introducing into the target cell a nucleic acid comprising a gene encoding a cognate activating agent or inhibitory agent, such that the agent is expressed in the target cell.

The agent may be introduced into the target cell before the vector, at substantially the same time as the vector, or after the vector. When the agent is introduced after the vector, it will typically be introduced within a month, e.g. within 2 weeks, within 1 week, within 1 day, within 12 hours, or within 1 hour of the vector. It may be introduced periodically, e.g. at repeated intervals of 1 day to 1 month, e.g. at intervals of 1 day to 14 days, e.g. at intervals of 5 to 10 days, for an indefinite period of time.

Expression of the agent may be inducible. For example, the gene encoding the agent may comprise an inducible promoter so that transcription of the agent requires the cell to be contacted with a transcriptional inducer. The inducer may be an antibiotic for example, such as doxycycline or tetracycline. Inducible promoters which are responsive to such antibiotics are well known to the skilled person.

Alternatively, the agent may be expressed in a functionally inactive form which requires the cell to be contacted with a functional inducer in order to restore function. For example, the agent may be expressed as two or more separate protein moieties which require the presence of a functional inducer in order to associate into a functional form. Each of the component agent moieties may be expressed as a fusion with a partner protein, wherein the partner proteins associate on contact with the functional inducer. For example, the TEV protease (TEVp) can be expressed as two separate subunits each fused to heterologous protein moieties (FRB and FKBP) which associate only in the presence of rapamycin (a so-called "SPLIT-TEV" system) (See Gray et al. (2010) Activation of Specific Apoptotic Caspases with an Engineered Small-Molecule-Activated Protease, Cell 142(4): 637-646.). Other pairs of fusion partners may also be used, which have different requirements for association.

In some embodiments, the agent may be encoded by the vector genome itself, or in the genome of the target cell. Thus, either the vector genome or the target cell may comprise one or more genes encoding the activating agent or inhibitory agent, wherein expression or function of the agent is inducible. In such circumstances, the method does not require the target cell to be contacted with the activating agent or inhibitory agent, but simply requires the target cell to be contacted with the inducer (of expression or function).

The method may therefore include the step of inducing expression and/or function of the agent in the target cell, typically by contacting the target cell with the inducer.

The target cell may be contacted with the inducer periodically, e.g. at repeated intervals of 1 day to 1 month, e.g. at intervals of 1 day to 14 days, e.g. at intervals of 5 to 10 days, for an indefinite period of time.

In some embodiments, the vector genome does not comprise a gene encoding an envelope protein. Thus, the method may (additionally or alternatively) comprise the step of introducing into the target cell a nucleic acid construct comprising a gene encoding an envelope protein, such that the envelope protein is expressed in the target cell and incorporated into the plasma membrane. The envelope protein may be introduced into the target cell before the vector, at substantially the same time as the vector, or after the vector. When the envelope protein is introduced after the vector, it will typically be introduced within a month, e.g. within 14 days, within 7 days, within 1 day, within 12 hours, or within 1 hour of the vector.

Expression of the envelope protein may be inducible. For example, the gene encoding the envelope protein may comprise an inducible promoter so that transcription of the envelope protein requires the cell to be contacted with a transcriptional inducer.

The nucleic acid containing the gene encoding the inhibitory or activating agent, and/or the envelope protein, may be delivered to the target cell by any appropriate means. For example, each nucleic acid may independently be introduced as DNA or as RNA, as naked nucleic acid, in association with a carrier such as a polymer or lipid (e.g. as a complex with a carrier), in encapsulated form (e.g. encapsulated in a liposome) or via a viral vector. Suitable viral vectors include retroviral vectors (including lentiviral vectors), adenoviral vectors, and adeno-associated virus (AAV) vectors. AAV vectors may be particularly suitable.

The genes encoding the agent and the envelope protein may be delivered separately or together, e.g. as part of the same nucleic acid construct.

A viral vector having an inhibitory modulator protein may find particular use as an immunostimulatory agent, e.g. as a vaccine, against the native form of the same virus. Delivery of the vector to a recipient will result in replication of the virus only in cells which also receive the activating agent. Progeny virions may be formed and released from such infected cells. However, they will be unable to replicate further in cells which do not receive the activating agent. Thus co-administration of the vector and the activating agent, to particular selected cells, may result in a short controlled cycle of viral replication and release, stimulating the immune system and priming it to recognise the virus.

The viral vector may be otherwise attenuated to reduce any risk to the recipient. Thus it may comprise one or more further mutations to reduce or eliminate infectivity or virulence.

Release of progeny virions may be useful to simulate an antibody response against the native virus.

In order to produce and release progeny virions, the viral vector must encode an envelope protein, or an envelope protein must be supplied separately in trans to the infected cells if the vector lacks an envelope protein. Use of a vector lacking an envelope protein may represent a useful safety measure.

If the vector lacks an envelope protein, and no envelope protein is supplied in trans, there may still be sufficient protein expression in the presence of the activating agent to result in display of viral antigens via the recipient cell's MHC molecules (especially MHC I), and consequent stimulation of a T cell response (especially a CTL response) against the virus.

Nevertheless, use of a vector encoding an envelope protein may still be desirable in many circumstances.

The vectors of the invention find particular use in gene delivery to neural cells, especially when based on rabies virus or vesicular stomatitis virus. Use of G-deleted rabies virus is well known for monosynaptic circuit tracing in both the central and peripheral nervous system. However, current methods of monosynaptic circuit tracing have limited use because the labelled cells typically only remain viable for 1-2 weeks because of the accumulation of viral protein within the cell. The present vectors provide the capacity to genetically label neural cells without affecting viability.

The invention further provides a kit comprising a vector genome of the invention and (a) a cognate activating or inhibitory agent, or a nucleic acid encoding a cognate activating or inhibitory agent, and/or (b) a nucleic acid encoding an envelope protein.

The kit may comprise a system for delivery of the nucleic acid, such as a vector as described elsewhere. The same system may be used to deliver both the cognate survival factor and the envelope protein as described above.

The invention further provides a composition comprising a vector virion of the invention, optionally admixed with an excipient or carrier. The composition may be a pharmaceutical composition and the carrier may be a pharmaceutically acceptable carrier.

Mononegavirales infect diverse types of cell including plant, insect, fish and mammalian cells. In principle, it is believed that the present invention can be applied to any type of mononegavirus because they conform to a similar pattern of genomic organisation and rely on a similar coupled system of transcription and replication. Rhabdoviruses may be particularly apt.

The vectors of the invention may find particular use in the rhabdoviral genera and species which infect mammalian cells, especially lyssaviruses, such as the rabies virus (Rabies lyssavirus; RABV) and vesiculoviruses, such as vesicular stomatitis virus (VSV). Rabies virus has a particular tropism for neurons, which makes it a valuable candidate for gene delivery to neural tissue.

When the vector is based on a rabies virus, any appropriate strain may be used, including CVS (Challenge virus standard) and variants thereof such as CVS-N2c, PV4 (Pasteur virus), PM (Pitman-Moore), Flury-LEP (low egg passage), Flury-HEP (high egg passage), ERA and SAD (Street-Alabama Dufferin). The CVS-N2c strain is described in reference 25 and a full genome sequence is available under GenBank accession no. HM535790, version HM535790.1, 29 Dec. 2010.

Thus, the target cell type may be from a primate (e.g. Old World monkey, New World monkey, ape or human), rodent (e.g. mouse or rat), canine (e.g. domestic dog), feline (e.g. domestic cat), equine (e.g. horse), bovine (e.g. cow), caprine (e.g. goat), ovine (e.g. sheep) or lagomorph (e.g. rabbit).

The target cell type may be any desired cell type. In some examples, it may be a neural cell, e.g. a neuron or glial cell. The neural cell may be part of the peripheral or central nervous system.

Figure 1:
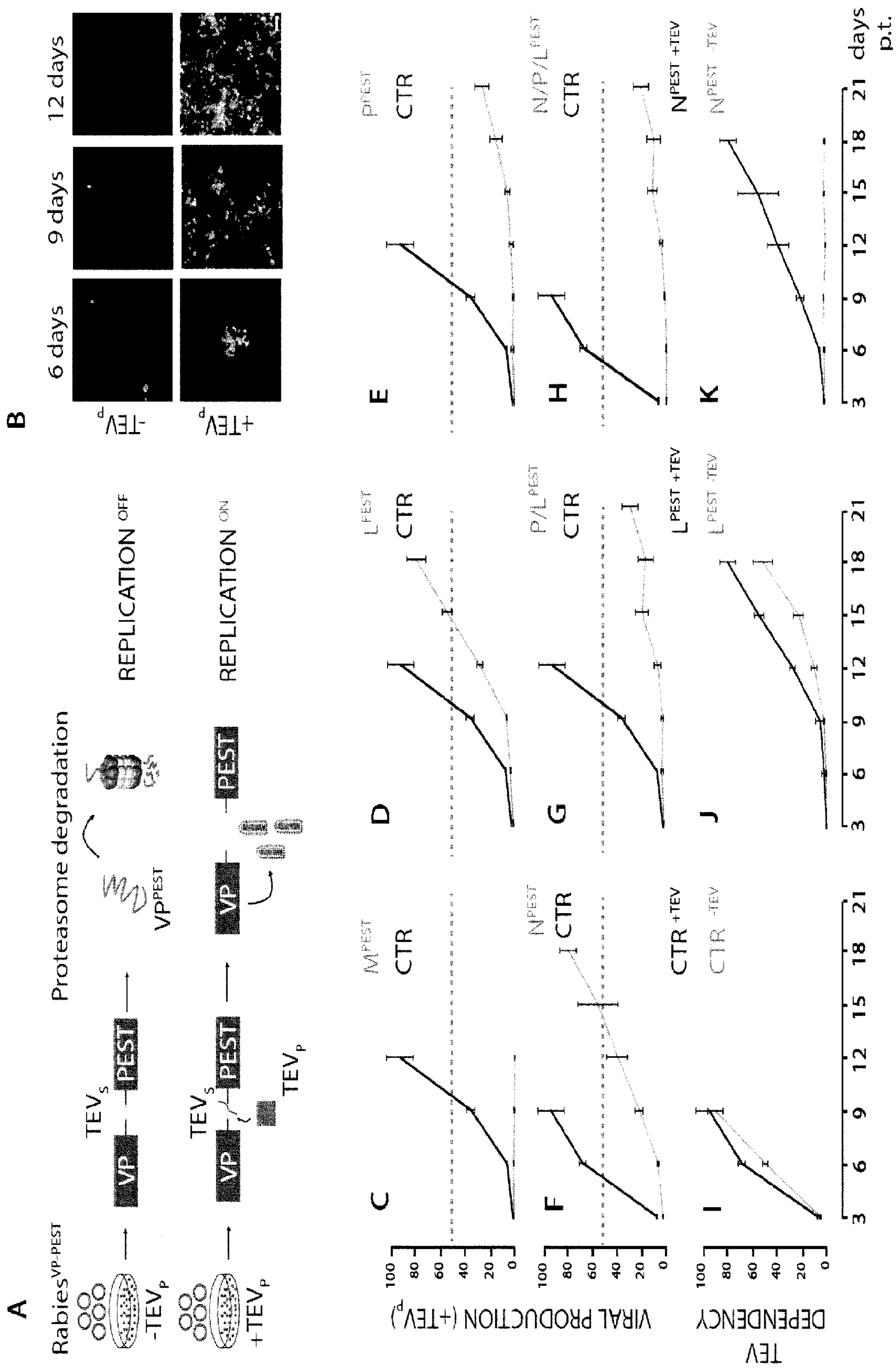
FIG. 1.

Screening viral amplification efficiency after systematic proteasome targeting of viral proteins. (A) Reversible viral protein destabilization via proteasome targeting PEST domain. (B) $TEV_P$-dependent viral amplification in HEKGG and HEKTGG. Scale bar: 100 μm. (C-H) Quantification of amplification efficiency for all recombinant Rabies constructs (magenta) and Control Rabies (cyan) (mean±SD; dashed line shows threshold level). (I-K) Quantification of amplification efficiency in HEKTGG (cyan, +TEV) and HEGG (magenta, −TEV). x-axis, days post-transfection (p.t.), y-axis amplification efficiency.

FIG. 2.

Absence of cytotoxicity in vivo. (A) SiR life cycle. (B) SiR expression cassette and experimental procedure. (C-E") Confocal images of hippocampal sections of Rosa-LoxP-STOP-LoxP-YFP mice infected with $SiR^{CRE\text{-}mCherry}$ and imaged at 1-3-8 weeks p.i. Scale bar: 25 μm. (F) Number of YFP and mCherry positive neurons at 1-2-3 and 8 weeks normalized to 1 week time-point (mean±SEM). (G) Levels of Viral RNA (magenta) and endogenous YFP expression (cyan) normalized to 1-week RNA level (mean±SEM)

FIG. 3.

SiR transsynaptic and retrograde spread. (A) AAV-TVAmCherry-GLY was injected in CA1 of Rosa-LoxSTOPLox-YFP mice and the TVA expressing neurons were specifically targeted with an EnVA pseudotyped $SiR^{CRE}$ 2 weeks later. (A') In the site of injection $YFP^{ON}$/$mCherry^{ON}$ starting neurons are detected (arrowheads) and (A"-A'") the transsynaptic jump of SiR virus permanently labeled neurons in CA3 and lateral enthorinal cortex (LEC) with YFP expression. Scale bar: 25 μm. (B-B") Confocal images of CA1 pyramidal neurons infected with AAV-TVAmCherry-GLY and $SiR^{CRE}$ at 3 weeks p.i. Scale bar: 10 μm. (C-C") Retrograde tracing of neurons from CA3 and LEC projecting to CA1 by $SiR^{mCherry}$ injection of CA1 of the hippocampus. (D) V1 cortical neurons infected by SiR injection in the superficial layers of the Superior Colliculus (SC). Scale bar: 25 μm.

FIG. 4.

SiR infection has no long-term impact on neuronal physiology. (A-B) Membrane potential response to steps of positive and negative current of a CA1 pyramidal neuron 1 week post-infection (p.i.) and 8 weeks p.i. (C) Input resistance, (D) resting membrane potential and action potential (AP) threshold, (E) AP amplitude and width, (F) firing frequency at increasing steps of positive current for neurons 1 week p.i. (n=10, magenta) and 8 weeks p. i. (n=8, cyan) (mean±SEM).

(G) Membrane potential response to a 0.2 ms blue-light pulse of increasing intensity (by 1% in each sweep until spiking; 0% lighter grey, to 9%, black) of $SiR^{CRE-mcherry}$ infected CA1 neuron expressing ChR2 (1 week p.i.). Insert, LED power delivered for each sweep. (H, I) Membrane potential response to a 800 ms light-pulse (2.17 mW) and to forty 1.5 ms long light-pulses at 20 Hz recorded from the same neuron. (J) Action potentials success rate following 40 light-stimulations at increasing frequencies, 1 (magenta) and 8 (cyan) weeks p.i. (K) Light-evoked EPSPs recorded in non-ChR2-expressing neurons blocked by DNQX (20 μM). Average traces for both conditions are shown in black. * $P<0.05$.

FIG. 5.

Unaltered orientation tuning responses of SiR traced V1 neurons. (A) Schematic of $SiR^{CRE}$ and AAV-GCaMP6s injection in Rosa-LoxP-STOP-LoxP-tdTomato mice in V2 and V1 respectively. (B-B") Two-photon maximal projection of V1 neurons after $SiR^{CRE}$ injection. In grey neurons expressing GCaMP6s (B), in magenta neurons expressing tdTomato (B') and in the merge neurons expressing both (B", merge). Scale bar: 50 μm. (C) Schematic of visual stimulation set up. (D) Outline of the active ROIs from the same field of view showed in panel B. (E) Representative $Ca^{2+}$ traces of GCaMP6s (cyan) and GCaMP6s-tdTomato (magenta) neurons. Scale bars: 200 s, 20% $dF/F_0$. (F) Mean percentage of active neurons after 4 weeks from SiR injection (n=122 GCaMP6 neurons (cyan), n=59 GCaMP6s and GCaMP6s-tdTomato neurons (magenta)). (G) Changes in fluorescence over time reflecting visual responses to drifting gratings at the preferred direction of each neuron. (H) Example of tuning curve of V1 infected neurons. Scale bars: 5 s, 10% $dF/F_0$.

FIG. 6.

Testing cytotoxicity of $\Delta G\text{-}N^{PEST}Rabies^{SPLIT-TEV-mCherry}$ in vitro and in vivo. (A) hESCs derived neurons were infected with $AG\text{-}N^{PEST}Rabies^{SPLIT-TEV-mcherry}$ and imaged longitudinally over 16 days. (B-B") $\Delta G\text{-}N^{PEST}$ $Rabies^{SPLIT-TEV-mcherry}$ and B19 ΔG-Rabies Control (C-C") infected hESCs derived neurons imaged at 4-10 and 16 days post-infection (p.i.). (D) Percentage of infected cells after administration of CTR ΔG-Rabies or $\Delta G\text{-}N^{PEST}$ $Rabies^{SPLIT-TEV-mcherry}$ in presence or absence of Rapamycin after 4-10 and 16 days normalized to day 4 time-point (mean±SEM). (E) mCherry signal intensity of $\Delta G\text{-}N^{PEST}Rabies^{SPLIT-TEV-mCherry}$ and ΔG-Rabies infected neurons normalized to day 4 time-point (mean±SEM., scale as in D). Scale bar: 50 μm. (F-G") Section of hippocampus infected in vivo with either AG Rabies (cyan) or $\Delta G\text{-}N^{PEST}$ $Rabies^{SPLIT-TEV-CRE}$ (magenta, G-G') at 1, 2 or 3 weeks p.i. Scale bar: 50 μm (H) Percentage of infected neurons at 1, 2 or 3 weeks p.i. of AG Rabies (black) or $\Delta G\text{-}N^{PEST}$ $Rabies^{SPLIT-TEV-CRE}$ (grey) in hippocampus normalized to day 7 time-point (mean±SEM).

FIG. 7.

Rapamycin induced Split TEV reconstitution and cleavage of the PEST domain in HEK cells. (A) Strategy for the pharmacological stabilization of the tagged viral protein. Rapamycin induces the dimerization of the Split TEV proteins which cleave the degron domain rescuing the viral proteins. (B) Split TEV rapamycin dose response in HEK. The TEV dependent cleavage of a TEV reporter increase with incremental concentration of rapamycin (0-10-50 nM). (C) The Split TEV cassette was cloned into the glycoprotein locus in the Rabies genome. A clear rapamycin dependent TEV activity was observed in HEK293T infected with the Spit TEV expressing Rabies and transfected with a TEV reporter.

FIG. 8.

Short-term $SiR^{mcherry}$ kinetics in vivo. (A) $SiR^{mcherry}$ cassette design. (B) SiR mCherry-CRE injection in CA1 of Rosa-LoxSTOPLox-YFP mice. (C-E") Confocal images of CA1 pyramidal neurons infected with $SiR^{mcherry-CRE}$ at 3-6 and 9 days p.i. Scale bar: 25 μm. (F-F") Percentage of $YFP^{ON}$, $mCherry^{ON}$ and $YFP^{ON}mCherry^{ON}$ neurons at 3-6 and 9 days p.i.

FIG. 9

Pharmacological reactivation of SiR. (A) Design of the doxycycline inducible AAV. The rTTA trans-activator is constitutive expressed by the virus and in presence of doxycycline it drives the TEV protease expression. (B) Diagram of AAV-TRE-TEV injection in the hippocampus of Rosa-LoxP-STOP-LoxP-YFP mice follow by $SiR^{CRE-mCherry}$ in the same region 1 week after and Doxycycline administration. (C-F) Hippocampal pyramidal neurons infected with SiR and AAV-TRE-TEV, reactivated with Doxycycline at 2 or 3 weeks p.i. Scale bar: 50 μm. (G) Quantification of $mCherry^{ON}$ neurons over the total $YFP^{ON}$ infected neurons.

FIG. 10.

ΔG-Rabies induced mortality in cortex and hippocampus. (A-A") Confocal images of cortical neurons and (B-B") CA1 pyramidal neurons infected with $\Delta G\text{-}Rabies^{GFP}$ at 1, 2 and 3 weeks p.i. Scale bar: 50 μm. (C) Percentage of infected neurons at 1, 2 or 3 weeks p.i. of ΔG Rabies in cortex (black) or hippocampus (grey) normalized to 1 week time-point (mean±SEM) (hippocampus, 92±3% cell death at 2 weeks, n=3 per time-point, one-way ANOVA, F=101, $P=2.4\times10^{-5}$; cortex 85±2% cell death at 3 weeks, n=3 per time-point, one-way ANOVA, F=17, $P=3.2\times10^{-3}$)

FIG. 11.

(A) Map of plasmid encoding SiR CRE-mCherryPEST vector genome;

(B) Sequence of the plasmid shown in (A) T7 promoter sequence is shown with double underlining (SEQ ID NO: 19). Open reading frames are shown with single underlining and represent in order N-TEV-PEST, P, M, iCRE-2A-mCherryPEST and L proteins.

FIG. 12.

Map of plasmid encoding SiR vector having multiple cloning site in place of gene for envelope (G) protein.

FIG. 13.

Figure 12:
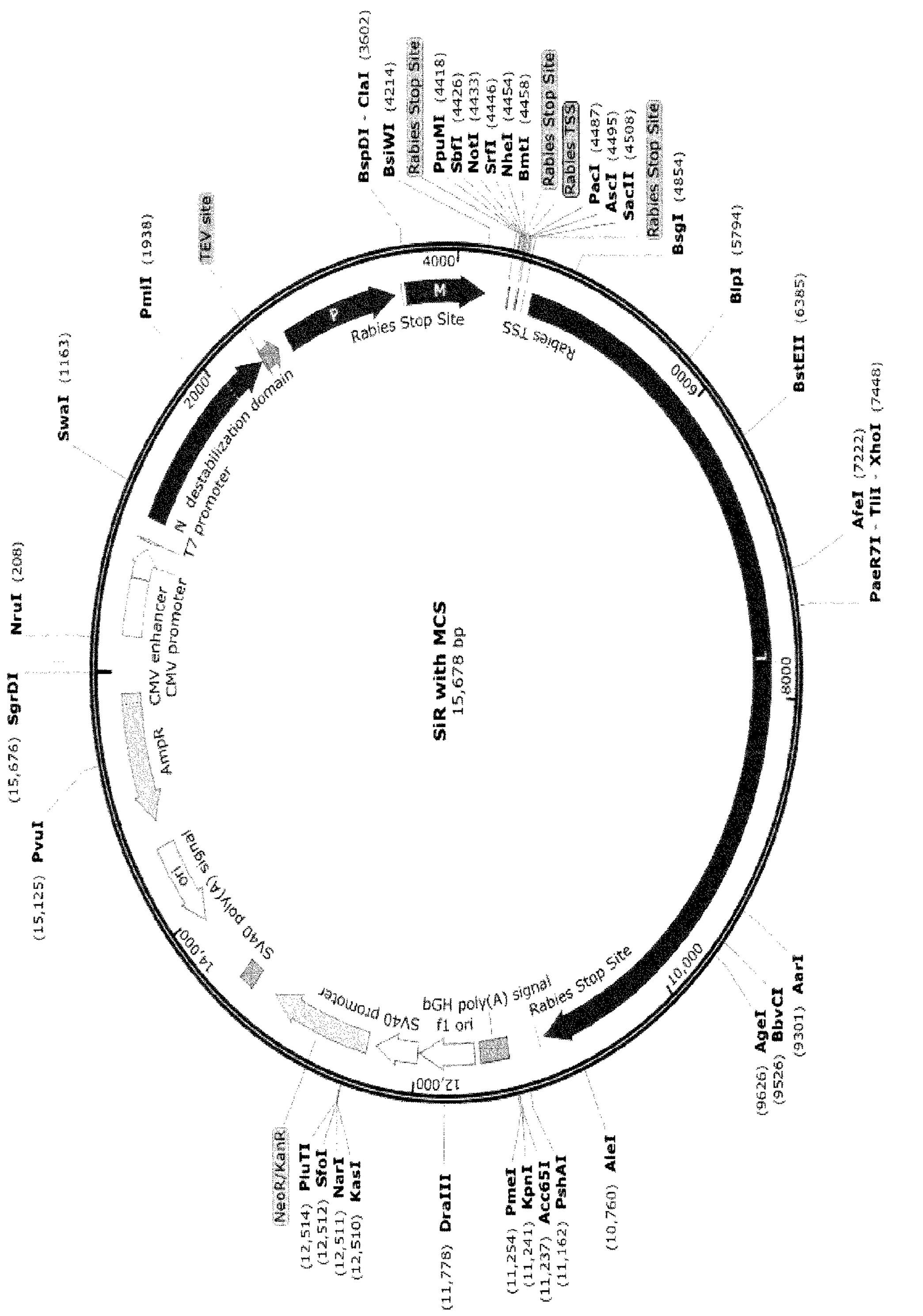

Full sequence of plasmid illustrated in FIG. 12 (SEQ ID NO: 20). Backbone plasmid (i.e. non-SiR) sequence shown in upper case with shading. Vector open reading frames are underlined, in order (from 5'-3') N-TEV-PEST protein, P protein, M protein, L protein. Multiple cloning sites (SbfI-NheI and PacI-AscI) shown in italic upper case. Within the N-TEV-PEST protein, N sequence is shown in lower case regular font, TEV cleavage site in upper case italics, PEST sequence in upper case double-underlined, and linker peptide sequences in lower case italics.

FIG. 14.

Sequence of negative-sense vector RNA genome (SEQ ID NO: 21) obtained by transcription from the plasmid illustrated in FIGS. 12 and 13.

DETAILED DESCRIPTION OF THE INVENTION

Mononegavirales

The order Mononegavirales contains the families Bornaviridae, Filoviridae, Mymonaviridae, Nyamiviridae, Paramyxoviridae, Pneumoviridae, Rhabdoviridae and Sunviridae, as well as five unclassified genera Anphevirus, Arlivirus, Chengtivirus, Crustavirus, and Wastrivirus. Genera and species within those families are shown in the table below. Asterisks "*" in the following table denote type species.

Order Mononegavirales: families, genera, species, and viruses

| Family | Genus | Species | Virus (Abbreviation) |
|---|---|---|---|
| Bornaviridae | Bornavirus | Elapid 1 bornavirus | Loveridge's garter snake virus 1 (LGSV-1) |
| | | Mammalian 1 bornavirus* | Borna disease virus 1 (BoDV-1) |
| | | | Borna disease virus 2 (BoDV-2) |
| | | Passeriform 1 bornavirus | canary bornavirus 1 (CnBV-1) |
| | | | canary bornavirus 2 (CnBV-2) |
| | | | canary bornavirus 3 (CnBV-3)) |
| | | Passeriform 2 bornavirus | estrildid finch bornavirus 1 (EsBV-1) |
| | | Psittaciform 1 bornavirus | parrot bornavirus 1 (PaBV-1) |
| | | | parrot bornavirus 2 (PaBV-2) |
| | | | parrot bornavirus 3 (PaBV-3) |
| | | | parrot bornavirus 4 (PaBV-4) |
| | | | parrot bornavirus 7 (PaBV-7) |
| | | Psittaciform 2 bornavirus | parrot bornavirus 5 (PaBV-5) |
| | | Waterbird 1 bornavirus | aquatic bird bornavirus 1 (ABBV-1) |
| | | | aquatic bird bornavirus 2 (ABBV-2) |
| Filoviridae | Cuevavirus | Lloviu cuevavirus* | Lloviu virus (LLOV) |
| | Ebolavirus | Bundibugyo ebolavirus | Bundibugyo virus (BDBV) |
| | | Reston ebolavirus | Reston virus (RESTV) |
| | | Sudan ebolavirus | Sudan virus (SUDV) |
| | | Taï Forest ebolavirus | Taï Forest virus (TAFV) |
| | | Zaire ebolavirus* | Ebola virus (EBOV) |
| | Marburgvirus | Marburg marburgvirus* | Marburg virus (MARV) |
| | | | Ravn virus (RAVV) |
| Mymonaviridae | Sclerotimonavirus | Sclerotinia sclerotimonavirus* | Sclerotinia sclerotiorum negative-stranded RNA virus 1 (SsNSRV-1) |
| Nyamiviridae | Nyavirus | Midway nyavirus | Midway virus (MIDWV) |
| | | Nyamanini nyavirus* | Nyamanini virus (NYMV) |

-continued

| Order Mononegavirales: families, genera, species, and viruses | | | |
|---|---|---|---|
| Family | Genus | Species | Virus (Abbreviation) |
| | | Sierra Nevada nyavirus | Sierra Nevada virus (SNVV) |
| | Socyvirus | Soybean cyst nematode socyvirus* | soybean cyst nematode virus 1 (SbCNV-1) |
| Paramyxoviridae | Aquaparamyxovirus | Atlantic salmon paramyxovirus* | Atlantic salmon paramyxovirus (AsaPV) |
| | Avulavirus | Avian paramyxovirus 2 | avian paramyxovirus 2 (APMV-2) |
| | | Avian paramyxovirus 3 | avian paramyxovirus 3 (APMV-3) |
| | | Avian paramyxovirus 4 | avian paramyxovirus 4 (APMV-4) |
| | | Avian paramyxovirus 5 | avian paramyxovirus 5 (APMV-5) |
| | | Avian paramyxovirus 6 | avian paramyxovirus 6 (APMV-6) |
| | | Avian paramyxovirus 7 | avian paramyxovirus 7 (APMV-7) |
| | | Avian paramyxovirus 8 | avian paramyxovirus 8 (APMV-8) |
| | | Avian paramyxovirus 9 | avian paramyxovirus 9 (APMV-9) |
| | | Avian paramyxovirus 10 | avian paramyxovirus 10 (APMV-10) |
| | | Avian paramyxovirus 11 | avian paramyxovirus 11 (APMV-11) |
| | | Avian paramyxovirus 12 | avian paramyxovirus 12 (APMV-12) |
| | | Newcastle disease virus* | avian paramyxovirus 1 (APMV-1) |
| | Ferlavirus | Fer-de-Lance paramyxovirus* | Fer-de-Lance virus (FDLV) |
| | Henipavirus | Cedar henipavirus | Cedar virus (CedV) |
| | | Ghanaian bat henipavirus | Kumasi virus (KV) |
| | | Hendra virus* | Hendra virus (HeV) |
| | | Mojiang henipavirus | Mòjiāng virus (MojV) |
| | | Nipah virus | Nipah virus (NiV) |
| | Morbillivirus | Canine distemper virus | canine distemper virus (CDV) |
| | | Cetacean morbillivirus | cetacean morbillivirus (CeMV) |
| | | Feline morbillivirus | feline morbillivirus (FeMV) |
| | | Measles virus* | measles virus (MeV) |
| | | Peste-des-petits-ruminants virus | peste-des-petits-ruminants virus (PPRV) |
| | | Phocine distemper virus | phocine distemper virus (PDV) |
| | | Rinderpest virus | rinderpest virus (RPV) |

-continued

| Order Mononegavirales: families, genera, species, and viruses | | | |
|---|---|---|---|
| Family | Genus | Species | Virus (Abbreviation) |
| | Respirovirus | Bovine parainfluenza virus 3 | bovine parainfluenza virus 3 (BPIV-3) |
| | | Human parainfluenza virus 1 | human parainfluenza virus 1 (HPIV-1) |
| | | Human parainfluenza virus 3 | human parainfluenza virus 3 (HPIV-3) |
| | | Porcine parainfluenzavirus 1 | porcine parainfluenza virus 1 (PPIV-1) |
| | | Sendai virus* | Sendai virus (SeV) |
| | Rubulavirus | Human parainfluenza virus 2 | human parainfluenza virus 2 (HPIV-2) |
| | | Human parainfluenza virus 4 | human parainfluenza virus 4a (HPIV-4a) |
| | | | human parainfluenza virus 4b (HPIV-4b) |
| | | Mapuera virus | Mapuera virus (MapV) |
| | | Mumps virus* | mumps virus (MuV) |
| | | | bat mumps virus (BMV) |
| | | Parainfluenza virus 5 | parainfluenza virus 5 (PIV-5) |
| | | Porcine rubulavirus | La Piedad Michoacán Mexico virus (LPMV) |
| | | Simian virus 41 | simian virus 41 (SV-41) |
| Pneumoviridae | Metapneumovirus | Avian metapneumovirus* | avian metapneumovirus (AMPV) |
| | | Human metapneumovirus | human metapneumovirus (HMPV) |
| | Orthopneumovirus | Bovine respiratory syncytial virus | bovine respiratory syncytial virus (BRSV) |
| | | Human respiratory syncytial virus* | human respiratory syncytial virus A2 (HRSV-A2) |
| | | | human respiratory syncytial virus B1 (HRSV-B1) |
| | | | human respiratory syncytial virus S2 (HRSV-S2) |
| | | Murine pneumonia virus | murine pneumonia virus (MPV) |
| Rhabdoviridae | Cytorhabdovirus | Alfalfa dwarf cytorhabdovirus | alfalfa dwarf virus (ADV) |
| | | Barley yellow striate mosaic cytorhabdovirus | barley yellow striate mosaic virus (BYSMV) |
| | | Broccoli necrotic yellows cytorhabdovirus | broccoli necrotic yellows virus (BNYV) |
| | | Festuca leaf streak cytorhabdovirus | festuca leaf streak virus (FLSV) |

-continued

| Order Mononegavirales: families, genera, species, and viruses | | | |
|---|---|---|---|
| Family | Genus | Species | Virus (Abbreviation) |
| | | Lettuce necrotic yellows cytorhabdovirus* | lettuce necrotic yellows virus (LNYV) |
| | | Lettuce yellow mottle cytorhabdovirus | lettuce yellow mottle virus (LYMoV) |
| | | Northern cereal mosaic cytorhabdovirus | northern cereal mosaic virus (NCMV) |
| | | Sonchus cytorhabdovirus | sonchus virus (SonV) |
| | | Strawberry crinkle cytorhabdovirus | strawberry crinkle virus (SCV) |
| | | Wheat American striate mosaic cytorhabdovirus | wheat American striate mosaic virus (WASMV) |
| | Dichorhavirus | Coffee ringspot dichorhavirus | coffee ringspot virus (CoRSV) |
| | | Orchid fleck dichorhavirus* | orchid fleck virus (OFV) |
| | Ephemerovirus | Adelaide River ephemerovirus | Adelaide River virus (ARV) |
| | | Berrimah ephemerovirus | Berrimah virus (BRMV) |
| | | Bovine fever ephemerovirus* | bovine ephemeral fever virus (BEFV) |
| | | Kotonkan ephemerovirus | kotonkan virus (KOTV) |
| | | Obodhiang ephemerovirus | Obodhiang virus (OBOV) |
| | Lyssavirus | Aravan lyssavirus | Aravan virus (ARAV) |
| | | Australian bat lyssavirus | Australian bat lyssavirus (ABLV) |
| | | Bokeloh bat lyssavirus | Bokeloh bat lyssavirus (BBLV) |
| | | Duvenhage lyssavirus | Duvenhage virus (DUVV) |
| | | European bat 1 lyssavirus | European bat lyssavirus 1 (EBLV-1) |
| | | European bat 2 lyssavirus | European bat lyssavirus 2 (EBLV-2) |
| | | Ikoma lyssavirus | Ikoma lyssavirus (IKOV) |
| | | Irkut lyssavirus | Irkut virus (IRKV) |
| | | Khujand lyssavirus | Khujand virus (KHUV) |
| | | Lagos bat lyssavirus | Lagos bat virus (LBV) |
| | | Mokola lyssavirus | Mokola virus (MOKV) |
| | | Rabies lyssavirus* | rabies virus (RABV) |
| | | Shimoni bat lyssavirus | Shimoni bat virus (SHIBV) |
| | | West Caucasian bat lyssavirus | West Caucasian bat virus (WCBV) |
| | Novirhabdovirus | Hirame novirhabdovirus | Hirame rhabdovirus (HIRV) |
| | | Oncorhynchus 1 novirhabdovirus* | infectious hematopoietic necrosis virus (IHNV) |
| | | Oncorhynchus 2 novirhabdovirus | viral hemorrhagic septicemia virus (VHSV) |

-continued

| Order Mononegavirales: families, genera, species, and viruses | | | |
|---|---|---|---|
| Family | Genus | Species | Virus (Abbreviation) |
| | | Snakehead novirhabdovirus | snakehead rhabdovirus (SHRV) |
| | Nucleorhabdovirus | Datura yellow vein nucleorhabdovirus | datura yellow vein virus (DYVV) |
| | | Eggplant mottled dwarf nucleorhabdovirus | eggplant mottled dwarf virus (EMDV) |
| | | Maize fine streak nucleorhabdovirus | maize fine streak virus (MSFV) |
| | | Maize Iranian mosaic nucleorhabdovirus | maize Iranian mosaic virus (MIMV) |
| | | Maize mosaic nucleorhabdovirus | maize mosaic virus (MMV) |
| | | Potato yellow dwarf nucleorhabdovirus* | potato yellow dwarf virus (PYDV) |
| | | Rice yellow stunt nucleorhabdovirus | rice yellow stunt virus (RYSV) |
| | | | rice transitory yellowing virus (RTYV) |
| | | Sonchus yellow net nucleorhabdovirus | sonchus yellow net virus (SYNV) |
| | | Sowthistle yellow vein nucleorhabdovirus | sowthistle yellow vein virus (SYVV) |
| | | Taro vein chlorosis nucleorhabdovirus | taro vein chlorosis virus (TaVCV) |
| | Perhabdovirus | Anguillid perhabdovirus | eel virus European X (EVEX) |
| | | Perch perhabdovirus* | perch rhabdovirus (PRV) |
| | | Sea trout perhabdovirus | lake trout rhabdovirus (LTRV) |
| | Sigmavirus | Drosophila affinis sigmavirus | Drosophila affinis sigmavirus (DAffSV) |
| | | Drosophila ananassae sigmavirus | Drosophila ananassae sigmavirus (DAnaSV) |
| | | Drosophila immigrans sigmavirus | Drosophila immigrans sigmavirus (DImmSV) |
| | | Drosophila melanogaster sigmavirus* | Drosophila melanogaster sigmavirus (DMelSV) |
| | | Drosophila obscura sigmavirus | Drosophila obscura sigmavirus (DObsSV) |
| | | Drosophila tristis sigmavirus | Drosophila tristis sigmavirus (DTriSV) |
| | | Muscina stabulans sigmavirus | Muscina stabulans sigmavirus (MStaSV) |
| | Sprivivirus | Carp sprivivirus* | spring viremia of carp virus (SVCV) |

-continued

| Order Mononegavirales: families, genera, species, and viruses | | | |
|---|---|---|---|
| Family | Genus | Species | Virus (Abbreviation) |
| | | Pike fry sprivivirus | grass carp rhabdovirus (GrCRV)<br>pike fry rhabdovirus (PFRV)<br>Tench rhabdovirus (TenRV) |
| | Tibrovirus | Coastal Plains tibrovirus | Coastal Plains virus (CPV) |
| | | Tibrogargan tibrovirus* | Bivens Arm virus (BAV)<br>Tibrogargan virus (TIBV) |
| | Tupavirus | Durham tupavirus* | Durham virus (DURV) |
| | | Tupaia tupavirus | tupaia virus (TUPV) |
| | Varicosavirus | Lettuce big-vein associated varicosavirus* | lettuce big-vein associated virus (LBVaV) |
| | Vesiculovirus | Alagoas vesiculovirus | vesicular stomatitis Alagoas virus (VSAV) |
| | | Carajas vesiculovirus | Carajás virus (CJSV) |
| | | Chandipura vesiculovirus | Chandipura virus (CHPV) |
| | | Cocal vesiculovirus | Cocal virus (COCV) |
| | | Indiana vesiculovirus* | vesicular stomatitis Indiana virus (VSIV) |
| | | Isfahan vesiculovirus | Isfahan virus (ISFV) |
| | | Maraba vesiculovirus | Maraba virus (MARAV) |
| | | New Jersey vesiculovirus | vesicular stomatitis New Jersey virus (VSNJV) |
| | | Piry vesiculovirus | Piry virus (PIRYV) |
| | Unassigned | Flanders virus | Flanders virus (FLAV) |
| | | Ngaingan virus | Ngaingan virus (NGAV) |
| | | Wongabel virus | Wongabel virus (WONV) |
| Sunviridae | Sunshinevirus | Reptile sunshinevirus 1* | Sunshine Coast virus (SunCV) |
| Unassigned | Anphevirus | Xincheng anphevirus* | Xīnchéng mosquito virus (XcMV) |
| Unassigned | Arlivirus | Lishi arlivirus* | Líshí spider virus 2 (LsSV-2) |
| Unassigned | Chengtivirus | Tacheng chengtivirus* | Tăchéng tick virus 6 (TcTV-6) |
| Unassigned | Crustavirus | Wenzhou crustavirus* | Wēnzhōu crab virus 1 (WzCV-1) |
| Unassigned | Wastrivirus | Sanxia wastrivirus* | Sānxiá water strider virus 4 (SxWSV-4) |

For more detail, see "Taxonomy of the order Mononegavirales: update 2016", Afonso et al., Arch. Virol. (2016) 161:2351-2360.

The viruses within the order (referred to here as "mononegaviruses") are enveloped viruses possessing genomes of non-infectious, linear, single-stranded, negative sense RNA.

The majority of mononegaviruses have non-segmented genomes. Without wishing to be bound by theory, it is believed that the methods and compositions described in this specification are more applicable to non-segmented viruses than to segmented viruses.

The genome has inverse-complementary 3' and 5' termini and is not covalently linked to any proteins.

The genomes generally have a conserved layout of coding and non-coding elements in the order 3'UTR (untranslated region)-core protein-coding genes-envelope protein-coding gene(s)-polymerase-coding gene-5'UTR.

The core proteins encoded by the genome include the nucleoprotein (often designated "N" or "NP"), a protein which is often phosphorylated and so is referred to as a phosphoprotein (designated "P"), and a matrix protein ("M").

The polymerase is an RNA-dependent RNA polymerase and often the largest protein encoded by the virus and so may be referred to as the large (or "L") protein. The polymerase is relatively highly conserved within the order. The P protein may represent a co-factor for the L protein, i.e. the L and P proteins may be required to be present together for polymerase activity.

The terms N (or NP), P, M and L proteins are used in this specification to refer to any proteins which fulfil the corresponding roles in mononegaviruses, regardless of their normal designations.

The envelope protein is a transmembrane protein which may be glycosylated. In some mononegaviruses, it is therefore referred to as the glycoprotein (or "G" protein).

The virion comprises a helical ribonucleoprotein nucleocapsid, in which the genome is associated with the N, P and L proteins. This nucleocapsid is surrounded by the matrix and the membrane envelope layer.

Infection of a host cell results in release of the viral nucleocapsid into the cytosol, where transcription and replication take place via the RNA-dependent RNA polymerase.

All transcription takes place from a single promoter at the 3' end of the genome. After transcription of each gene, the polymerase either terminates or continues to the next gene downstream, yielding a gradient of mRNA production, with those genes closest to the 3' end of the genome being transcribed in the highest copy number, and increasingly fewer transcripts produced for the genes towards the 5' end. Typically each virus produces 5 to 10 different mRNAs. The level of the nucleoprotein (often designated "N" or "NP") determines the timing of a switch between mRNA generation and genome replication. Replication involves the production by the polymerase of full-length positive-sense antigenomes which are subsequently transcribed into full-length negative sense genome copies for packaging into virions.

The term "gene" in this specification is used to refer to a sequence in the vector genome which encodes an expression product and which directs expression of that expression product, typically under the control of the vector's promoter. The ultimate expression product may be an RNA (in which case expression requires only transcription from the vector genome) or a protein (in which case expression requires transcription into mRNA by viral proteins followed by translation into protein.

Features of Rhabdoviruses, and in particular of the rabies virus, are described in more detail below as illustrative examples of mononegaviral biology.

Rhabdoviruses typically have genomes of around 11-15 kb in length. They variously infect vertebrates (including mammals and fish), insects and plants.

The rabies genome has short non-coding regions at its termini, designated the 3' leader (le) and 5' trailer (tr), which respectively initiate and terminate genome transcription and replication. The very 3' and 5' ends are inversely complementary. The termini also contain promoter sequences for transcription and replication, and for encapsidation of genomic RNA.

The 5 structural genes are ordered (3' to 5') N (nucleoprotein), P (phosphoprotein), M (matrix), G (glycoprotein) and L (large), with short non-coding intergenic regions (IGRs). Each structural gene comprises a coding region flanked by a 3' transcription initiation signal (TIS) (consensus sequence 3'-U-U-G-U-R-R-n-G-A-5' and a 5' transcription termination polyadenylation (TTP) signal (consensus sequence 3'A/U-C-U-U-U-U-U-U-U-G-5') (SEQ ID NO: 1).

Infection is mediated by binding of the G protein to its receptor on the surface of the target cell. The virus is then internalised via the cell's endosomal transport pathway. The low pH in the endosome induces membrane fusion (between the endosomal membrane and the viral envelope), also mediated by the G protein, releasing the ribonucleoprotein complex into the cytoplasm.

Transcription of mRNA encoding viral protein then begins, mediated by the viral polymerase (comprising P and L proteins). Transcription is believed to proceed via a stop-start mechanism, beginning at the 3' end of the genome and progressing towards the 5' end, producing 6 consecutive transcripts, firstly of the leader RNA, and then each of the N, P, M, G and L genes in turn. The polymerase is believed to dissociate from the template at each stop signal and re-initiate poorly at the next start signal. This results in a gradient of mRNA production with the amount of leader transcript being greatest, followed by N, P, M, G and L transcripts.

Later in infection, the polymerase switches from mRNA production to replication of the viral genome, which proceeds via a full length positive sense RNA intermediate. Both the positive sense intermediate and the progeny negative sense viral genomes are packaged with protein N to form nucleoprotein complexes. The M protein plays a regulatory role in determining the timing of the switch between transcription and replication, as well as being involved in recruitment of RNP nucleocapsids to the host cell plasma membrane, association with glycoprotein G, and budding of the progeny virion particles from the cell.

For a review, including more detail about the roles and functions of the individual proteins, see Albertini et al., Rabies Virus Transcription and Replication, Advances in Virus Research 79, December 2011 (ISSN 0065-3527; DOI: 10.1016/B978-0-12-387040-7.00001-9).

An exemplary sequence of a rabies N protein is as follows:

```
MDADKIVFKVNNQVVSLKPEIIVDQYEYKYPAIKDLKKPCITLGKAPDL

NKAYKSVLSGMSAAKLNPDDVCSYLAAAMQFFEGTCPEDWTSYGIVIAR

KGDKITPGSLVEIKRTDVEGNWALTGGMELTRDPTVPEHASLVGLLLSL

YRLSKISGQNTGNYKTNIADRIEQIFETAPFVKIVEHHTLMTTHKMCAN

WSTIPNFRFLAGTYDMFFSRIEHLYSAIRVGTVVTAYEDCSGLVSFTGF

IKQINLTAREAILYFFHKNFEEEIRRMFEPGQETAVPHSYFIHFRSLGL

SGKSPYSSNAVGHVFNLIHFVGCYMGQVRSLNATVIAACAPHEMSVLGG

YLGEEFFGKGTFERREERDEKELQEYEAAELTKTDVALADDGTVNSDDE

DYFSGETRSPEAVYTRIMMNGGRLKRSHIRRYVSVSSNHQARPNSFAEF

LNKTYSSDS
```

An exemplary sequence of a rabies P protein is as follows:

MSKIFVNPSAIRAGLADLEMAEETVDLINRNIEDNQAHLQGEPIEVDNL
PEDMGRLHLDDGKSPNHGEIAKVGEGKYREDFQMDEGEDPSFLFQSYLE
NVGVQIVRQMRSGERFLKIWSQTVEEIISYVAVNFPNPPGKSSEDKSTQ
TTGRELKKETTPTPSQRESQSSKARMAAQIASGPPALEWSATNEEDDLS
VEAEIAHQIAESFSKKYKFPSRSSGILLYNFEQLKMNLDDIVKEAKNVP
GVTRLAHDGSKLPLRCVLGWVALANSKKFQLLVESDKLSKIMQDDLNRY
TSC

An exemplary sequence of a rabies M protein is as follows:

MNLLRKIVKNRRDEDTQKSSPASAPLDDDDLWLPPPEYVPLKELTGKKN
MRNFCINGRVKVCSPNGYSFRILRHILKSFDEIYSGNHRMIGLVKVVIG
LALSGSPVPEGLNWVYKLRRTFIFQWADSRGPLEGEELEYSQEITWDDD
TEFVGLQIRVIAKQCHIQGRVWCINMNPRACQLWSDMSLQTQRSEEDKD
SSLLLE

An exemplary sequence of a rabies L protein is as follows:

MLDPGEVYDDPIDPIELEAEPRGTPIVPNILRNSDYNLNSPLIEDPARL
MLEWLKTGNRPYRMTLTDNCSRSFRVLKDYFKKVDLGSLKVGGMAAQSM
ISLWLYGAHSESNRSRRCITDLAHFYSKSSPIEKLLNLTLGNRGLRIPP
EGVLSCLERVDYDNAFGRYLANTYSSYLFFHVITLYMNALDWDEEKTIL
ALWKDLTSVDIGKDLVKFKDQIWGLLIVTKDFVYSQSSNCLFDRNYTLM
LKDLFLSRFNSLMVLLSPPEPRYSDDLISQLCQLYIAGDQVLSMCGNSG
YEVIKILEPYVVNSLVQRAEKFRPLIHSLGDFPVFIKDKVSQLEETEGP
CARREFRALDQFDNIEDLVFVFGCYRHWGHPYIDYRKGLSKLYDQVHLK
KMIDKSYQECLASDLARRILRWGFDKYSKWYLDSRFLARDHPLTPYIKT
QTWPPKHIVDLVGDTWHKLPITQIFEIPESMDPSEILDDKSHSFTRTRL
ASWLSENRGGPVPSEKVIITALSKPPVNPREFLRSIDLGGLPDEDLIIG
LKPKERELKIEGRFFALMSWNLRLYFVITEKLLANYILPLFDALTMTDN
LNKVFKKLIDRVTGQGLLDYSRVTYAFHLDYEKWNNHQRLESTEDVFSV
LDQVFGLKRVFSRTHEFFQKAWIYYSDRSDLIGLREDQIYCLDASNGPT
CWNGQDGGLEGLRQKGWSLVSLLMIDRESQIRNTRTKILAQGDNQVLCP
TYMLSPGLSQEGLLYELERISRNALSIYRAVEEGASKLGLIIKKEETMC
SYDFLIYGKTPLFRGNILVPESKRWARVSCVSNDQIVNLANIMSTVSTN
ALTVAQHSQSLIKPMRDFLLMSVQAVEHYLLFSPILKGRVYKILSAEGE
SFLLAMSRIIYLDPSLGGISGMSLGRFHIRQFSDPVSEGLSFWREIWLS
SQESWIHALCQEAGNPDLGERTLESFTRLLEDPTTLNIRGGASPTILLK
DAIRKALYDEVDKVENSEFREAILLSKTHRDNFILFLISVEPLFPRFLS
ELFSSSFLGIPESIIGLIQNSRTIRRQFRKSLSKTLEESFYNSEIHGIS
RMTQTPQRVGGVWPCSSERADLLREISWGRKVVGTTVPHPSEMLGLLPK

-continued

SSISCTCGATGGGNPRVSVSVLPSFDQSFFSRGPLKGYLGSSTSMSTQL
FHAWEKVTNVHVVKRALSLKESINWEITRDSNLAQALIRNIMSLTGPDF
PLEEAPVFKRTGSALHRFKSARYSEGGYSSVCPNLLSHISVSTDTMSDL
TQDGKNYDFMFQPLMLYAQTWTSELVQRDTRLRDSTFHWHLRCNRCVRP
IDDVTLETSQIFEFPDVSKRISRMVSGAVPHFQRLPDIRLRPGDFESLS
GREKSHHIGSAQGLLYSILVAIHDSGYNDGTIFPVNIYGKVSPRDYLRG
LARGVLIGSSICFLTRMTNININRPLELVSGVISYILLRLDNHPSLYIM
LREPSLRGEIPSIPQKIPAAYPTTMKEGNRSILCYLQHVLRYEREIITA
SPENDWLWIFSDERSAKMTYLSLITYQSHLLLQRVERNLSKSMRDNLRQ
LSSLMRQVLGGHGEDTLESDDNIQRLLKDSLRRTRWVDQEVRHAARTMT
GDYSPNKKVSRKVGCSEWVCSAQQVAVSTSANPAPVSELDIRALSKRFQ
NPLISGLRVVQWATGAHYKLKPILDDLNVFPSLCLVVGDGSGGISRAVL
NMFPDAKLVFNSLLEVNDLMASGTHPLPPSAIMRGGNDIVSRVIDLDSI
WEKPSDLRNLATWKYFQSVQKQVNMSYDLIICDAEVTDIASINRITLLM
SDEALSIDGPLYLVFKTYGTMLVNPNYKAIQHLSRAFPSVTGFITQVTS
SFSSELYLRFSKRGKFFRDAEYLTSSTLREMSLVLFNCSSPKSEMQRAR
SLNYQDLVRGFPEEIISNPYNEMIITLIDSDVESFLVHKMVDDLELQRG
TLSKVAIIIAIMIVFSNRVFNVSKPLTDPSFYPPSDPKILRHFNICCST
MMYLSTALGDVPSFARLHDLYNRPITYYFRKQVIRGNVYLSWSWSNDTS
VFKRVACNSSLSLSSHWIRLIYKIVKTTRLVGSIKDLSREVERHLHRYN
RWITLEDIRSRSSLLDYSCL

Thus, when used in the vectors of the present invention, a rabies N protein may have the sequence shown above, or may have at least 70% identity thereto, e.g. at least 75%, at least 80%, at least 85%, at least 90%, at least 95%, at least 96%, at least 97%, at least 98%, or at least 99% identity thereto.

A rabies P protein may have the sequence shown above, or may have at least 70% identity thereto, e.g. at least 75%, at least 80%, at least 85%, at least 90%, at least 95%, at least 96%, at least 97%, at least 98%, or at least 99% identity thereto.

A rabies M protein may have the sequence shown above, or may have at least 70% identity thereto, e.g. at least 75%, at least 80%, at least 85%, at least 90%, at least 95%, at least 96%, at least 97%, at least 98%, or at least 99% identity thereto.

A rabies L protein may have the sequence shown above, or may have at least 70% identity thereto, e.g. at least 75%, at least 80%, at least 85%, at least 90%, at least 95%, at least 96%, at least 97%, at least 98%, or at least 99% identity thereto.

An exemplary sequence of a rabies G protein (strain B19G) is as follows:

MVPQALLEVPLLVFPLCFGKEPIYTIPDKLGPWSPIDIHHLSCPNNLVV
EDEGCTNLSGFSYMELKVGYILAIKVNGFTCTGVVTEAETYTNFVGYVT
TTFKRKHFRPTPDACRAAYNWKMAGDPRYEESLHNPYPDYRWLRTVKTT
KESLVIISPSVADLDPYDRSLHSRVFPSGKCSGVAVSSTYCSTNHDYTI

-continued

```
WMPENPRLGMSCDIFTNSRGKRASKGSETCGFVDERGLYKSLKGACKLK

LCGVLGLRLMDGTWVSMQTSNETKWCPPDKLVNLHDFRSDEIEHLVVEE

LVRKREECLDALESIMTTKSVSFRRLSHLRKLVPGFGKAYTIFNKTLME

ADAHYKSVRTWNEILPSKGCLRVGGRCHPHVNGVFFNGIILGPDGNVLI

PEMQSSLLQQHMELLESSVIPLVHPLADPSTVFKDGDEAEDFVEVHLPD

VHNQVSGVDLGLPNWGKYVLLSAGALTALMLIIFLMTCCRRVNRSEPTQ

HNERGTGREVSVTPQSGKIISSWESHKSGGETRL
```

where the extracellular domain is shown in regular font, the transmembrane domain underlined, and the intracellular domain in italics.

An alternative so-called "optimised" G protein, having B19 strain intracellular domain but the extracellular domain from a different strain, has the sequence:

```
MVPQALLFVPLLVFPLCFGKFPIYTIPDKLGPWSPIDIHHLSCPNNLVV

EDEGCTNLSGFSYMELKVGYISAIKMNGETCTGVVTEAETYTNEVGYVT

TTFKRKHFRPTPDACRAAYNWKMAGDPRYEESLHNPYPDYHWLRTVKTT

KESLVIISPSVADLDPYDRSLHSPVFPGGNCSGVAVSSTYCSTNHDYTI

WMPENPRLGMSCDIFTNSRGKRASKGSETCGFVDERGLYKSLKGACKLK

LCGVLGLRLMDGTWVAMQTSNETKWCPPGQLVNLHDFRSDEIEHLVVEE

LVKKREECLDALESIMTTKSVSFRRLSHLRKLVPGFGKAYTIFNKTLME

ADAHYKSVRTWNEIIPSKGCLRVGGRCHPHVNGVFFNGIILGPDGNVLI

PEMQSSLLQQHMELLVSSVIPLMHPLADPSTVEKNGDEAEDFVEVHLPD

VHERISGVDLGLPNWGKYVLLSAGALTALMLIIFLMTCWRRVNRSEPTQ

HNLRGTGREVSVTPQSGKIISSWESHKSGGETRL
```

where the extracellular domain is shown in regular font, the transmembrane domain underlined, and the intracellular domain in italics.

A rabies G protein may have either of the sequences shown above, or may have at least 70% identity thereto, e.g. at least 75%, at least 80%, at least 85%, at least 90%, at least 95%, at least 96%, at least 97%, at least 98%, or at least 99% identity thereto.

A pseudotyped envelope protein for use with a vector based on a rabies virus may have the intracellular domain and optionally the transmembrane domain from either of the G protein sequences shown above, or may have at least 70% identity thereto, e.g. at least 75%, at least 80%, at least 85%, at least 90%, at least 95%, at least 96%, at least 97%, at least 98%, or at least 99% identity thereto. The extracellular domain may have at least 70% identity, e.g. at least 75%, at least 80%, at least 85%, at least 90%, at least 95%, at least 96%, at least 97%, at least 98%, or at least 99% identity to one of the extracellular domain sequences shown above or may be selected depending on the cell to which the vector will be targeted.

Each gene (or open reading frame) encoded by the vector is typically associated with appropriate regulatory signals to ensure expression (i.e. transcription and translation). This applies to any heterologous genes carried by the vector as well as to the gene encoding the replication modulator protein and other viral proteins. Thus each gene may comprise a transcriptional start signal and a transcriptional stop signal. Transcriptional start signals are typically C-rich sequences of around 8 bases in length, such as ACATCCCT and ACACCCCT. Stop signals are typically stretches of poly(A), such as AAAAAAA. Each gene may also comprise a Kozak sequence to ensure appropriate transcriptional initiation. Additional regulatory sequences, including non-mononegaviral elements, such as internal ribosomal entry sites (IRES) may also be present to ensure desired levels of gene expression, especially for any heterologous gene or genes.

Percent (%) amino acid sequence identity with respect to a reference sequence is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. % identity values may be determined by WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Monosynaptic Circuit Tracing

Rabies virus vectors lacking a functional glycoprotein G are well known for mapping synaptic connections between neurons. See, for example, U.S. Pat. No. 8,334,095 B2.

Rabies virus spreads selectively between synaptically connected neurons, exclusively in the retrograde direction (except for some sensory neurons). Rabies viruses which lack a G glycoprotein are unable to bud from the surface of an infected cell. Thus, a vector based on a rabies virus in which the G gene has been deleted or inactivated (ΔG-Rabies, or RVdG) can only propagate to adjacent cells if a gene encoding a G glycoprotein (or another pseudotyped envelope protein) is supplied in trans, e.g. via a helper virus, such as an adeno-associated viral (AAV) vector. If the ΔG-Rabies vector and the helper virus are carefully targeted to the same cell, the rabies virus is able to propagate to cells synaptically adjacent, but no further (as the adjacent cells do not express the envelope protein required for further propagation). This therefore enables synaptic connections to be visualised and mapped, e.g. via a fluorescent marker protein carried by the ΔG-Rabies vector.

Many variations of the basic labelling method are known. In some examples of mammalian use, ΔG-Rabies is pseudotyped with the envelope protein from avian sarcoma leukosis virus (ASLV) type A or type B (EnvA, EnvB), which are specific for the receptors TVA and TVB respectively. Since these proteins are not naturally expressed in mammals, transduction by the relevant pseudotyped vector can be limited to cells specifically engineered to express TVA or TVB.

Some approaches to synaptic mapping use animal models which have been engineered to express a viral recombinase which may target recognition sites in the rabies vector or helper virus genomes. Further levels of control can be achieved by placing the recombinase gene in the recipient animal under the transcriptional control of an inducible promoter. Alternatively, the recipient animal may have been engineered to possess genomic recognition sites for such a recombinase, in order that a cellular genomic recombination event takes place after transduction with a vector encoding the recombinase protein.

Commonly, the Cre-Lox pairing of recombinase and recognition sites is used, where the Cre recombinase acts on the Lox recognition sites.

However, deletion or inactivation of the G glycoprotein does not interfere with the usual process of viral transcription, protein synthesis and replication of the core within the recipient cell. The accumulation of viral RNA and protein within the cell has the effect that the labelled cells typically remain viable for only 1-2 weeks, as a result of cell viability being directly compromised by viral proteins, an immune response against the infected cell, or other mechanisms.

Switchable Vectors

The vectors of the present invention exploit the coupled nature of mononegaviral transcription and replication to provide a switch for the viral transcription-replication cycle within infected cells, turning the virus on or off depending on the presence (and activity) of specific activating agents or inhibitory agents.

As already described above, the vector encodes a replication modulator protein switchable between a configuration displaying a degron which targets that protein for degradation (e.g. by the proteasome) and a configuration which does not display that degron and is hence more stable. These configurations of the replication modulator protein are designated "targeted" and "untargeted" to reflect the presence or absence of the degron.

Thus, while the replication modulator protein exists primarily in the targeted configuration, the virus is unable to build up a significant quantity of the relevant protein in a functional form. Although a short period of viral transcription and replication may be possible immediately after primary infection, viral transcription and replication will stall thereafter. If this configuration is maintained for a sufficient period of time, the virus will eventually be cleared from the cell, since the other viral proteins and the RNA genome itself will be broken down by the normal mechanisms of the cell.

The length of time for which the virus will persist in the infected cell in the targeted configuration will vary depending on the particular cell and virus in question. In general, though, a vector of this sort based on the rabies virus is likely to be cleared from a neural cell within a period of approximately two weeks to one month.

In general, the switch between configurations results from interaction between the regulator moiety and the activating agent or inhibitory agent, as appropriate. The interaction may involve covalent or non-covalent modification of the regulator moiety.

Covalent modification may be achieved by enzyme action, i.e. the activating agent or inhibitory agent is an enzyme and the regulator moiety is a substrate for that enzyme. An example of covalent modification is proteolytic cleavage.

Non-covalent modification may be achieved by binding of the activating agent or inhibitory agent to the regulator moiety, i.e. the activating agent or inhibitory agent may be a ligand for the regulator moiety.

Thus an activating agent may stabilise a replication modulator protein by "cleavage-induced stabilisation" or "ligand-induced stabilisation". Conversely, an inhibitory agent may destabilise a replication modulator protein by "cleavage-induced destabilisation" or "ligand-induced destabilisation". (These may also be referred to as "cleavage-induced degradation" or "ligand-induced degradation".) Other mechanisms may be possible.

It will be apparent that the switch between targeted and untargeted configurations may be reversible or irreversible, depending on the nature of the replication modulator protein and the activating or inhibitory agent. For example, where the activating agent or inhibitory agent is a ligand for the modulator protein, the switch between the two configurations may be reversible. Where the switch between the configurations is mediated by covalent modification such as proteolysis, the switch is likely to be irreversible.

In the context of the present invention the degron may be any feature which confers a particularly short half-life to a protein, e.g. by marking it for degradation. Many different types of degron are known. Some act by marking a protein for ubiquitinylation (ubiquitin-dependent degrons), while others are ubiquitin-independent.

The degron may be a PEST sequence. A PEST sequence is a peptide sequence motif typically at least 12 amino acids in length, hydrophilic, and rich in proline, glutamic acid, serine and threonine. Li at al. (Generation of Destabilized Green Fluorescent Protein as a Transcription Reporter, J. Biol. Chem. 1998; 273(52): 34970-5) describe a PEST sequence at residues 423-450 of mouse ornithine decarboxylase, having the sequence HGFPPEVEEQDDGTLPMSCAQESGMDRH (SEQ ID NO: 8) and variants thereof which also have destabilising activity. The region from residues 422 to 461 of this protein ("mODC(422-461)") is employed in the examples below and has the sequence

SHGFPPEVEEQDDGTLPMSCAQESGMDRHPAACASARINV.

The C-terminal region of NPDC-1 (Neural proliferation and differentiation control protein-1) also possesses a PEST motif, having the sequence KELDTASSDEENEDGDFTVYECPGLAPTGEMEVR (SEQ ID NO: 10). See (NPDC-1, a Novel Regulator of Neuronal Proliferation, Is Degraded by the Ubiquitin/Proteasome System through a PEST Degradation Motif, Spencer et al., J. Biol. Chem. 2004; 279, 37069-37078)

Thus the replication modulator protein may comprise a PEST sequence. A replication modulator protein comprising a PEST sequence will typically be an inhibitory modulator protein since it will tend to be degraded until the PEST sequence is removed.

A PEST sequence will often be located C-terminal of the viral protein moiety, e.g. at the C-terminus of the modulator protein.

Thus, the replication modulator protein will typically comprise a viral protein moiety and a regulator moiety located C-terminal of the viral protein moiety, wherein the regulator moiety comprises a protease cleavage site and a PEST sequence.

The following amino acid sequence is an example of a replication modulator protein comprising a rabies virus N protein as viral protein moiety, and a regulator moiety comprising a TEV protease cleavage site and a PEST sequence ("N-TEV-PEST"):

```
MDADKIVFKVNNQVVSLKPEIIVDQYEYKYPAIKDLKKPCITLGKAPD

LNKAYKSVLSGMSAAKLNPDDVCSYLAAAMQFFEGTCPEDWTSYGIVI

ARKGDKITPGSLVEIKRTDVEGNWALTGGMELTRDPTVPEHASLVGLL
```

-continued

```
LSLYRLSKISGQNTGNYKTNIADRIEQIFETAPFVKIVEHHTLMTTHK

MCANWSTIPNFRFLAGTYDMFFSRIEHLYSAIRVGTVVTAYEDCSGLV

SFTGFIKQINLTAREAILYFFHKNFEEEIRRMFEPGQETAVPHSYFIH

FRSLGLSGKSPYSSNAVGHVFNLIHFVGCYMGQVRSLNATVIAACAPH

EMSVLGGYLGEEFFGKGTFERREERDEKELQEYEAAELTKTDVALADD

GTVNSDDEDYFSGETRSPEAVYTRIMMNGGRLKRSHIRRYVSVSSNHQ

ARPNSFASFLNKTYSSDSGSGENLYFQSGSGSHGFPPEVEEQDDGTLP

MSCAQESGMDRHPAACASARINV
```

The N protein viral protein moiety is shown in regular font. the regulator moiety is shown in italics, with single underlining for the TEV sequence and double underlining for the PEST sequence.

The degron may be an N-terminal amino acid or short N-terminal sequence motif. It is well established that proteins having residues other than Met, Gly or Val at their N-terminus tend to be less stable than those having Met, Gly or Val. This is referred to as the N-end rule. See, for example, Varshavsky, A. (2011) "The N-end rule pathway and regulation by proteolysis"; Protein Science 20: 1298-1345.

Various mechanisms are involved in determining the stability of a protein via its N-terminus, including the so-called Arg/N-end rule pathway (which involves N-terminal arginylation of protein substrates) and the Ac/N-end rule pathway (which involves co-translational N-terminal acetylation of some proteins having Met, Ala, Val, Ser, Thr or Cys. In some cases, a protein's original N-terminus will be processed by endogenous cellular enzymes (e.g. Met-aminopeptidases). In such cases, the N-terminal residue present after processing may represent the degron.

As a guideline, the order of stability in mammalian cells (least stable/shortest half life to most stable/longest half life) is roughly Gln (Q), Arg (R), Glu (E), Phe (F), Asp (D), Cys (C), Lys (K), Asn (N), Ser (S), Tyr (Y), Trp (W), His (H), Ala (A), Leu (L), Thr (T), Ile (I), Pro (P), Gly (G), Met (M), Val (V).

Different alternatives may be tested for any given protein to identify a suitable combination of residues to be displayed at the N-terminus before and after cleavage, to achieve the required differential in protein stability.

Thus the modulator protein may comprise an N-terminal regulator moiety and a viral protein moiety downstream of the regulator moiety, wherein the regulator moiety comprises a first residue at its N-terminus and a cleavage site for a cognate protease, and wherein, after cleavage by the cognate protease, the viral protein moiety has at its N-terminus a second residue which confers a different half life than the first residue.

Thus an inhibitory modulator protein may comprise a first N-terminal residue, and be cleavable (e.g. by a protease) to expose a second N-terminal residue which confers greater stability than the first N-terminal residue. For example, the first N-terminal residue may be Arg or Lys (or the sequence Arg-Lys), and the second N-terminal residue may be Val.

Conversely, an inhibitable modulator protein may be expressed with a first N-terminal residue, and be cleavable (e.g. by a protease) to expose a second N-terminal residue which confers lower stability than the first N-terminal residue. For example, the first N-terminal residue may be Met or Val, or the sequence Met-Val, and the second N-terminal residue may be Arg or Lys (or the sequence Arg-Lys.

In both cases, the regulator moiety will be located at the N-terminus of the molecule and may comprise a cleavage site for a cognate protease immediately upstream of the chosen second N-terminal residue.

Typically, the modulator protein will comprise one or more surface-exposed Lys residues to act as sites for ubiquitinylation.

The degron technologies described above provide examples of cleavage-induced stabilisation and cleavage-induced destabilisation.

Other conditional degron technologies are described in Kanemaki et al., Eur. J. Physiol. (2013) 465: 419-425 and references cited therein, and details of some of these technologies are provided below.

An example of ligand-induced destabilisation is the auxin-inducible degron. This utilises an auxin to induce targeting for degradation. Binding of an auxin (such as indole-3-acetic acid (IAA) or 1-naphthaleneacetic acid (NAA)) to the plant protein TIR1 (a component of the ubiquitin ligase designated SCF) allows TIR1 to interact with proteins of the AUX/IAA family, resulting in ubiquitinylation of the AUX/IAA protein and its subsequent degradation by the proteasome. Other components of the SCF ubiquitin ligase are well conserved in most eukaryotes. Thus, an AUX/IAA protein such as IAA17 may be employed as a regulator moiety in cells which express TIR1 (e.g. eukaryotic non-plant cells which have been engineered to express TIR1). Addition of an auxin to the cell will then result in degradation of any protein comprising an AUX/IAA moiety. Thus an inhibitable regulator moiety may comprise an AUX/IAA protein.

The DD-FKBP and LID-FKBP degron systems are based on the FK506 binding protein 12 (FKBP12), and provide examples of ligand-induced stabilisation and ligand-induced destabilistion, respectively.

Destabilisation domains of FKBP12 ("DD-FKBP") are continuously degraded but are stabilised by the presence of a ligand called "Shield-1", which is a cell-permeable analogue of rapamycin. (See Banaszynski et al., Cell. 2006 Sep. 8; 126(5): 995-1004.) Thus DD-FKBP can be used as an inhibitory regulator moiety, which can be stabilised by introduction of Shield-1. The DD-FKBP moiety can be located either N-terminal or C-terminal of the viral protein moiety in the modulator protein.

The LID-FKBP system is a ligand-induced destabilisation (or degradation) system in which a synthetic 19 amino acid degron having the sequence TRGVEEVAEGVVLLRRRGN (SEQ ID NO: 12) is fused to the C-terminus of the FKBP12 protein (or a Phe36Val variant thereof designated $FKBP12^{F36V}$). The peptide binds to the ligand binding pocket of FKBP12 thus sequestering it. Addition of another ligand for the same binding site, such as Shield-1, induces release and exposure of the degron peptide, which consequently marks the entire protein for degradation. Thus, a regulator moiety may comprise a LID-FKBP moiety. A regulator moiety comprising a LID-FKBP moiety would typically be located C-terminal of the viral protein moiety in a replication modulator protein, and ideally at the C-terminus of the modulator protein.

Binding of a hydrophobic ligand to a regulator moiety may also be used to mark a protein for degradation. For example, the so-called "HaloTag" system employs a modified haloalkane dehydrogenase (the HaloTag) and a small molecule hydrophobic ligand (e.g. HyT13) which covalently binds to the active site of the modified haloalkane dehydrogenase. It appears that the binding of the ligand to the protein marks the protein for degradation by the proteasome. Thus an inhibitable regulator moiety may comprise a HaloTag, which and may be located either N-terminal or C-terminal of the viral protein moiety.

It will be clear from the discussion above that the switch between targeted and untargeted configurations of the replication modulator protein (or vice versa) may be implemented by cleavage of the regulator moiety from the viral protein moiety. This is typically accomplished by a protease. In such cases, the regulator moiety typically comprises a degron and a cleavage site for the protease, wherein the protease cleavage site is located between the viral protein moiety and the degron. The replication modulator protein may comprise a linker peptide located between the viral protein moiety and the regulator moiety. Additionally or alternatively, the regulator moiety may comprise a linker peptide between the protease cleavage site and the degron.

Unless one of the components of the protein have any specific functional requirements the moieties of the replication modulator may be in any appropriate orientation. For example, the viral protein may be located N-terminal of the regulator moiety, or the regulator moiety may be located N-terminal of the viral protein, with the linker (where present) between them. However, some degron sequences do have a requirement for being located at the N- or C-terminus of the protein.

A peptide linker is typically between 3 and 30 amino acids in length, with a high proportion of small and hydrophilic amino acid residues (e.g. glycine and serine) to provide the required flexibility without compromising aqueous solubility of the molecule. It may also contain the cleavage site on which the protease acts. The residues other than the cleavage site (and any other sequence required for recognition by the protease) may comprise at least 50% glycine and serine residues, at least 60% glycine and serine residues, at least 70% glycine and serine residues, at least 80% glycine and serine residues, or at least 90% glycine and serine residues.

Proteases

The protease may be orthogonal to the target cell, which is to say that the protease recognises a cleavage site not found in native proteins encoded by and expressed in the target cell (i.e. in the proteome of the target cell).

Thus the particular protease may vary depending on the intended target cell to which the vector is to be delivered. The target cell will typically be a neuron, in which case the protease should not act on any native cellular proteins expressed within that neuron.

It will also be apparent that the selected protease should not act on other proteins encoded by the vector.

Examples of suitable proteases include:

Viral proteases, such as Tobacco Etch Virus protease (TEVp) and human rhinovirus (HRV) 3C protease;

Factor Xa;

Enterokinase;

Granzyme B;

Thrombin.

Consensus cleavage sites for these proteases are as follows, where "\" indicates the position of the cleaved peptide bond: Protease Cognate cleavage site(s)

| Protease | Cognate cleavage site(s) |
|---|---|
| TEVp | ENLYFQ\G |
| | ENLYFQ\S |
| HRV 3C protease | LEVLFQ\GP |
| Factor Xa | IEGR\ |
| Enterokinase | DDDDK\ |
| Thrombin | LVPR\GS |

Pharmaceutical Compositions and Methods of Treatment

The agents described herein can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, which may be by any suitable route, and may be oral or parenteral. Because of the difficulties experienced with oral delivery of peptide agents, parenteral administration may prove the most suitable. Suitable parenteral routes include but are not limited to intravenous, intramuscular, intraperitoneal, cutaneous, subcutaneous, transdermal, and other mucosal routes such as nasal, buccal, rectal and vaginal routes. Examples of suitable compositions and methods of administration are provided in Esseku and Adeyeye (2011) and Van den Mooter G. (2006).

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whatever the nature of the active agent that is to be given to an individual (e.g. a virion, encapsulated nucleic acid molecule, or other pharmaceutically useful agent according to the present invention), administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

EXAMPLES

We fused a proteasome-targeting domain to each protein of the Rabies virus (individually or in combinations) in order to target them to the proteasome (FIG. 1A-B, full list of constructs in Table 1). To implement a level conditional control on viral protein stability, the Tobacco Etch Virus cleavage site (TEVs) was interposed between the viral proteins and the proteasome-targeting domain. The Tobacco Etch Virus protease (TEVp) selectively cleaves the TEVs linker, separating the viral proteins form the proteasome-targeting domain, sparing them from degradation (FIG. 1A). The binary system composed by TEVp and TEVs can be pharmacologically regulated to modulate on the extent and temporal window of viral protein degradation during viral production and in vivo.

Namely, the virus is able to transcribe and replicate only when TEVp is present, giving origin to a system in which viral transcription and replication are constitutively OFF unless TEVp is provided.

We screened the suitability to viral production and TEV dependency for all generated viral constructs (FIG. 1). The result of the screen points to the N protein as the sole viral protein whose conditional destabilization is sufficient to reversibly suppress the viral transcription-replication cycle (FIG. 1F, K) in a TEVp dependent manner. The destabilization of all other viral proteins, alone or in combination, gives origin to viruses that are either unable to amplify in vitro or that amplify both in presence or absence of TEVp (FIG. 1).

Figure 6:
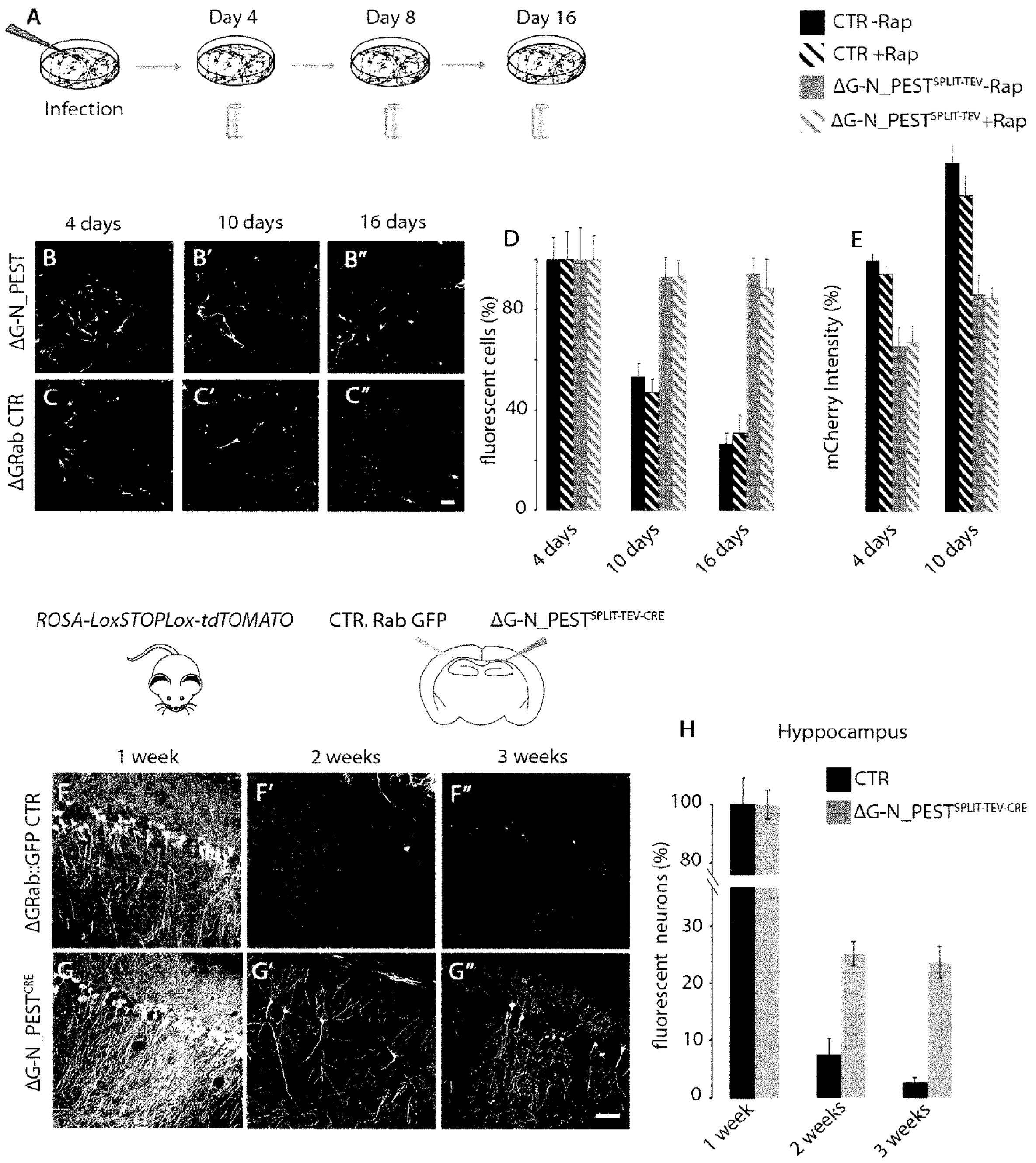

After a further round of improvement on the viral cassette design (Supplementary Text, FIG. 6, 7) we were able to produce a Self-inactivating Rabies (SiR) based on an N-protein destabilised Rabies cassette with the desired TEV-dependent ON-OFF kinetics.

Figure 2:
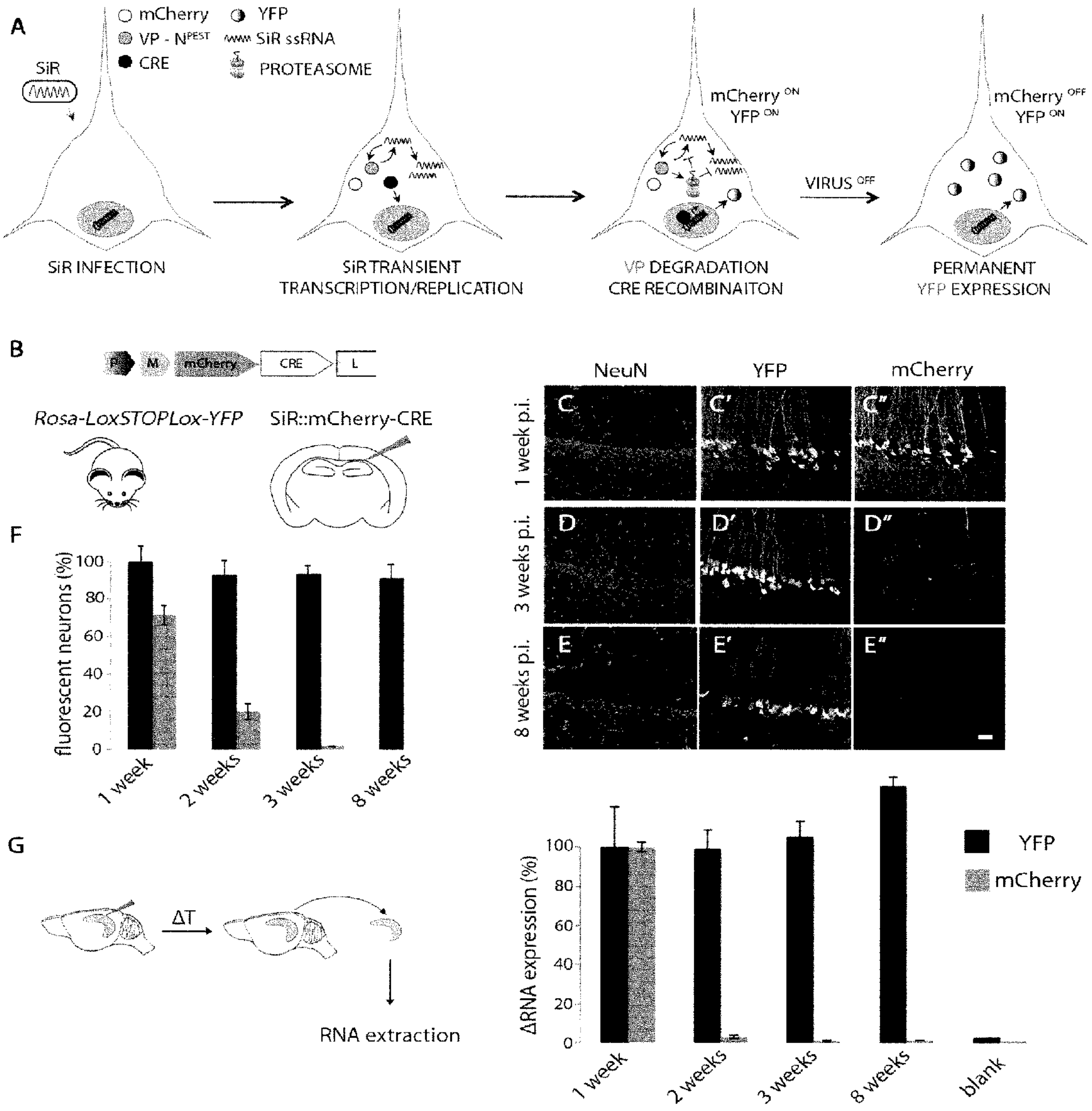
Figure 8:
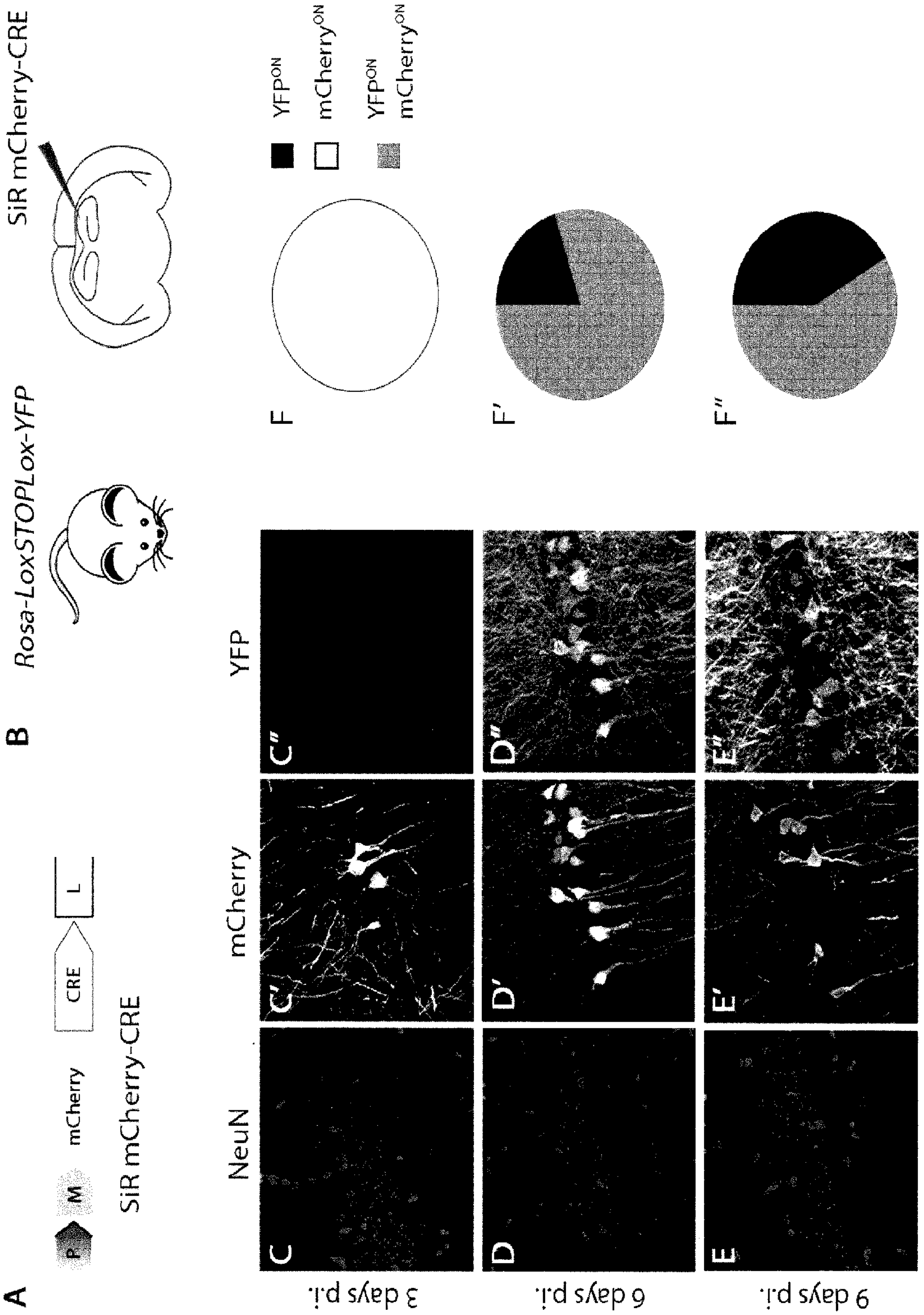

We then generated an SiR encoding for CRE recombinase and mCherry$^{PEST}$ (SiR$^{CRE\text{-}mCherry}$, FIG. 2B). We tested SiR transcription-replication kinetics and cytotoxicity in vivo by injecting SiR$^{CRE\text{-}mCherry}$ in the CA1 pyramidal layer of Rosa-LoxP-STOP-LoxP-YFP mice (FIG. 2B). Transient expression of the CRE recombinase driven by the SiR should ensure a permanent recombination of the Rosa locus and YFP expression even after a complete transcriptional shut down of the virus (FIG. 2A). Indeed, while 3 days post-infection (p.i.) only the virally encoded mCherry can be detected (FIG. 8 C-C"), already by 6 days post-infection, the viral encoded CRE recombinase induces recombination of the conditional mouse reporter cassette and expression of YFP in all infected neurons (FIG. 8 D-D"). The destabilised mCherry$^{PEST}$ marks the presence of active virus with high temporal resolution (half life ~2 hrs) (21).

We then assessed the survival of SiR$^{CRE\text{-}mCherry}$ infected CA1 pyramidal neurons (by following YFP$^{ON}$ neurons over a 8-weeks period) and monitor the switching OFF of mCherry in infected neurons as a proxy of the viral transcription-replication cycle. One week post-infection SiR$^{CRE\text{-}mCherry}$ begins to switch OFF in a fraction of infected neurons (29±3% mCherry$^{OFF}$ YFP$^{ON}$, FIG. 2C-C'", F). By three weeks post-infection the transition is complete as virtually all YFP$^{ON}$ neurons show no expression of the virally encoded mCherry (98±2% YFP$^{ON}$ mCherry$^{OFF}$, FIG. 2E-E'", F, N=3). More importantly, during the 8 weeks observation period we detected no significant neuronal loss following SiR infection (no significant decrease of YFP$^{ON}$ neurons over the 8 weeks period, one-way ANOVA, F=0.19, P=0.90, N=3 per time-point, FIG. 2E-E", F). On the contrary, upon ΔG-Rabies infection, the majority of infected neurons in the hippocampus die within 2 weeks from the primary infection (hippocampus, 92±3% cell death at 2 weeks, n=3 per time-point, one-way ANOVA, F=101, P=$2.4\times10^{-5}$, FIG. 92±3%). In order to gain better temporal resolution of the viral transcription-replication cycle, without the caveat of the mCherry$^{PEST}$ protein half life, we measured viral RNA titers by real time PCR on brain extracts of infected animals at 1, 2, 3 and 8 weeks post-infection. In agreement with the mCherry expression results, viral titer drops to near-background level by two weeks post-infection (FIG. 2G). Overall, these results show that the SiR$^{CRE\text{-}mCherry}$ transcription-replication kinetics provide enough time to generate an early CRE recombination event (FIG. 8D-D'") before the virus disappears (FIG. 2G), which ensures permanent genetic access to the infected neurons without affecting neuronal survival (FIG. 2F).

Experiments in vitro indicate that modulation of viral stability by conditional proteasome degradation is sufficient to modulate the viral transcription-replication cycle. In order to assess whether conditional control over viral protein degradation can be achieved in vivo we designed an AAV virus to express TEVp under a doxycycline inducible promoter (AAV$^{TRE::TEVp}$, FIG. 7A) (22). This provides a means of pharmacological control on TEVp expression in vivo and therefore, on viral transcription-replication cycle.

Figure 9:
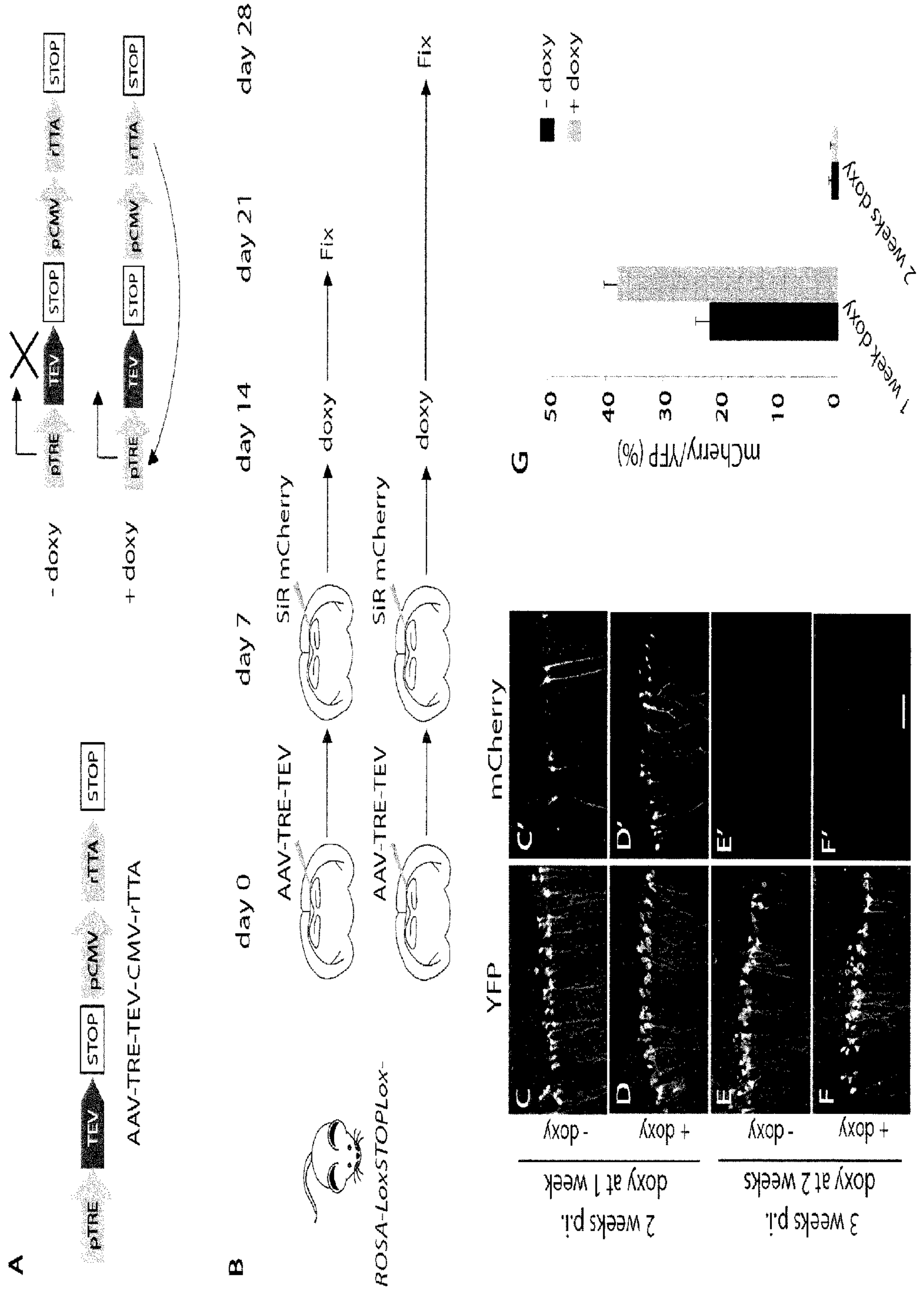
Figure 10:
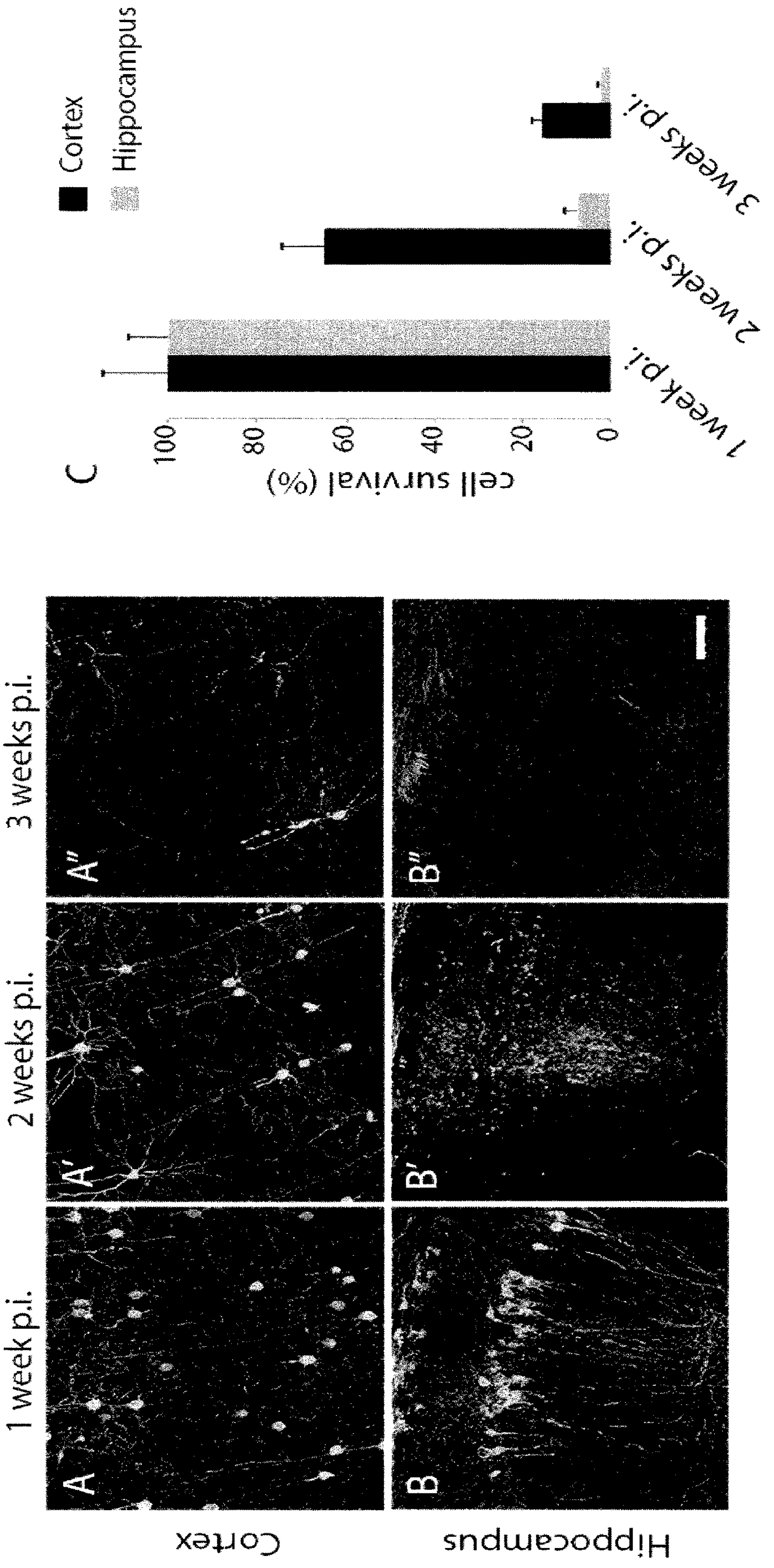
Figure 11A:
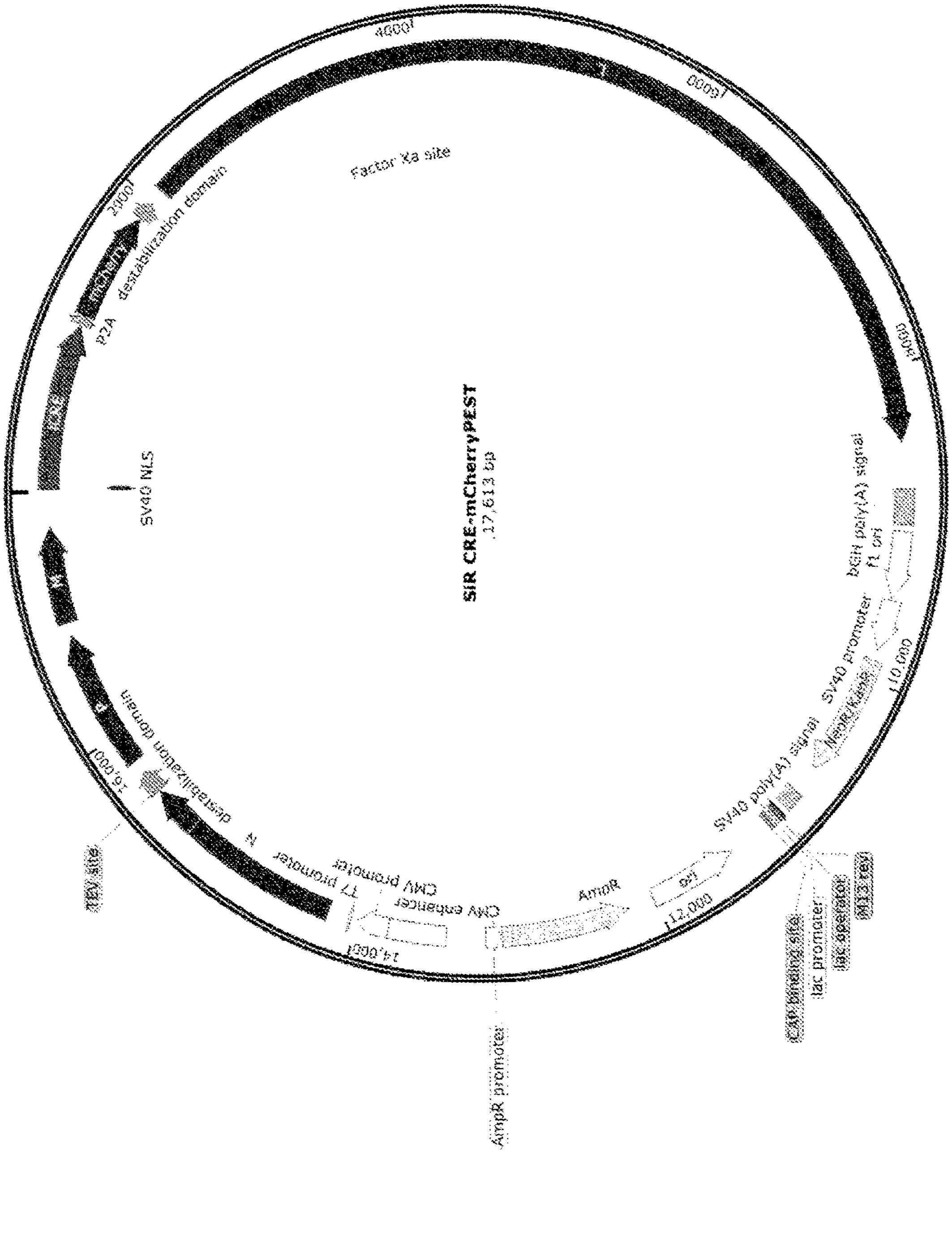

To address if and until what stage after the infection SiR can be reactivated by doxycycline administration, we injected CA1 neurons in the hippocampus with AAV$^{TRE::TEVp}$ followed, 1 week after, by the SiR$^{CRE\text{-}mCherry}$ infection. Doxycycline (100 mg/Kg) was administered by gavage for 2 days at 2 time points, after a week or after 2 weeks (FIG. 9B). In agreement with the RNA analysis, the administration of doxy when the virus is transcriptionally active at 1 week post SiR infection, doubled the percentage of YFP$^{ON}$ mCherry$^{ON}$ neurons (mCherry$^{ON}$YFP$^{ON}$ −doxy 22±3%, +doxy 38±2, P=0.02, FIG. 9G) while no effect was detected by administering doxy 2 weeks post infection (mCherry$^{ON}$YFP$^{ON}$ −doxy 1±1%, +doxy 1±1%, FIG. 9G).

Figure 3:
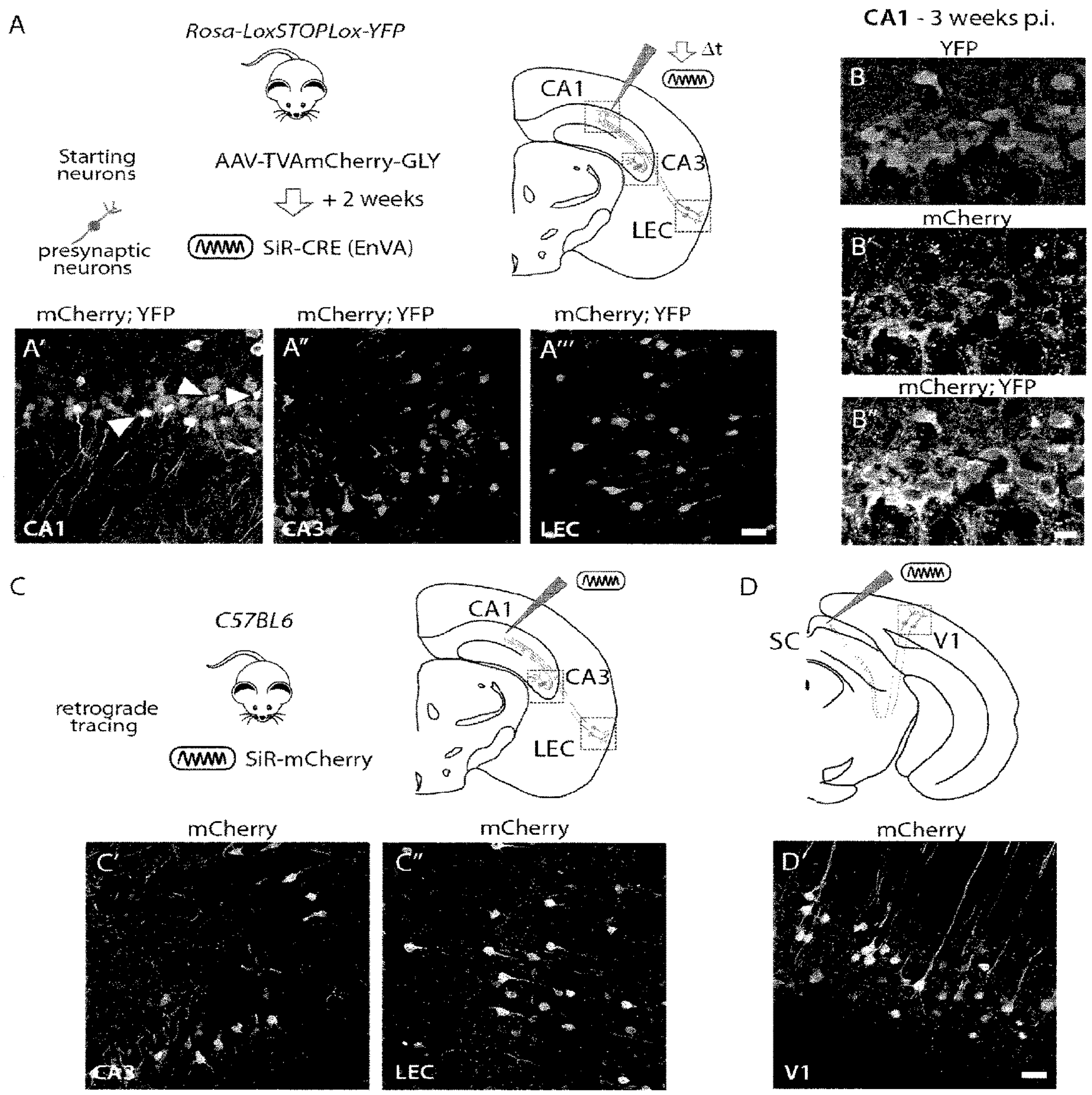

Given the shorter life cycle of the SiR$^{CRE\text{-}mCherry}$ we asked whether it retains the ability to spread transsynaptically from the primary infected neurons before the virus switches off. In order to test this, we first injected an AAV expressing TVA and B19-G in the pyramidal layer of CA1 of Rosa-LoxP-STOP-LoxP-YFP mice followed by infection with an EnvA pseudo-typed SiR virus. As expected from the known anatomical connectivity between CA1 and CA3, we identified neurons labeled by the SiR in the pyramidal layer of CA3 (FIG. 3A-A"), indicating specific transsynaptic spreading. Presynaptic neurons were also identified in the Entorhinal cortex (FIG. 3A'"). More importantly, SiR-infected starting cells expressing TVA and G remained viable throughout the infection period (FIG. 3B-B"). Furthermore, when pseudotyped with the recently developed optimized Rabies Glycoprotein (oG) (17) SiR also functions as a highly effective retrograde (non-transsynaptic) tracer (FIG. 3C,D).

Figure 4:
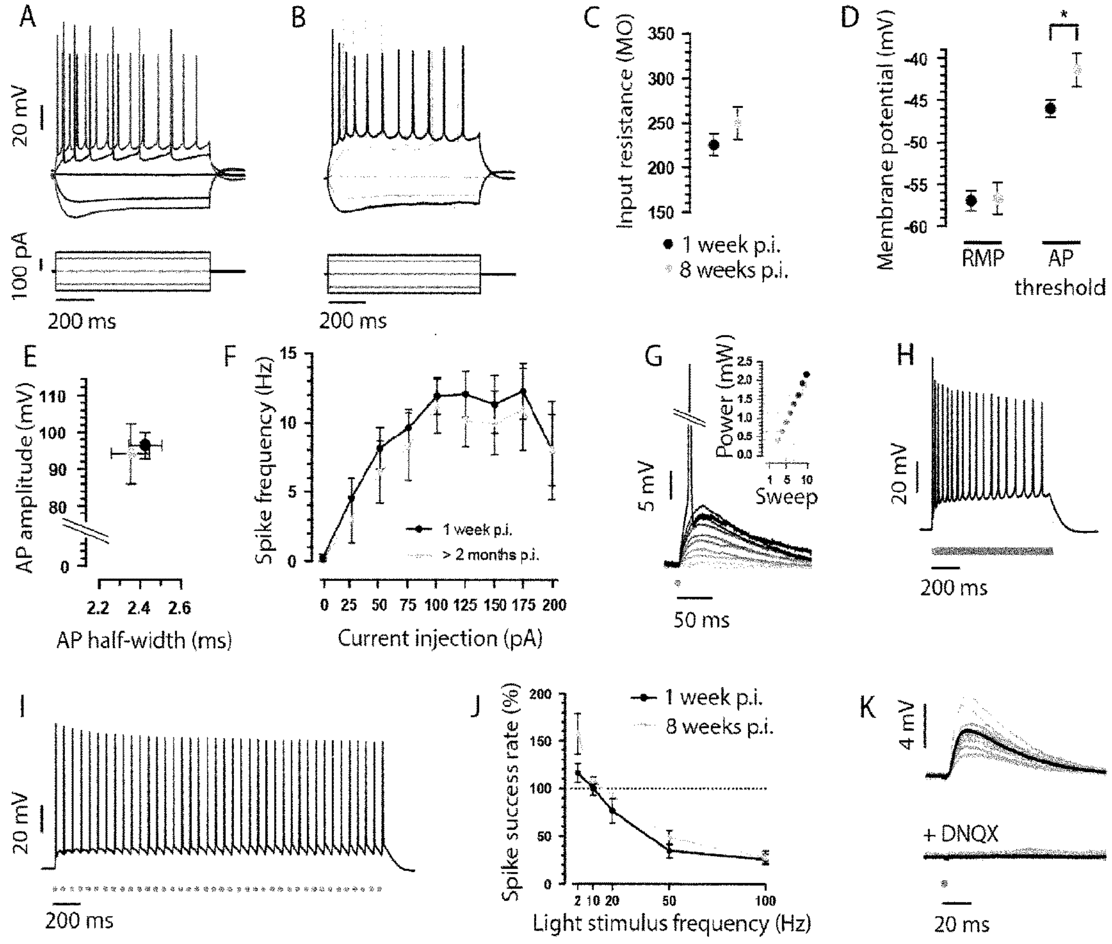

In order to confirm the absence of any long-term effect of the SiR on neuronal physiology, we injected SiR$^{CRE\text{-}mCherry}$ in the pyramidal layer of CA1 in Rosa-LoxP-STOP-LoxP-ChR2YFP. We then compared the electrophysiological properties of the infected neurons one week and two months post-infection. YFP$^{ON}$ neurons in CA1 were recorded in whole-cell patch-clamp mode in acute hippocampal slices. All pyramidal CA1 neurons recorded show regular spiking profiles (FIG. 4 A,B) with no significant difference in the input resistance (226±13 MΩ at one week p.i., n=10, versus 251±18 MΩ after two months, n=8; FIG. 4C), resting membrane potential (−57.0±1.9 mV versus −56.7±1.9 mV; FIG. 4D), action potential amplitude (96.4±3.6 mV versus 94.2±2.9 mV) and action potential half-width (2.4±0.1 ms versus 2.4±0.1 ms; FIG. 4E). Only a minor difference was found in the spike threshold (−46.0±1.0 mV versus −41.3±2.0 mV, P=0.0394; two-tailed two sample Student's t-test FIG. 4D); however, this difference does not affect the instantaneous firing frequency of the neurons (FIG. 4F). ChR2 is successfully expressed in neurons transduced with SiR$^{CRE\text{-}mcherry}$ (FIG. 4G-I). Neurons can be activated at various frequencies with similar reliability both at one week and over two months post-infection (FIG. 4J). A key finding was that light-activation of SiR$^{CRE\text{-}mcherry}$ infected neurons elicits DNQX-sensitive excitatory postsynaptic potentials (EPSPs) in their post-synaptic partners at two months after infection (FIG. 4K), indicating persistence of functional connectivity and no adverse effect on synaptic function.

Figure 5:
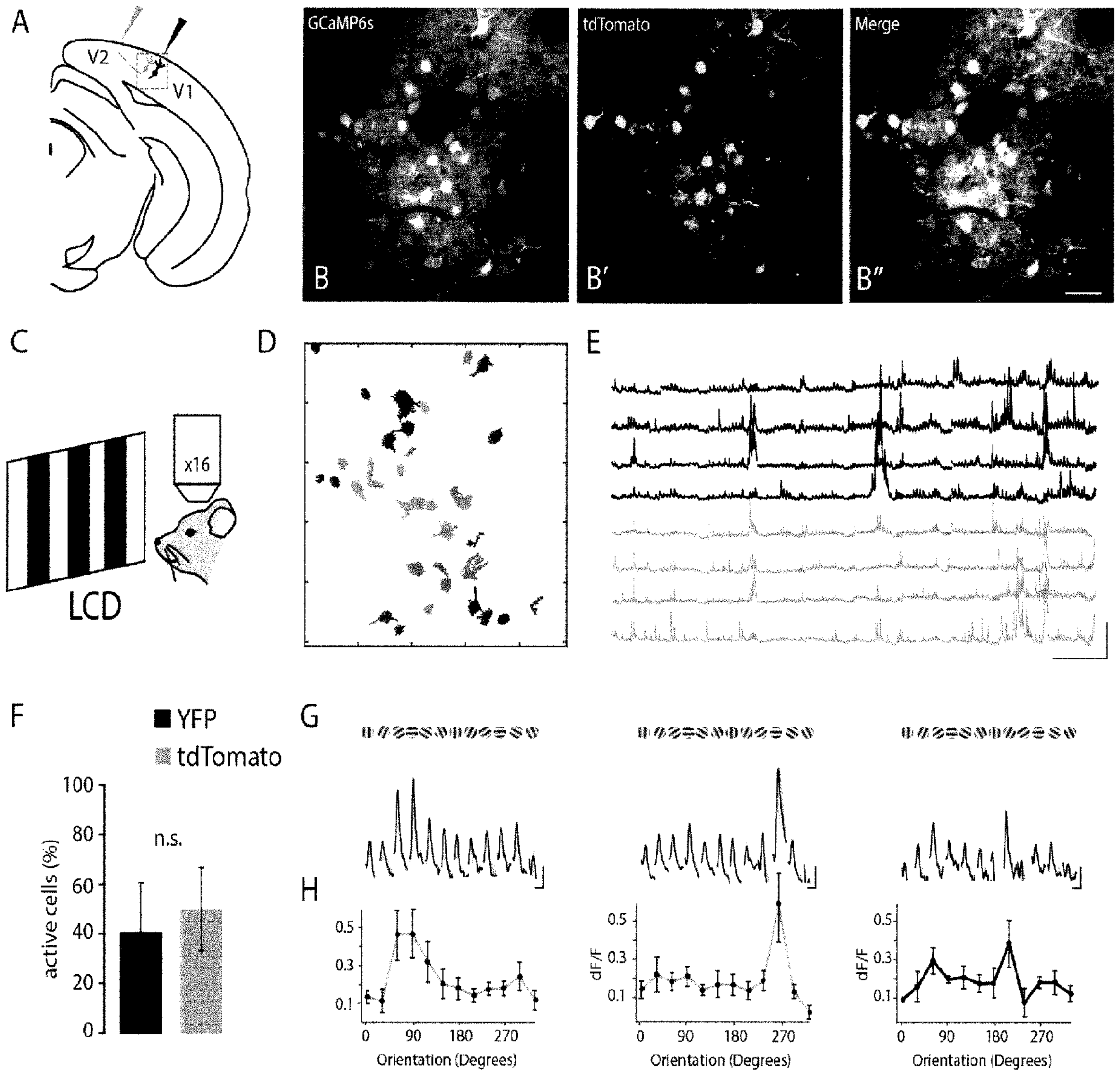

Absence of cytotoxicity and unaltered electrophysiological responses support the use of SiR for long-term circuit manipulations. Presence of functional connectivity between SiR infected neurons and no adverse effect on synaptic function also indicate that network function is likely to be preserved upon SiR infection. In order to directly test whether network-dependent computations are indeed unaffected in SiR mapped circuits, we traced V1 neurons projecting to V2 with SiR and characterized their orientation tuning preferences, as a prototypical example of a network-dependent computation (18). We first targeted V2 projecting neurons by the injection of an oG pseudo-typed SiR$^{CRE}$ in Rosa-LoxP-STOP-LoxP-tdTomato mice. At the same time, we injected an AAV::GcAMP6s in the ipsilateral V1. Retrograde spreading of SiR$^{CRE}$ induces recombination of the Rosa locus permanently labeling V1 neurons projecting to V2 (V1$^{>V2}$) (FIG. 5B-B"). We then monitored the Caz'$^{0}$ dynamics of SiR infected V1$^{>V2}$ neurons in vivo 4 weeks p.i., under a two-photon microscope, while anesthetized animals were exposed to moving gratings of different orientations across the visual field (FIG. 5C) (19). Infected V1 neurons showed significant increase in fluorescence at particular grating orientation resulting in a tuning curve showing direction or orientation selectivity (FIG. 5G, H). Notably, recorded Caz'$^{0}$ responses as well as the percentage of active neurons, were similar between SiR-traced neuron (GCaMP6s$^{ON}$-tdTomato$^{ON}$) and neighboring non-SiR V1 neurons (GCaMP6s$^{ON}$-tdTomato$^{OFF}$) (FIG. 5E, F). These data indicate that SiR traced networks preserve unaltered computational properties and that SiR can be used in combination with GCaMP6s to monitor the $Ca^{2+}$ dynamic with no upper bounds to the temporal window for the optical investigation.

The development of monosynaptically restricted Rabies viruses has had a transformative role in the study of neural circuits. However, until now, the cellular cytotoxicity that accompanies Rabies virus infection effectively limited its use, by and large, to the anatomical mapping of neural circuits. The induced cytotoxicity is linked to the transcriptional activity of the virus, which hijacks of the cellular transcriptional machinery to sustain viral replication (24). Therefore, any replicative competent Rabies virus will eventually compromise cellular physiology. To overcome this limitation and gain life-long genetic and functional access to topologically defined network elements we developed a Self-inactivating Rabies virus, which transcriptionally switches off following the primary infection in a TEVp-dependent manner, both in human Embryonic Stem cells (hESCs) derived neurons (Supplementary results, FIG. 6) and in vivo in mice. In line with the complete transcriptional silencing of the virus we observe no changes in the electrophysiological signature of the infected neurons months after infection and maintenance of synaptic function and circuit integrity, which is key for physiological and behavioral studies. More importantly, we also show that higher level circuit-dependent computations of infected neurons, such as their orientation tuning to moving stimuli, remain unaffected in vivo for months after viral infection.

This, in turn, also shows that SiR can be used to monitor network activity in vivo using calcium imaging. With the canonical B19 ΔG-Rabies the optimal temporal window for optical imaging of neurons is, typically, 5-7 days from the Rabies infection (17). The use of the recently introduced ΔG-Rabies strain variant CVS-N2c$^{\Delta G}$ can push the useful temporal window for imaging further up to 17 days post-infection (25). With SiR there are no upper bounds to the temporal window for the optical investigation of network elements. These attributes make SiR the most valuable solution for the long-term monitoring of neural network activity as well as for the functional and genetic manipulation of neural circuits (26-29). In addition, the unique transient replicative nature of SiR, offers the possibility to follow circuit remodelling after physiological or pathological structural plasticity such as, upon learning, during neurodegenerative conditions or following traumatic brain injuries and it may pave the way to functional interventions at the network level in such cases.

Overall, the development of Self Inactivating ΔG-Rabies provides, for the first time, permanent genetic access to topologically defined network elements without adverse effects to neuronal physiology and circuit function.

Supplementary Text

First Generation ΔG-N$^{PEST}$Rabies. In Vitro and In Vivo Test of Cytotoxicity

In order to obtain conditional regulation of viral protein stability a SPLIT-TEV cassette (30) was added at the C-terminal of each viral protein (ΔG-VP$^{PEST}$ Rabies$^{SPLIT\text{-}TEV\text{-}mCherry}$). In addition a tag (myc, FLAG or V5) was fused to the N-terminal of each viral protein to monitor levels of protein expression. The SPLIT-TEV dimeric protease is only active in presence of rapamycin, and could potentially provide a tool for the exogenous regulation of viral protein stability during production and in vivo. We first tested the capability of the SPLIT-TEV expressed by plasmid to cleave a TEV activity reporter in HEK cells (FIG. 6B) then we tested the ability of the virally expressed cassette to cleave the TEV activity reporter (FIG. 6C).

Figure 7:
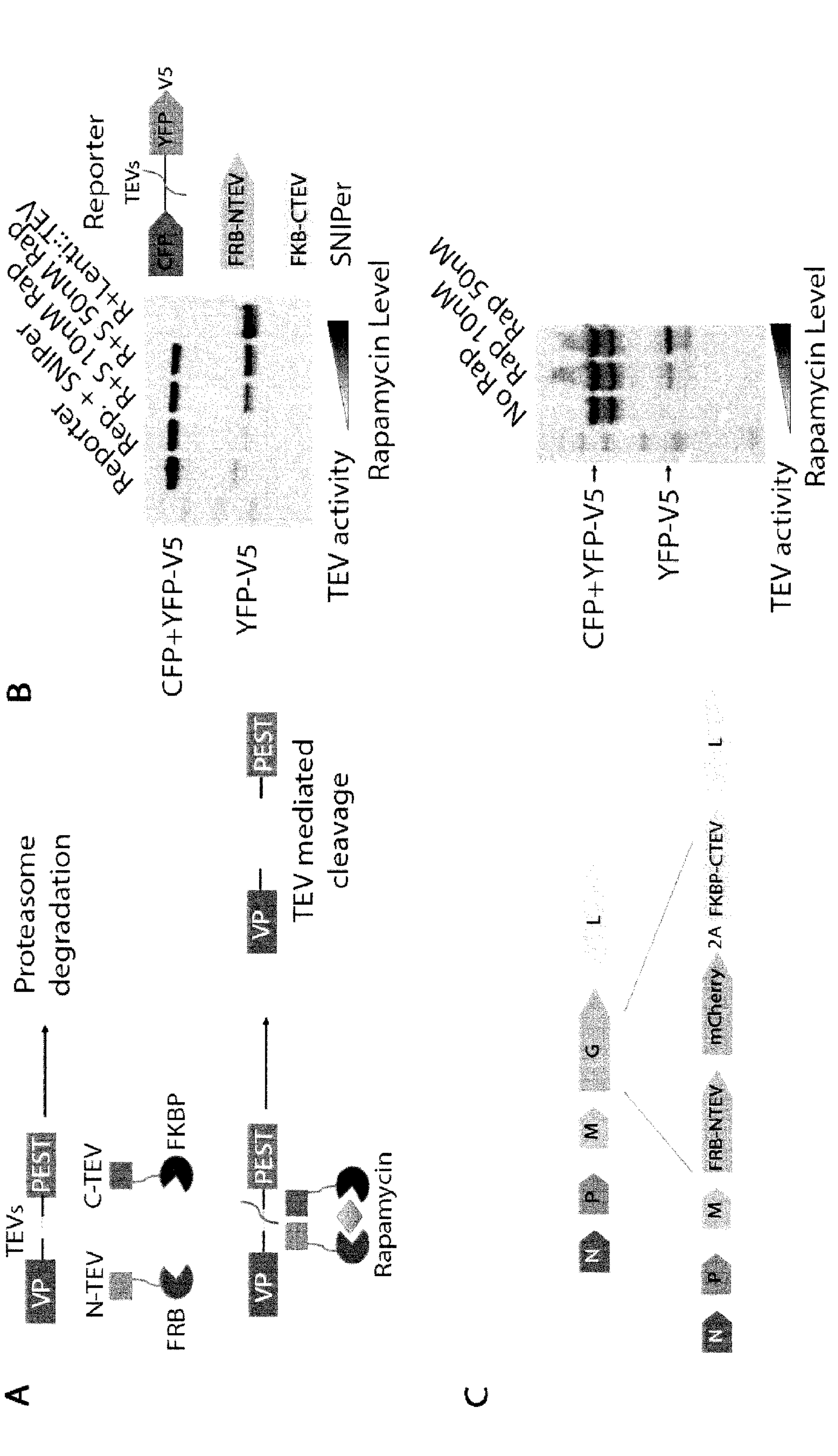

In order to probe the effect of protein destabilization on neuronal survival, we infected human Embryonic Stem cells (hESCs) derived neurons with ΔG-N$^{PEST}$ Rabies$^{SPLIT\text{-}TEV\text{-}mCherry}$. We performed a longitudinal study of the survival of infected neurons and compared survival rate to a control ΔG Rabies. Neurons were infected and imaged longitudinally at 4-10-16 days to evaluate the cell death (FIG. 7A, B-C"). Lentivirus expressing GFP was used to normalize infection rates in order to account for cell death due to the prolonged manipulation and repeated over-night imaging sessions. Only 26±4% of control ΔG-Rabies infected neurons were still detectable at 16 days post-infection (N=3, n=781 for each condition; FIG. 7C-C", D). On the contrary, the ΔG-N$^{PEST}$Rabies$^{SPLIT\text{-}TEV\text{-}mCherry}$ virus showed no significant cell loss after 16 days 94±6% (N=3, n=917 for each condition, FIG. 4B-B", C) and a significant increase in cell survival compared to ΔG-Rabies controls ($P=3.2\times10^{-5}$; paired two-tailed Student's t-test).

To understand if the reduced cytotoxicity of ΔG-N$^{PEST}$ Rabies$^{SPLIT\text{-}TEV\text{-}mCherry}$ is associated with a reduction of the viral transcription, we monitored the intensity of the reporter expressed in neurons infected with the control ΔG-Rabies and the ΔG-N$^{PEST}$Rabies$^{SPLIT\text{-}TEV\text{-}mCherry}$ viruses, which share the same expression cassette (FIG. 7E). Over time the mean mCherry signal of ΔG-N$^{PEST}$Rabies$^{SPLIT-TEV-mCherry}$ infected cells resulted to be significantly lower than controls (mCherry intensity at 10 days, ΔG-Rabies 138±3%, ΔG-N$^{PEST}$Rabies$^{SPLIT-TEV-mCherry}$ 87±7%, P=0.01; N=3, n=584 for each condition; paired two-tailed Student's t-test).

We then tested the performance of the ΔG-N$^{PEST}$ Rabies$^{SPLIT-TEV-mCherry}$ virus in vivo.

We replaced the mCherry gene in the ΔG-N$^{PEST}$ Rabies$^{SPLIT-TEV-mCherry}$ virus with the CRE recombinase (ΔG-N$^{PEST}$Rabies$^{SPLIT-TEV-CRE}$). This ensures that infected neurons can be permanently labeled after a complete transcriptional shut down of the virus, allowing to discriminate between viral silencing and cell death. We injected ΔG-N$^{PEST}$Rabies$^{SPLIT-TEV-CRE}$ in CA1 of Rosa-LoxP-STOP-LoxP-tdtomato reporter mouse line in CA1 in the hippocampus. We observed a significant increase in neuronal survival upon ΔG-N$^{PEST}$Rabies$^{SPLIT-TEV-CRE}$ infection compared to that observed upon infection with control ΔG Rabies (25±2%, at 2 weeks for ΔG-N$^{PEST}$ Rabies$^{SPLIT-TEV-CRE}$ and 8±3%, at 2 weeks for ΔG Rabies $P=7\times10^{-3}$, FIG. 7H). However prominent neuronal loss was still present upon ΔG-N$^{PEST}$Rabies$^{SPLIT-TEV-CRE}$ infection (76±3%, at 3 weeks, $P=9\times10^{-4}$)

The residual cytotoxicity of ΔG-N$^{PEST}$ Rabies$^{SPLIT-TEV-CRE}$ might be linked to a constitutive low basal dimerization and activity of the SPLIT-TEV cassette and can give origin to transcriptionally active viral particles. Consistently with this hypothesis, we observed no significant effect on neuronal survival and mCherry expression levels in presence or absence of rapamycin (mCherry expression 10 days p.i. ΔG-N$^{PEST}$Rabies$^{SPLIT-TEV\ -RAP}$ 87±7%, ΔG-N$^{PEST}$Rabies$^{SPLIT-TEV\ +RAP}$ 85±6%, P=0.21; N=3, n=793 for each condition; paired two-tailed Student's t-test; FIG. 7E) and no significant effects on cells survival were associated with the rapamycin administration in hESCs derived neurons (at 16 days; ΔG-Rabies*P 26±4%, ΔG-Rabies$^{-RAP}$ 30±7%, P=0.69; ΔG-N$^{PEST}$Rabies$^{SPLIT-TEV\ +RAP}$ 88%±11%, ΔG-N$^{PEST}$Rabies$^{SPLIT-TEV\ -RAP}$ 94%±6%, P=0.79; N=3, n=833 for each condition; paired two-tailed Student's t-test, FIG. 7D). Furthermore, we observe a constitutive low level of TEV activity in HEK cells in absence of Rapamycin (FIG. 6B, line2) indicating a basal level of Rapamycin-independent SPLIT-TEV dimerization. Overall these results indicate that ΔG-N$^{PEST}$Rabies$^{SPLIT-TEV}$ has reduced cytotoxicity in hESCs derived neurons and in vivo when compared to ΔG-Rabies. However, it fails to completely switch off following the infection, which leads to significantly delayed, yet still present, neuronal cytotoxicity and neuronal loss. For these reasons we generated a second generation of ΔG-N$^{PEST}$Rabies by removing the leaking SPLIT-TEV and replacing it with an mCherry-CRE cassette giving origin to a Self inactivating Rabies virus (SiR) with the desired ON-OFF and TEV dependent kinetics (main text).

Materials & Methods

TABLE 1

Full list of constructs.

| Rabies | $_{N\text{-}ter}$TAGs | $_{C\text{-}ter}$PEST |
|---|---|---|
| pSAD-F3-mCherry | — | — |
| pSAD-F3-$_{N\text{-}ter}$TAGs-mCherry | N$^{Myc}$-P$^{FLAG}$-M$^{V5}$ | — |
| pSAD-F3-$_{N\text{-}ter}$TAGs-N$^{PEST}$-mCherry | N$^{Myc}$-P$^{FLAG}$-M$^{V5}$ | N$^{PEST}$ |
| pSAD-F3-$_{N\text{-}ter}$TAGs-M$^{PEST}$-mCherry | M$^{Myc}$-P$^{FLAG}$-M$^{V5}$ | M$^{PEST}$ |
| pSAD-F3-$_{N\text{-}ter}$TAGs-P$^{PEST}$- mCherry | N$^{Myc}$-P$^{FLAG}$-M$^{V5}$ | P$^{PEST}$ |
| pSAD-F3-$_{N\text{-}ter}$TAGs-L$^{PEST}$- mCherry | N$^{Myc}$-P$^{FLAG}$-M$^{V5}$ | L$^{PEST}$ |
| pSAD-F3-N$^{PEST}$- mCherry | — | N$^{PEST}$ |
| pSAD-F3-$_{N\text{-}ter}$TAGs-(P + L)$^{PEST}$- mCherry | N$^{Myc}$-P$^{FLAG}$-M$^{V5}$ | P$^{PEST}$ L$^{PEST}$ |
| pSAD-F3-(P + L + N)$^{PEST}$- mCherry | — | P$^{PEST}$<br>L$^{PEST}$<br>N$^{PEST}$ |
| pSAD-F3-N$^{PEST}$ -iCRE-2A-mCherryPEST | — | N$^{PEST}$ |
| pSAD-F3-N$^{PEST}$-$_{C}$TEV-FKBP-2A-FRB-$_{N}$TEV- iCRE | — | N$^{PEST}$ |
| Lentiviruses | Gene A | Gene B |
| pLenti-$_{H2B}$GFP-2A-GlySAD | $_{H2B}$GFP | GlySAD |
| pLenti-puro-2A-TEV | puromycin | TEV |
| pLenti-GFP | GFP | — |
| pLenti-$_{H2B}$GFP-2A-oG | $_{H2B}$GFP | oG |
| AAVs | Gene A | Gene B |
| AAV-CMV-TVAmCherry-2A-Gly | TVAmCherry | Gly |
| AAV-TRE$_{tight}$-TEV-CMV-rTTA | TEV (doxy dependent) | rTTA |
| AAV-CAG-GCaMP6s | GCaMP6s | — |

Animal Strains

C57BL/6 wild type (WT) mice and the following transgenic lines were used: Rosa-LoxP-STOP-LoxP-tdtomato (Jackson: Gt(ROSA)26Sortm14(CAG tdTomato, Rosa-LoxP-STOP-LoxP-YFP(Jackson:Gt(ROSA)26Sor<tm1 (EYFP)Cos>). All procedures were conducted in accordance with the UK Animals (Scientific procedures) Act 1986 and European Community Council Directive on Animal Care. Animals were housed in a 12 hours light/dark cycle with food and water ad libitum.

Design and Generation of ΔG Rabies and Lentivirus Plasmids

All the attenuated Rabies plasmids, listed in Table 1, were generated by Gibson cloning using the pSAD-ΔG-F3 plasmid (21) as starting material. Briefly, the Rabies genome was PCR amplified in 2 fragments starting from the protein to be tagged. These fragments were then mixed with the tag and/or PEST domain obtained by oligonucleotides annealing and assembled using Gibson master mix (NEB).

The lentiviral vectors used to generate the packaging cells were derived from a 3$^{rd}$ generation lentivirus transfer vector (gift from Michael Hastings "361 polilinker", originally pCCL-SIN-18PPT.Pgk.EGFP-WPRE). All the lentiviral vectors were generated by Gibson assembly, opening the backbone by digestion with XbaI and KpnI and PCR amplifying the CMV promoter and the different inserts.

Cell Lines

HEK293T cells and BHK were purchased from ATTC. HEK293T packaging cells expressing Rabies glycoprotein (HEK-GG) were generated by lentivirus infection with Lenti-$_{H2B}$GFP-2A-GlySAD (Table 1) and after 3 passages by fluorescent activated cell sorting (FACS) of GFP expressing cells. HEK293T packaging cells expressing Rabies glycoprotein and TEV protease (HEK-TGG) were generated from HEK-GG by lentivirus infection with Lenti-puro-2A-TEV and selected, after 3 passages, with 1 μg/mL of puromycin added to the media for 1 week.

BHK packaging cells for pseudotyping Rabies virus with optimized G (BHK-TGoG) were generated with the same procedure as the HEK-TGG infecting first with pLenti-$_{H2B}$GFP-2A-oG and subsequently with pLenti-puro-2A-TEV. BHK packaging cells for pseudotyping Rabies virus with EnVA receptor (BHK-T-EnVA) were obtained infecting BHK-EnVA with Lenti-puro-2A-TEV and selecting with puromycin.

Viral Screening

For screening of attenuated ΔG-Rabies viruses, HEK-GG or HEK-TGG cells were co-transfected with rabies genome vector, pcDNA-T7, pcDNA-SADB19N, pcDNA-SADB19P, pcDNA-SADB19L, and pcDNA-SADB19G (21) and maintained at 37° C. with 5% $CO_2$ humidified atmosphere in DMEM supplemented with 10% FBS (Gibco) and 100 u/ml Penicillin-Streptomycin. The day after transfection and subsequently every 3 days, cells were washed with PBS, treated with 0.05% trypsin and replated in a new dish in a ratio 1:3. After splitting, cells were maintained for one day at 37° C. and 5% $CO_2$ and then 2 days at 35° C. and 3% $CO_2$. Every 3 days cells were fixed and viral spreading was assessed by FACS sorting the cells for mCherry expression.

Viral Productions

For the recovery of high titer ΔG-Rabies HEK-GG or HEK-TGG, for control or attenuated Rabies respectively, were infected in 10 cm dishes at 70-80% confluence with 1 ml of viral supernatant obtained as described in the viral screening section. Cells were split the day after infection and maintained for 1 or 2 days at 37° C. and 5% $CO_2$ checking daily the viral spreading. When 70-80% of cells expressed the viral marker, the media was replaced with 2% FBS DMEM and maintained for 2 days at 35° C. and 3% $CO_2$. Then, the viral supernatant was collected, cell debris removed by centrifugation at 2500 rpm for 10 minutes followed by filtration with 0.45 μm filter and then the virus concentrated by ultracentrifugation with sucrose cushion as described before (22).

Rabies viruses pseudotyped with oG were produced infecting BHK-T-oG cells in 10 cm dishes with 1 mL of viral supernatant. Cells were split the day after infection and maintained for one or two days at 37° C. and 5% checking daily the viral spreading. When 70-80% of cells expressed the viral marker, the media was replaced with 2% FBS DMEM and maintained for 2-3 days at 35° C. and 3% $CO_2$. Then, the supernatant was collected and processed as previously described (20).

Rabies viruses pseudotyped with EnVA were produced as previously described (22) using BHK-T-EnVA cells instead of BHK-EnVA cells.

In Vitro Cytotoxicity Analysis

Human Embryonic Stem cells (hESCs) derived neurons were kindly provided by Dr. Rick Livesey. Cells were plated in 24-wells glass bottom plates and infected over night with attenuated or control ΔG-Rabies viruses supernatants at comparable MOI to obtain ~5% of infected cells. Cells were imaged every 4 days post infection overnight in a 37° C. heated Leica SP8 confocal microscope in Hibernate®-A Medium (Invitrogen) with 5 random fields imaged for each well. Cell survival was calculated normalizing each condition to the mortality of control Lentivirus-GFP infected hESCs derived neurons imaged and processed in the same conditions.

Viral Injections

All procedures using live animals were approved by the Home Office and the LMB Biosafety committee. For all experiments mice aged between 6-12 weeks were used. Mice were anesthetized with isofluorane delivered at a flow of 3% in 2 L/min of oxygen for the initial induction and then maintained at 1-2% in 2 L/min of oxygen. The anesthetized animal was placed into a stereotaxic apparatus (David Kopf Instruments) and Rimadyl (2 mg/kg body weight) was administered subcutaneously (s.c.) as anti-inflamatory. A small hole (500 μm diameter) was drilled and viruses were injected using a Hamilton neurosyringe. The syringe was left in the brain for 5 min before being retracted. Viruses were injected at the following titers: $3\times10^8$ infectious units/ml for Rabies viruses, $2\times10^{12}$ genomic copies/ml for AAVs, $3\times10^8$ infectious units/ml for Lentiviruses. Up to a max of 400 nl in volume of virus were injected in the following brain areas: CA1 (AP: 2.3 mm, ML: 1.65 mm and DV: 1.45 mm from bregma), V1 (AP: 2.3 mm, ML: 1.65 mm and DV: 1.45 mm from bregma), V2 (AP: 3.6 mm, ML: 1.2 mm, DV:0.6 mm from bregma).

In Vivo Cytotoxicity Analysis

To test in vivo viral cytotoxicity 400 nl of same titer ($3\times10^8$ infectious units/ml) attenuated and control ΔG-Rabies were injected in CA1 of hippocampus contralateral in the 2 hemispheres. At 1-2-3 or 8 weeks p.i. brains were sectioned at the cryostat (35 μm). Infected neurons were imaged sampling the entire hippocampus (acquiring one every 4 sections) using a robot assisted Nikon HCA microscope mounting a 10× (0.45 NA) air objective and fluorescent hippocampal neurons counted using Nikon HCA analysis software. Cell survival for attenuated and control ΔG-Rabies was calculated normalizing each time point to the mortality of control Lentivirus-GFP infected hippocampi using the same injection protocol.

Drug Induced Reactivation of SiR Virus In Vivo

Rosa-LoxP-STOP-LoxP-YFP animals were injected in CA1 of hippocampus with an AAV constitutively expressing rTTA and TEV protease under the control of a doxycycline inducible promoter (Table 1). 1-week p.i. the same area was re-injected with SiR$^{mCherry\text{-}CRE}$ and doxycycline (Santa Cruz Biotechnology, 100 mg/Kg) administered at 1 or 2 weeks post SiR injection. 1 week after drug administration brains were collected and sectioned at the cryostat (35 μm). Infected neurons were imaged and counted sampling the entire hippocampus (acquiring one every 4 sections) using a robot assisted Nikon HCA microscope.

Analysis of SiR Genomic Copies In Vivo

To evaluate the genomic copies of SiR virus in the infected animals over time SiR$^{mcherry\text{-}CRE}$ was injected in CA1 region of hippocampus of Rosa-LoxP-STOP-LoxP-YFP animals. After 1, 2, 3 or 8 weeks, mice were culled and the injected hippocampi manually dissected immediately after. The hippocampi were homogenised using a Tissuelyser II (Qiagen) and processed accordingly to manufactory instruction with RNeasy kit (Qiagen) to extract total RNA. 500 ng of RNA per hippocampus were retrotrascribed using superscript IV kit (Invitrogen) and analysed for GADPH, YFP and mCherry expression by quantitative PCR (rotorgene sybr-green). The Livak method was applied for quantification. The expression of YFP and mCherry was normalized to the expression of the GADPH housekeeping gene ($DCT=CT_{gene}-CT_{GADPH}$) and the variation over time as fold change ($2^{-DDCT}$) to the 1 week time point ($DDCT=DCT_{Time\ point}-DCT_{1\ week}$).

Electrophysiology

For electrophysiological recordings, $SiR^{mCherry-CRE}$ was injected bilaterally in the CA1 of one month-old Rosa-LoxP-STOP-LoxP-ChR2YFP mice. Recordings were made either one week or between two and 3 months p.i.

Coronal hippocampal slices (350 μm) were prepared using a vibrating microtome (7000smz-2, Campden Instruments LTD, Loughborough, UK) in ice-cold sucrose-based cutting solution oxygenated with carbogen gas (95% $O_2$, 5% $CO_2$) and with the following composition (in mM): KCl 3, $NaH_2PO_4$ 1.25, $MgSO_4$ 2, $MgCl_2$ 1, $CaCl_2$ 1, $NaHCO_3$ 26.4, glucose 10, sucrose 206, ascorbic acid 0.40, kynurenic acid 1. Slices were incubated at 37° C. for 30 minutes in a submerged-style holding chamber with oxygenated artificial cerebrospinal fluid (aCSF; in mM: NaCl 126, KCl 3, $NaH_2PO_4$ 1.25, $MgSO_4$ 2, $CaCl_2$ 2, $NaHCO_3$ 26.4, glucose 10) with an osmolarity adjusted to 280-300 mOsm/L and stored thereafter in the same holding chamber at room temperature for at least 1 h. Slices were then individually transferred to the recording chamber and were superfused with oxygenated aCSF at room temperature at a flow-rate of approximately 2 mL/min.

Whole-cell current-clamp recordings were obtained from CA1 neurons using 6-9 MΩ pipettes pulled from borosilicate glass capillaries (1.5 mm OD×0.86 mm ID). Pipettes were filled with artificial intracellular solution containing (in mM): K-gluconate 150, HEPES 10, NaCl 4, ATP-Mg 4, GTP-Na 0.3 and EGTA 0.2; adjusted to pH 7.2 and osmolarity 270-290 mOsm/L. Data were recorded using an Axon Multiclamp 700B amplifier (Molecular Devices, Union City, CA, USA) and signals were low-pass filtered at 2 kH and acquired at 5 kHz using a digitizer (Axon Digidata 1550A, Molecular Devices, Union City, CA, USA) on a PC running pClamp. Light-evoked responses from neurons infected with SiR virus were elicited using a 450-490 nm LED light (pE-300 coolLED system, Scientifica Ltd, Uckfield, UK) through a 40× water immersion objective (0.8 NA).

Pharmacology

The AMPA receptor antagonist DNQX (20 μM; Sigma-Aldrich, Dorset, UK) was used in a subset of electrophysiological recordings in order to probe synaptic connectivity between neurons infected with SiR virus and neighbouring neurons.

In Vivo 2-Photon Imaging

Injected Rosa-LoxP-STOP-LoxP-tdTomato mice (see Viral injections section) were anaesthetized with isofluorane 2%. Animal pinch withdrawal and eyelid reflex were tested to assay the depth of anaesthesia. Rimadyl (2 mg/kg body weight) was injected subcutaneously as an anti-inflammatory. Both eyes were covered with an eye ointment to prevent corneal desiccation during the experiment. The animal was head-fixed and a metal head-post cemented to the skull. A craniotomy of 4 mm in diameter was drilled over the V1 cortex. After the removal of the skull, the cortical surface was kept moist with a cortex buffer, containing: 125 mM NaCl, 5 mM KCl, 10 mM Glucose, 10 mM HEPES, 2 mM $MgSO_4$ and 2 mM $CaCl_2$, adjusted to pH 7.3. The cortex was then covered with a custom made plug coverslip (23) and sealed with Super Glue and dental cement. Mice were anaesthetized with 2% of isofluorane and mounted under a two-photon laser-scanning microscope (Multiphoton Imaging System, Scientifica Ltd., Uckfield, United Kingdom) equipped with a Ti:sapphire mode-locked laser (Mai Tai-Series, Spectra Physics) tuned at 920 nm. Imaging was performed through a water-immersion lens (Nikon, 16×, 0.8 NA) at a resolution of 256×256 pixels with zoom 2 or 4, leading to a field of view of 390×390 μm and 195×195 μm respectively. Data were acquired at 3.5 Hz. The objective was shielded with a black fabric cone equipped with a plastic o-ring fixed onto the head plate (24). Visual stimulation was controlled using a custom-made GUI in Python (based on PsychoPy toolbox) and was performed with a LED screen positioned 15 cm from the left eye of the mouse. Moving square-wave gratings were presented at 12 directions in 30 degrees steps and a photodiode was used to detect the starting and the ending time of each stimulus. Each grating direction was presented 5 times in random order alternated with a blank condition. The spatial frequency of the grating was 0.04 cycles per degree (cpd) and the temporal frequency was 1 Hz. Imaging and visual stimulation were triggered together using Arduino micro-controller board. Imaging session lasted up to 2 hrs and the power at sample was controlled in the range 30-40 mW. Data analysis was performed in ImageJ and Matlab and was restricted to cell bodies. Detection of region of interest (ROI) was performed with Suite2p. The relative changes in fluorescence were calculated as $dF/F_0=(F(t)-F_0)/(F_0)$. Orientation tuning curves were generated by taking the mean response for each orientation during the entire stimulus period. Response amplitudes are presented as the relative change in fluorescence during the stimulus period compared to the pre-stimulus baseline (dF/F). All data are presented as mean±SEM.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

The teaching of all references in the present application, including patent applications and granted patents, are herein fully incorporated by reference. Any patent application to which this application claims priority is incorporated by reference herein in its entirety in the manner described herein for publications and references.

For the avoidance of doubt the terms 'comprising', 'comprise' and 'comprises' herein is intended by the inventors to be optionally substitutable with the terms 'consisting of', 'consist of', and 'consists of', respectively, in every instance. The term "about" (or "around") in all numerical values allows for a 5% variation, i.e. a value of about 1.25% would mean from between 1.19%-1.31%.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the measurement, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The invention claimed is:

1. A rabies virus vector genome comprising a gene encoding a replication modulator protein, wherein the replication modulator protein comprises a viral protein moiety which is required for replication of the viral genome, and a regulator moiety, wherein the viral protein moiety is a rabies virus N (nucleoprotein) protein, wherein the regulator moiety comprises a protease cleavage site and a degron, wherein the degron is a PEST sequence, and wherein the protease cleavage site is located between the viral protein moiety and the degron, wherein the replication modulator protein is capable of adopting a targeted configuration displaying the degron, and an untargeted configuration which does not display the degron, and wherein the replication modulator protein is an inhibitory modulator switchable to the untargeted configuration on contact with a cognate activating agent, wherein the cognate activating agent is a protease, and wherein said vector is transcriptionally silent in the absence of the protease and transcriptionally active in the presence of the protease.

2. The vector genome of claim 1, (a) wherein the activating agent cleaves the regulator moiety from the viral protein moiety and/or (b) wherein the activating agent is encoded by the vector genome and wherein expression or function of the agent is inducible.

3. The vector genome of claim 1, wherein the protease does not act on any other proteins encoded by the vector genome; and/or wherein the protease is a viral protease, Factor Xa, enterokinase or thrombin.

4. A rabies virus vector genome comprising a gene encoding a replication modulator protein, wherein the replication modulator protein comprises a viral protein moiety which is required for replication of the viral genome, and a regulator moiety, wherein the viral protein moiety is a rabies virus N (nucleoprotein) protein, wherein the replication modulator protein encoded by the vector genome is an inhibitable modulator protein which is switchable to a targeted configuration displaying a degron on contact with a cognate inhibitory agent, wherein the replication modulator protein is capable of adopting a targeted configuration displaying the degron, and an untargeted configuration which does not display the degron, wherein the cognate inhibitory agent is a ligand for the regulator moiety, wherein the regulator moiety and cognate inhibitory agent are components of an inducible degron system, wherein:

(i) the regulator moiety comprises a modified haloalkane dehydrogenase and the cognate inhibitory agent is a ligand thereof (ii) the regulator moiety comprises a LID-FKBP sequence and the cognate inhibitory agent is a ligand therefor; or (iii) the regulator moiety comprises an auxin-inducible degron sequence and the cognate inhibitory agent is a ligand therefor;

wherein said vector is transcriptionally active in the absence of the cognate inhibitory agent and transcriptionally silent in the presence of the cognate inhibitory agent.

5. The vector genome of claim 4, wherein the protease does not act on any other proteins encoded by the vector genome.

6. The vector genome of claim 4, wherein the protease is a viral protease, Factor Xa, enterokinase or thrombin.

7. The vector genome of claim 4, wherein the cognate inhibitory agent is encoded by the vector genome and wherein expression or function of the cognate inhibitory agent is inducible.

8. The vector genome of claim 1, wherein the genome further comprises genes encoding a P protein, M protein, and/or L protein; and/or wherein the genome further comprises a gene encoding an envelope protein.

9. The vector genome of claim 8, wherein the envelope protein is native to the mononegaviral vector; or wherein the envelope protein is a pseudotyped envelope protein.

10. The vector genome of claim 1, wherein the vector genome does not encode an envelope protein; and/or wherein the vector genome further comprises one or more heterologous genes.

11. The vector genome of claim 10, wherein the heterologous gene encodes a marker protein, a recombinase, a nuclease, a guide RNA (gRNA) molecule, or a repair template RNA.

12. The vector genome of claim 11, wherein the nuclease is an RNA-guided endonuclease.

13. A ribonucleoprotein complex comprising the vector genome of claim 1 in association with one or more viral proteins.

14. The ribonucleoprotein complex of claim 13, wherein the ribonucleoprotein complex comprises the vector genome in association with N, P and L proteins; and/or wherein the ribonucleoprotein complex is a functional viral nucleocapsid, capable of initiating transcription on introduction to the cytoplasm of a target cell.

15. A method of gene delivery to a target cell, comprising contacting the target cell with a ribonucleoprotein complex comprising the vector genome of claim 1 in association with one or more viral proteins, or a virion comprising the vector genome of claim 1, wherein the target cell is a neural cell, and wherein:

a) the vector encodes an inhibitory modulator protein, and the method further comprises contacting the target cell with a cognate activating agent; or b) the vector encodes an inhibitory modulator protein and an activating agent, wherein expression or function of the activating agent is inducible, and wherein the method further comprises the step of inducing expression and/or function of the activating agent in the target cell.

16. The method of claim 15, (i) wherein the activating agent of part a) is a protein, and the method further comprises introducing into the target cell a nucleic acid comprising a gene encoding the activating agent, such that the activating agent is expressed in the target cell;

(ii) wherein expression and/or function of the agent is inducible, and the method further comprises the step of inducing expression and/or function of the agent in the target cell; or (iii) wherein the method further comprises contacting the target cell of part b) with a cognate inducer.

17. The method of claim 15, wherein the vector genome does not comprise a gene encoding an envelope protein, and the method further comprises the step of introducing into the target cell a nucleic acid construct comprising a gene encoding an envelope protein.

18. The vector genome of claim 12, wherein the RNA-guided endonuclease further comprises heterologous genes encoding a guide RNA (gRNA) molecule and/or a repair template RNA.

19. The vector genome of claim 4, wherein the genome further comprises genes encoding a P protein, M protein, and/or L protein; and/or wherein the genome further comprises a gene encoding an envelope protein.

20. The vector genome of claim 19, wherein the envelope protein is native to the mononegaviral vector; or wherein the envelope protein is a pseudotyped envelope protein.

21. The vector genome of claim 4, wherein the vector genome does not encode an envelope protein; and/or wherein the vector genome further comprises one or more heterologous genes.

22. The vector genome of claim 21, wherein the heterologous gene encodes a marker protein, a recombinase, a nuclease, a guide RNA (gRNA) molecule, or a repair template RNA.

23. The vector genome of claim 22, wherein the nuclease is an RNA-guided endonuclease.

24. The vector genome of claim 23, wherein the RNA-guided endonuclease further comprises heterologous genes encoding a guide RNA (gRNA) molecule and/or a repair template RNA.

25. A ribonucleoprotein complex comprising the vector genome of claim 4 in association with one or more viral proteins.

26. The ribonucleoprotein complex of claim 25, wherein the ribonucleoprotein complex comprises the vector genome in association with N, P and L proteins; and/or wherein the ribonucleoprotein complex is a functional viral nucleocapsid, capable of initiating transcription on introduction to the cytoplasm of a target cell.

27. A method of gene delivery to a target cell, comprising contacting the target cell with a ribonucleoprotein complex comprising the vector genome of claim 4 in association with one or more viral proteins, or a virion comprising the vector genome of claim 4, and wherein the target cell is a neural cell, and wherein:

a) the vector encodes an inhibitable modulator protein, and the method further comprises contacting the target cell with a cognate inhibitory agent; or b) the vector encodes an inhibitable modulator protein and an inhibitory agent, wherein expression or function of the inhibitory agent is inducible, and wherein the method further comprises the step of inducing expression and/or function of the inhibitory agent in the target cell.

28. The method of claim 27, (i) wherein the inhibitory agent of part a) is a protein, and the method further comprises introducing into the target cell a nucleic acid comprising a gene encoding the inhibitory agent, such that the inhibitory agent is expressed in the target cell;

(ii) wherein expression and/or function of the agent is inducible, and the method further comprises the step of inducing expression and/or function of the agent in the target cell; or (iii) wherein the method further comprises contacting the target cell of part b) with a cognate inducer.

29. The method of claim 28, wherein the vector genome does not comprise a gene encoding an envelope protein, and the method further comprises the step of introducing into the target cell a nucleic acid construct comprising a gene encoding an envelope protein.

* * * * *

SEQUENCE LISTING

```
<160> NUMBER OF SEQ ID NOS: 21

<210> SEQ ID NO 1
<211> LENGTH: 10
<212> TYPE: RNA
<213> ORGANISM: Artificial Sequence
<220> FEATURE:
<223> OTHER INFORMATION: transcriptional initiation signal consensus
      sequence
<220> FEATURE:
<221> NAME/KEY: misc_feature
<222> LOCATION: (10)..(10)
<223> OTHER INFORMATION: N = A or U

<400> SEQUENCE: 1

guuuuuuucn                                                            10


<210> SEQ ID NO 2
<211> LENGTH: 450
<212> TYPE: PRT
<213> ORGANISM: Artificial Sequence
<220> FEATURE:
<223> OTHER INFORMATION: Rabies N protein

<400> SEQUENCE: 2

Met Asp Ala Asp Lys Ile Val Phe Lys Val Asn Asn Gln Val Val Ser
1               5                   10                  15

Leu Lys Pro Glu Ile Ile Val Asp Gln Tyr Glu Tyr Lys Tyr Pro Ala
            20                  25                  30

Ile Lys Asp Leu Lys Lys Pro Cys Ile Thr Leu Gly Lys Ala Pro Asp
        35                  40                  45

Leu Asn Lys Ala Tyr Lys Ser Val Leu Ser Gly Met Ser Ala Ala Lys
    50                  55                  60

Leu Asn Pro Asp Asp Val Cys Ser Tyr Leu Ala Ala Ala Met Gln Phe
65                  70                  75                  80

Phe Glu Gly Thr Cys Pro Glu Asp Trp Thr Ser Tyr Gly Ile Val Ile
                85                  90                  95
```

```
Ala Arg Lys Gly Asp Lys Ile Thr Pro Gly Ser Leu Val Glu Ile Lys
            100                 105                 110

Arg Thr Asp Val Glu Gly Asn Trp Ala Leu Thr Gly Gly Met Glu Leu
        115                 120                 125

Thr Arg Asp Pro Thr Val Pro Glu His Ala Ser Leu Val Gly Leu Leu
    130                 135                 140

Leu Ser Leu Tyr Arg Leu Ser Lys Ile Ser Gly Gln Asn Thr Gly Asn
145                 150                 155                 160

Tyr Lys Thr Asn Ile Ala Asp Arg Ile Glu Gln Ile Phe Glu Thr Ala
                165                 170                 175

Pro Phe Val Lys Ile Val Glu His His Thr Leu Met Thr Thr His Lys
            180                 185                 190

Met Cys Ala Asn Trp Ser Thr Ile Pro Asn Phe Arg Phe Leu Ala Gly
        195                 200                 205

Thr Tyr Asp Met Phe Phe Ser Arg Ile Glu His Leu Tyr Ser Ala Ile
    210                 215                 220

Arg Val Gly Thr Val Val Thr Ala Tyr Glu Asp Cys Ser Gly Leu Val
225                 230                 235                 240

Ser Phe Thr Gly Phe Ile Lys Gln Ile Asn Leu Thr Ala Arg Glu Ala
                245                 250                 255

Ile Leu Tyr Phe Phe His Lys Asn Phe Glu Glu Glu Ile Arg Arg Met
            260                 265                 270

Phe Glu Pro Gly Gln Glu Thr Ala Val Pro His Ser Tyr Phe Ile His
        275                 280                 285

Phe Arg Ser Leu Gly Leu Ser Gly Lys Ser Pro Tyr Ser Ser Asn Ala
    290                 295                 300

Val Gly His Val Phe Asn Leu Ile His Phe Val Gly Cys Tyr Met Gly
305                 310                 315                 320

Gln Val Arg Ser Leu Asn Ala Thr Val Ile Ala Ala Cys Ala Pro His
                325                 330                 335

Glu Met Ser Val Leu Gly Gly Tyr Leu Gly Glu Glu Phe Phe Gly Lys
            340                 345                 350

Gly Thr Phe Glu Arg Arg Phe Phe Arg Asp Glu Lys Glu Leu Gln Glu
        355                 360                 365

Tyr Glu Ala Ala Glu Leu Thr Lys Thr Asp Val Ala Leu Ala Asp Asp
    370                 375                 380

Gly Thr Val Asn Ser Asp Asp Glu Asp Tyr Phe Ser Gly Glu Thr Arg
385                 390                 395                 400

Ser Pro Glu Ala Val Tyr Thr Arg Ile Met Met Asn Gly Gly Arg Leu
                405                 410                 415

Lys Arg Ser His Ile Arg Arg Tyr Val Ser Val Ser Ser Asn His Gln
            420                 425                 430

Ala Arg Pro Asn Ser Phe Ala Glu Phe Leu Asn Lys Thr Tyr Ser Ser
        435                 440                 445

Asp Ser
    450
```

<210> SEQ ID NO 3
<211> LENGTH: 297
<212> TYPE: PRT
<213> ORGANISM: Artificial Sequence
<220> FEATURE:
<223> OTHER INFORMATION: Rabies P protein

<400> SEQUENCE: 3

Met Ser Lys Ile Phe Val Asn Pro Ser Ala Ile Arg Ala Gly Leu Ala
1               5                   10                  15

Asp Leu Glu Met Ala Glu Glu Thr Val Asp Leu Ile Asn Arg Asn Ile
            20                  25                  30

Glu Asp Asn Gln Ala His Leu Gln Gly Glu Pro Ile Glu Val Asp Asn
        35                  40                  45

Leu Pro Glu Asp Met Gly Arg Leu His Leu Asp Asp Gly Lys Ser Pro
    50                  55                  60

Asn His Gly Glu Ile Ala Lys Val Gly Glu Gly Lys Tyr Arg Glu Asp
65                  70                  75                  80

Phe Gln Met Asp Glu Gly Glu Asp Pro Ser Phe Leu Phe Gln Ser Tyr
                85                  90                  95

Leu Glu Asn Val Gly Val Gln Ile Val Arg Gln Met Arg Ser Gly Glu
            100                 105                 110

Arg Phe Leu Lys Ile Trp Ser Gln Thr Val Glu Glu Ile Ile Ser Tyr
        115                 120                 125

Val Ala Val Asn Phe Pro Asn Pro Pro Gly Lys Ser Ser Glu Asp Lys
    130                 135                 140

Ser Thr Gln Thr Thr Gly Arg Glu Leu Lys Lys Glu Thr Thr Pro Thr
145                 150                 155                 160

Pro Ser Gln Arg Glu Ser Gln Ser Ser Lys Ala Arg Met Ala Ala Gln
                165                 170                 175

Ile Ala Ser Gly Pro Pro Ala Leu Glu Trp Ser Ala Thr Asn Glu Glu
            180                 185                 190

Asp Asp Leu Ser Val Glu Ala Glu Ile Ala His Gln Ile Ala Glu Ser
        195                 200                 205

Phe Ser Lys Lys Tyr Lys Phe Pro Ser Arg Ser Ser Gly Ile Leu Leu
    210                 215                 220

Tyr Asn Phe Glu Gln Leu Lys Met Asn Leu Asp Asp Ile Val Lys Glu
225                 230                 235                 240

Ala Lys Asn Val Pro Gly Val Thr Arg Leu Ala His Asp Gly Ser Lys
                245                 250                 255

Leu Pro Leu Arg Cys Val Leu Gly Trp Val Ala Leu Ala Asn Ser Lys
            260                 265                 270

Lys Phe Gln Leu Leu Val Glu Ser Asp Lys Leu Ser Lys Ile Met Gln
        275                 280                 285

Asp Asp Leu Asn Arg Tyr Thr Ser Cys
    290                 295

<210> SEQ ID NO 4
<211> LENGTH: 202
<212> TYPE: PRT
<213> ORGANISM: Artificial Sequence
<220> FEATURE:
<223> OTHER INFORMATION: Rabies M protein

<400> SEQUENCE: 4

Met Asn Leu Leu Arg Lys Ile Val Lys Asn Arg Arg Asp Glu Asp Thr
1               5                   10                  15

Gln Lys Ser Ser Pro Ala Ser Ala Pro Leu Asp Asp Asp Asp Leu Trp
            20                  25                  30

Leu Pro Pro Pro Glu Tyr Val Pro Leu Lys Glu Leu Thr Gly Lys Lys
        35                  40                  45

```
Asn Met Arg Asn Phe Cys Ile Asn Gly Arg Val Lys Val Cys Ser Pro
    50                  55                  60

Asn Gly Tyr Ser Phe Arg Ile Leu Arg His Ile Leu Lys Ser Phe Asp
65                  70                  75                  80

Glu Ile Tyr Ser Gly Asn His Arg Met Ile Gly Leu Val Lys Val Val
                85                  90                  95

Ile Gly Leu Ala Leu Ser Gly Ser Pro Val Pro Glu Gly Leu Asn Trp
            100                 105                 110

Val Tyr Lys Leu Arg Arg Thr Phe Ile Phe Gln Trp Ala Asp Ser Arg
        115                 120                 125

Gly Pro Leu Glu Gly Glu Glu Leu Glu Tyr Ser Gln Glu Ile Thr Trp
    130                 135                 140

Asp Asp Asp Thr Glu Phe Val Gly Leu Gln Ile Arg Val Ile Ala Lys
145                 150                 155                 160

Gln Cys His Ile Gln Gly Arg Val Trp Cys Ile Asn Met Asn Pro Arg
                165                 170                 175

Ala Cys Gln Leu Trp Ser Asp Met Ser Leu Gln Thr Gln Arg Ser Glu
            180                 185                 190

Glu Asp Lys Asp Ser Ser Leu Leu Leu Glu
        195                 200


<210> SEQ ID NO 5
<211> LENGTH: 2127
<212> TYPE: PRT
<213> ORGANISM: Artificial Sequence
<220> FEATURE:
<223> OTHER INFORMATION: Rabies L protein

<400> SEQUENCE: 5

Met Leu Asp Pro Gly Glu Val Tyr Asp Asp Pro Ile Asp Pro Ile Glu
1               5                   10                  15

Leu Glu Ala Glu Pro Arg Gly Thr Pro Ile Val Pro Asn Ile Leu Arg
            20                  25                  30

Asn Ser Asp Tyr Asn Leu Asn Ser Pro Leu Ile Glu Asp Pro Ala Arg
        35                  40                  45

Leu Met Leu Glu Trp Leu Lys Thr Gly Asn Arg Pro Tyr Arg Met Thr
    50                  55                  60

Leu Thr Asp Asn Cys Ser Arg Ser Phe Arg Val Leu Lys Asp Tyr Phe
65                  70                  75                  80

Lys Lys Val Asp Leu Gly Ser Leu Lys Val Gly Gly Met Ala Ala Gln
                85                  90                  95

Ser Met Ile Ser Leu Trp Leu Tyr Gly Ala His Ser Glu Ser Asn Arg
            100                 105                 110

Ser Arg Arg Cys Ile Thr Asp Leu Ala His Phe Tyr Ser Lys Ser Ser
        115                 120                 125

Pro Ile Glu Lys Leu Leu Asn Leu Thr Leu Gly Asn Arg Gly Leu Arg
    130                 135                 140

Ile Pro Pro Glu Gly Val Leu Ser Cys Leu Glu Arg Val Asp Tyr Asp
145                 150                 155                 160

Asn Ala Phe Gly Arg Tyr Leu Ala Asn Thr Tyr Ser Ser Tyr Leu Phe
                165                 170                 175

Phe His Val Ile Thr Leu Tyr Met Asn Ala Leu Asp Trp Asp Glu Glu
            180                 185                 190

Lys Thr Ile Leu Ala Leu Trp Lys Asp Leu Thr Ser Val Asp Ile Gly
        195                 200                 205
```

-continued

```
Lys Asp Leu Val Lys Phe Lys Asp Gln Ile Trp Gly Leu Leu Ile Val
    210                 215                 220

Thr Lys Asp Phe Val Tyr Ser Gln Ser Ser Asn Cys Leu Phe Asp Arg
225                 230                 235                 240

Asn Tyr Thr Leu Met Leu Lys Asp Leu Phe Leu Ser Arg Phe Asn Ser
                245                 250                 255

Leu Met Val Leu Leu Ser Pro Pro Glu Pro Arg Tyr Ser Asp Asp Leu
            260                 265                 270

Ile Ser Gln Leu Cys Gln Leu Tyr Ile Ala Gly Asp Gln Val Leu Ser
        275                 280                 285

Met Cys Gly Asn Ser Gly Tyr Glu Val Ile Lys Ile Leu Glu Pro Tyr
    290                 295                 300

Val Val Asn Ser Leu Val Gln Arg Ala Glu Lys Phe Arg Pro Leu Ile
305                 310                 315                 320

His Ser Leu Gly Asp Phe Pro Val Phe Ile Lys Asp Lys Val Ser Gln
                325                 330                 335

Leu Glu Glu Thr Phe Gly Pro Cys Ala Arg Arg Phe Phe Arg Ala Leu
            340                 345                 350

Asp Gln Phe Asp Asn Ile His Asp Leu Val Phe Val Phe Gly Cys Tyr
        355                 360                 365

Arg His Trp Gly His Pro Tyr Ile Asp Tyr Arg Lys Gly Leu Ser Lys
    370                 375                 380

Leu Tyr Asp Gln Val His Leu Lys Lys Met Ile Asp Lys Ser Tyr Gln
385                 390                 395                 400

Glu Cys Leu Ala Ser Asp Leu Ala Arg Arg Ile Leu Arg Trp Gly Phe
                405                 410                 415

Asp Lys Tyr Ser Lys Trp Tyr Leu Asp Ser Arg Phe Leu Ala Arg Asp
            420                 425                 430

His Pro Leu Thr Pro Tyr Ile Lys Thr Gln Thr Trp Pro Pro Lys His
        435                 440                 445

Ile Val Asp Leu Val Gly Asp Thr Trp His Lys Leu Pro Ile Thr Gln
    450                 455                 460

Ile Phe Glu Ile Pro Glu Ser Met Asp Pro Ser Glu Ile Leu Asp Asp
465                 470                 475                 480

Lys Ser His Ser Phe Thr Arg Thr Arg Leu Ala Ser Trp Leu Ser Glu
                485                 490                 495

Asn Arg Gly Gly Pro Val Pro Ser Glu Lys Val Ile Ile Thr Ala Leu
            500                 505                 510

Ser Lys Pro Pro Val Asn Pro Arg Glu Phe Leu Arg Ser Ile Asp Leu
        515                 520                 525

Gly Gly Leu Pro Asp Glu Asp Leu Ile Ile Gly Leu Lys Pro Lys Glu
    530                 535                 540

Arg Glu Leu Lys Ile Glu Gly Arg Phe Phe Ala Leu Met Ser Trp Asn
545                 550                 555                 560

Leu Arg Leu Tyr Phe Val Ile Thr Glu Lys Leu Leu Ala Asn Tyr Ile
                565                 570                 575

Leu Pro Leu Phe Asp Ala Leu Thr Met Thr Asp Asn Leu Asn Lys Val
            580                 585                 590

Phe Lys Lys Leu Ile Asp Arg Val Thr Gly Gln Gly Leu Leu Asp Tyr
        595                 600                 605

Ser Arg Val Thr Tyr Ala Phe His Leu Asp Tyr Glu Lys Trp Asn Asn
    610                 615                 620
```

-continued

```
His Gln Arg Leu Glu Ser Thr Glu Asp Val Phe Ser Val Leu Asp Gln
625                 630                 635                 640

Val Phe Gly Leu Lys Arg Val Phe Ser Arg Thr His Glu Phe Phe Gln
                645                 650                 655

Lys Ala Trp Ile Tyr Tyr Ser Asp Arg Ser Asp Leu Ile Gly Leu Arg
            660                 665                 670

Glu Asp Gln Ile Tyr Cys Leu Asp Ala Ser Asn Gly Pro Thr Cys Trp
        675                 680                 685

Asn Gly Gln Asp Gly Gly Leu Glu Gly Leu Arg Gln Lys Gly Trp Ser
    690                 695                 700

Leu Val Ser Leu Leu Met Ile Asp Arg Glu Ser Gln Ile Arg Asn Thr
705                 710                 715                 720

Arg Thr Lys Ile Leu Ala Gln Gly Asp Asn Gln Val Leu Cys Pro Thr
                725                 730                 735

Tyr Met Leu Ser Pro Gly Leu Ser Gln Glu Gly Leu Leu Tyr Glu Leu
            740                 745                 750

Glu Arg Ile Ser Arg Asn Ala Leu Ser Ile Tyr Arg Ala Val Glu Glu
        755                 760                 765

Gly Ala Ser Lys Leu Gly Leu Ile Ile Lys Lys Glu Glu Thr Met Cys
    770                 775                 780

Ser Tyr Asp Phe Leu Ile Tyr Gly Lys Thr Pro Leu Phe Arg Gly Asn
785                 790                 795                 800

Ile Leu Val Pro Glu Ser Lys Arg Trp Ala Arg Val Ser Cys Val Ser
                805                 810                 815

Asn Asp Gln Ile Val Asn Leu Ala Asn Ile Met Ser Thr Val Ser Thr
            820                 825                 830

Asn Ala Leu Thr Val Ala Gln His Ser Gln Ser Leu Ile Lys Pro Met
        835                 840                 845

Arg Asp Phe Leu Leu Met Ser Val Gln Ala Val Phe His Tyr Leu Leu
    850                 855                 860

Phe Ser Pro Ile Leu Lys Gly Arg Val Tyr Lys Ile Leu Ser Ala Glu
865                 870                 875                 880

Gly Glu Ser Phe Leu Leu Ala Met Ser Arg Ile Ile Tyr Leu Asp Pro
                885                 890                 895

Ser Leu Gly Gly Ile Ser Gly Met Ser Leu Gly Arg Phe His Ile Arg
            900                 905                 910

Gln Phe Ser Asp Pro Val Ser Glu Gly Leu Ser Phe Trp Arg Glu Ile
        915                 920                 925

Trp Leu Ser Ser Gln Glu Ser Trp Ile His Ala Leu Cys Gln Glu Ala
    930                 935                 940

Gly Asn Pro Asp Leu Gly Glu Arg Thr Leu Glu Ser Phe Thr Arg Leu
945                 950                 955                 960

Leu Glu Asp Pro Thr Thr Leu Asn Ile Arg Gly Gly Ala Ser Pro Thr
                965                 970                 975

Ile Leu Leu Lys Asp Ala Ile Arg Lys Ala Leu Tyr Asp Glu Val Asp
            980                 985                 990

Lys Val Glu Asn Ser Glu Phe Arg  Glu Ala Ile Leu Leu  Ser Lys Thr
        995                 1000                1005

His Arg  Asp Asn Phe Ile Leu  Phe Leu Ile Ser Val  Glu Pro Leu
    1010                1015                1020

Phe Pro  Arg Phe Leu Ser Glu  Leu Phe Ser Ser Ser  Phe Leu Gly
    1025                1030                1035
```

-continued

```
Ile Pro  Glu Ser Ile Ile Gly  Leu Ile Gln Asn Ser  Arg Thr Ile
    1040                 1045                 1050

Arg Arg  Gln Phe Arg Lys Ser  Leu Ser Lys Thr Leu  Glu Glu Ser
    1055                 1060                 1065

Phe Tyr  Asn Ser Glu Ile His  Gly Ile Ser Arg Met  Thr Gln Thr
    1070                 1075                 1080

Pro Gln  Arg Val Gly Gly Val  Trp Pro Cys Ser Ser  Glu Arg Ala
    1085                 1090                 1095

Asp Leu  Leu Arg Glu Ile Ser  Trp Gly Arg Lys Val  Val Gly Thr
    1100                 1105                 1110

Thr Val  Pro His Pro Ser Glu  Met Leu Gly Leu Leu  Pro Lys Ser
    1115                 1120                 1125

Ser Ile  Ser Cys Thr Cys Gly  Ala Thr Gly Gly Gly  Asn Pro Arg
    1130                 1135                 1140

Val Ser  Val Ser Val Leu Pro  Ser Phe Asp Gln Ser  Phe Phe Ser
    1145                 1150                 1155

Arg Gly  Pro Leu Lys Gly Tyr  Leu Gly Ser Ser Thr  Ser Met Ser
    1160                 1165                 1170

Thr Gln  Leu Phe His Ala Trp  Glu Lys Val Thr Asn  Val His Val
    1175                 1180                 1185

Val Lys  Arg Ala Leu Ser Leu  Lys Glu Ser Ile Asn  Trp Phe Ile
    1190                 1195                 1200

Thr Arg  Asp Ser Asn Leu Ala  Gln Ala Leu Ile Arg  Asn Ile Met
    1205                 1210                 1215

Ser Leu  Thr Gly Pro Asp Phe  Pro Leu Glu Glu Ala  Pro Val Phe
    1220                 1225                 1230

Lys Arg  Thr Gly Ser Ala Leu  His Arg Phe Lys Ser  Ala Arg Tyr
    1235                 1240                 1245

Ser Glu  Gly Gly Tyr Ser Ser  Val Cys Pro Asn Leu  Leu Ser His
    1250                 1255                 1260

Ile Ser  Val Ser Thr Asp Thr  Met Ser Asp Leu Thr  Gln Asp Gly
    1265                 1270                 1275

Lys Asn  Tyr Asp Phe Met Phe  Gln Pro Leu Met Leu  Tyr Ala Gln
    1280                 1285                 1290

Thr Trp  Thr Ser Glu Leu Val  Gln Arg Asp Thr Arg  Leu Arg Asp
    1295                 1300                 1305

Ser Thr  Phe His Trp His Leu  Arg Cys Asn Arg Cys  Val Arg Pro
    1310                 1315                 1320

Ile Asp  Asp Val Thr Leu Glu  Thr Ser Gln Ile Phe  Glu Phe Pro
    1325                 1330                 1335

Asp Val  Ser Lys Arg Ile Ser  Arg Met Val Ser Gly  Ala Val Pro
    1340                 1345                 1350

His Phe  Gln Arg Leu Pro Asp  Ile Arg Leu Arg Pro  Gly Asp Phe
    1355                 1360                 1365

Glu Ser  Leu Ser Gly Arg Glu  Lys Ser His His Ile  Gly Ser Ala
    1370                 1375                 1380

Gln Gly  Leu Leu Tyr Ser Ile  Leu Val Ala Ile His  Asp Ser Gly
    1385                 1390                 1395

Tyr Asn  Asp Gly Thr Ile Phe  Pro Val Asn Ile Tyr  Gly Lys Val
    1400                 1405                 1410

Ser Pro  Arg Asp Tyr Leu Arg  Gly Leu Ala Arg Gly  Val Leu Ile
    1415                 1420                 1425
```

```
Gly Ser  Ser Ile Cys Phe Leu  Thr Arg Met Thr Asn  Ile Asn Ile
    1430                 1435                 1440

Asn Arg  Pro Leu Glu Leu Val  Ser Gly Val Ile Ser  Tyr Ile Leu
    1445                 1450                 1455

Leu Arg  Leu Asp Asn His Pro  Ser Leu Tyr Ile Met  Leu Arg Glu
    1460                 1465                 1470

Pro Ser  Leu Arg Gly Glu Ile  Phe Ser Ile Pro Gln  Lys Ile Pro
    1475                 1480                 1485

Ala Ala  Tyr Pro Thr Thr Met  Lys Glu Gly Asn Arg  Ser Ile Leu
    1490                 1495                 1500

Cys Tyr  Leu Gln His Val Leu  Arg Tyr Glu Arg Glu  Ile Ile Thr
    1505                 1510                 1515

Ala Ser  Pro Glu Asn Asp Trp  Leu Trp Ile Phe Ser  Asp Phe Arg
    1520                 1525                 1530

Ser Ala  Lys Met Thr Tyr Leu  Ser Leu Ile Thr Tyr  Gln Ser His
    1535                 1540                 1545

Leu Leu  Leu Gln Arg Val Glu  Arg Asn Leu Ser Lys  Ser Met Arg
    1550                 1555                 1560

Asp Asn  Leu Arg Gln Leu Ser  Ser Leu Met Arg Gln  Val Leu Gly
    1565                 1570                 1575

Gly His  Gly Glu Asp Thr Leu  Glu Ser Asp Asp Asn  Ile Gln Arg
    1580                 1585                 1590

Leu Leu  Lys Asp Ser Leu Arg  Arg Thr Arg Trp Val  Asp Gln Glu
    1595                 1600                 1605

Val Arg  His Ala Ala Arg Thr  Met Thr Gly Asp Tyr  Ser Pro Asn
    1610                 1615                 1620

Lys Lys  Val Ser Arg Lys Val  Gly Cys Ser Glu Trp  Val Cys Ser
    1625                 1630                 1635

Ala Gln  Gln Val Ala Val Ser  Thr Ser Ala Asn Pro  Ala Pro Val
    1640                 1645                 1650

Ser Glu  Leu Asp Ile Arg Ala  Leu Ser Lys Arg Phe  Gln Asn Pro
    1655                 1660                 1665

Leu Ile  Ser Gly Leu Arg Val  Val Gln Trp Ala Thr  Gly Ala His
    1670                 1675                 1680

Tyr Lys  Leu Lys Pro Ile Leu  Asp Asp Leu Asn Val  Phe Pro Ser
    1685                 1690                 1695

Leu Cys  Leu Val Val Gly Asp  Gly Ser Gly Gly Ile  Ser Arg Ala
    1700                 1705                 1710

Val Leu  Asn Met Phe Pro Asp  Ala Lys Leu Val Phe  Asn Ser Leu
    1715                 1720                 1725

Leu Glu  Val Asn Asp Leu Met  Ala Ser Gly Thr His  Pro Leu Pro
    1730                 1735                 1740

Pro Ser  Ala Ile Met Arg Gly  Gly Asn Asp Ile Val  Ser Arg Val
    1745                 1750                 1755

Ile Asp  Leu Asp Ser Ile Trp  Glu Lys Pro Ser Asp  Leu Arg Asn
    1760                 1765                 1770

Leu Ala  Thr Trp Lys Tyr Phe  Gln Ser Val Gln Lys  Gln Val Asn
    1775                 1780                 1785

Met Ser  Tyr Asp Leu Ile Ile  Cys Asp Ala Glu Val  Thr Asp Ile
    1790                 1795                 1800

Ala Ser  Ile Asn Arg Ile Thr  Leu Leu Met Ser Asp  Phe Ala Leu
    1805                 1810                 1815
```

Ser Ile Asp Gly Pro Leu Tyr Leu Val Phe Lys Thr Tyr Gly Thr
1820 1825 1830

Met Leu Val Asn Pro Asn Tyr Lys Ala Ile Gln His Leu Ser Arg
1835 1840 1845

Ala Phe Pro Ser Val Thr Gly Phe Ile Thr Gln Val Thr Ser Ser
1850 1855 1860

Phe Ser Ser Glu Leu Tyr Leu Arg Phe Ser Lys Arg Gly Lys Phe
1865 1870 1875

Phe Arg Asp Ala Glu Tyr Leu Thr Ser Ser Thr Leu Arg Glu Met
1880 1885 1890

Ser Leu Val Leu Phe Asn Cys Ser Ser Pro Lys Ser Glu Met Gln
1895 1900 1905

Arg Ala Arg Ser Leu Asn Tyr Gln Asp Leu Val Arg Gly Phe Pro
1910 1915 1920

Glu Glu Ile Ile Ser Asn Pro Tyr Asn Glu Met Ile Ile Thr Leu
1925 1930 1935

Ile Asp Ser Asp Val Glu Ser Phe Leu Val His Lys Met Val Asp
1940 1945 1950

Asp Leu Glu Leu Gln Arg Gly Thr Leu Ser Lys Val Ala Ile Ile
1955 1960 1965

Ile Ala Ile Met Ile Val Phe Ser Asn Arg Val Phe Asn Val Ser
1970 1975 1980

Lys Pro Leu Thr Asp Pro Ser Phe Tyr Pro Pro Ser Asp Pro Lys
1985 1990 1995

Ile Leu Arg His Phe Asn Ile Cys Cys Ser Thr Met Met Tyr Leu
2000 2005 2010

Ser Thr Ala Leu Gly Asp Val Pro Ser Phe Ala Arg Leu His Asp
2015 2020 2025

Leu Tyr Asn Arg Pro Ile Thr Tyr Tyr Phe Arg Lys Gln Val Ile
2030 2035 2040

Arg Gly Asn Val Tyr Leu Ser Trp Ser Trp Ser Asn Asp Thr Ser
2045 2050 2055

Val Phe Lys Arg Val Ala Cys Asn Ser Ser Leu Ser Leu Ser Ser
2060 2065 2070

His Trp Ile Arg Leu Ile Tyr Lys Ile Val Lys Thr Thr Arg Leu
2075 2080 2085

Val Gly Ser Ile Lys Asp Leu Ser Arg Glu Val Glu Arg His Leu
2090 2095 2100

His Arg Tyr Asn Arg Trp Ile Thr Leu Glu Asp Ile Arg Ser Arg
2105 2110 2115

Ser Ser Leu Leu Asp Tyr Ser Cys Leu
2120 2125

<210> SEQ ID NO 6
<211> LENGTH: 524
<212> TYPE: PRT
<213> ORGANISM: Artificial Sequence
<220> FEATURE:
<223> OTHER INFORMATION: Rabies G protein

<400> SEQUENCE: 6

Met Val Pro Gln Ala Leu Leu Phe Val Pro Leu Leu Val Phe Pro Leu
1 5 10 15

Cys Phe Gly Lys Phe Pro Ile Tyr Thr Ile Pro Asp Lys Leu Gly Pro
20 25 30

-continued

```
Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr Arg Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ser Met Gln Thr Ser Asn Glu Thr Lys Trp Cys Pro
            260                 265                 270

Pro Asp Lys Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445
```

-continued

```
Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
        515                 520


<210> SEQ ID NO 7
<211> LENGTH: 524
<212> TYPE: PRT
<213> ORGANISM: Artificial Sequence
<220> FEATURE:
<223> OTHER INFORMATION: Optimised G protein

<400> SEQUENCE: 7

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Ser Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Pro Val Phe Pro Gly Gly
                165                 170                 175

Asn Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Gly Gln Leu Val Asn Leu His Asp Phe Arg Ser Asp Glu Ile Glu
        275                 280                 285
```

His Leu Val Val Glu Glu Leu Val Lys Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Val Ser Ser Val Ile Pro Leu Met His
                405                 410                 415

Pro Leu Ala Asp Pro Ser Thr Val Phe Lys Asn Gly Asp Glu Ala Glu
            420                 425                 430

Asp Phe Val Glu Val His Leu Pro Asp Val His Glu Arg Ile Ser Gly
        435                 440                 445

Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Trp
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
        515                 520

<210> SEQ ID NO 8
<211> LENGTH: 28
<212> TYPE: PRT
<213> ORGANISM: Artificial Sequence
<220> FEATURE:
<223> OTHER INFORMATION: PEST sequence

<400> SEQUENCE: 8

His Gly Phe Pro Pro Glu Val Glu Glu Gln Asp Asp Gly Thr Leu Pro
1               5                   10                  15

Met Ser Cys Ala Gln Glu Ser Gly Met Asp Arg His
            20                  25

<210> SEQ ID NO 9
<211> LENGTH: 40
<212> TYPE: PRT
<213> ORGANISM: Artificial Sequence
<220> FEATURE:
<223> OTHER INFORMATION: mODC(422-461)

<400> SEQUENCE: 9

Ser His Gly Phe Pro Pro Glu Val Glu Glu Gln Asp Asp Gly Thr Leu
1               5                   10                  15

Pro Met Ser Cys Ala Gln Glu Ser Gly Met Asp Arg His Pro Ala Ala
            20                  25                  30

Cys Ala Ser Ala Arg Ile Asn Val
35 40

<210> SEQ ID NO 10
<211> LENGTH: 34
<212> TYPE: PRT
<213> ORGANISM: Artificial Sequence
<220> FEATURE:
<223> OTHER INFORMATION: C-terminal region of NPDC-1

<400> SEQUENCE: 10

Lys Glu Leu Asp Thr Ala Ser Ser Asp Glu Glu Asn Glu Asp Gly Asp
1 5 10 15

Phe Thr Val Tyr Glu Cys Pro Gly Leu Ala Pro Thr Gly Glu Met Glu
20 25 30

Val Arg

<210> SEQ ID NO 11
<211> LENGTH: 503
<212> TYPE: PRT
<213> ORGANISM: Artificial Sequence
<220> FEATURE:
<223> OTHER INFORMATION: N-TEV-PEST

<400> SEQUENCE: 11

Met Asp Ala Asp Lys Ile Val Phe Lys Val Asn Asn Gln Val Val Ser
1 5 10 15

Leu Lys Pro Glu Ile Ile Val Asp Gln Tyr Glu Tyr Lys Tyr Pro Ala
20 25 30

Ile Lys Asp Leu Lys Lys Pro Cys Ile Thr Leu Gly Lys Ala Pro Asp
35 40 45

Leu Asn Lys Ala Tyr Lys Ser Val Leu Ser Gly Met Ser Ala Ala Lys
50 55 60

Leu Asn Pro Asp Asp Val Cys Ser Tyr Leu Ala Ala Ala Met Gln Phe
65 70 75 80

Phe Glu Gly Thr Cys Pro Glu Asp Trp Thr Ser Tyr Gly Ile Val Ile
85 90 95

Ala Arg Lys Gly Asp Lys Ile Thr Pro Gly Ser Leu Val Glu Ile Lys
100 105 110

Arg Thr Asp Val Glu Gly Asn Trp Ala Leu Thr Gly Gly Met Glu Leu
115 120 125

Thr Arg Asp Pro Thr Val Pro Glu His Ala Ser Leu Val Gly Leu Leu
130 135 140

Leu Ser Leu Tyr Arg Leu Ser Lys Ile Ser Gly Gln Asn Thr Gly Asn
145 150 155 160

Tyr Lys Thr Asn Ile Ala Asp Arg Ile Glu Gln Ile Phe Glu Thr Ala
165 170 175

Pro Phe Val Lys Ile Val Glu His His Thr Leu Met Thr Thr His Lys
180 185 190

Met Cys Ala Asn Trp Ser Thr Ile Pro Asn Phe Arg Phe Leu Ala Gly
195 200 205

Thr Tyr Asp Met Phe Phe Ser Arg Ile Glu His Leu Tyr Ser Ala Ile
210 215 220

Arg Val Gly Thr Val Val Thr Ala Tyr Glu Asp Cys Ser Gly Leu Val
225 230 235 240

Ser Phe Thr Gly Phe Ile Lys Gln Ile Asn Leu Thr Ala Arg Glu Ala
245 250 255

```
Ile Leu Tyr Phe Phe His Lys Asn Phe Glu Glu Glu Ile Arg Arg Met
            260                 265                 270

Phe Glu Pro Gly Gln Glu Thr Ala Val Pro His Ser Tyr Phe Ile His
        275                 280                 285

Phe Arg Ser Leu Gly Leu Ser Gly Lys Ser Pro Tyr Ser Ser Asn Ala
    290                 295                 300

Val Gly His Val Phe Asn Leu Ile His Phe Val Gly Cys Tyr Met Gly
305                 310                 315                 320

Gln Val Arg Ser Leu Asn Ala Thr Val Ile Ala Ala Cys Ala Pro His
                325                 330                 335

Glu Met Ser Val Leu Gly Gly Tyr Leu Gly Glu Glu Phe Phe Gly Lys
            340                 345                 350

Gly Thr Phe Glu Arg Arg Phe Phe Arg Asp Glu Lys Glu Leu Gln Glu
        355                 360                 365

Tyr Glu Ala Ala Glu Leu Thr Lys Thr Asp Val Ala Leu Ala Asp Asp
    370                 375                 380

Gly Thr Val Asn Ser Asp Asp Glu Asp Tyr Phe Ser Gly Glu Thr Arg
385                 390                 395                 400

Ser Pro Glu Ala Val Tyr Thr Arg Ile Met Met Asn Gly Gly Arg Leu
                405                 410                 415

Lys Arg Ser His Ile Arg Arg Tyr Val Ser Val Ser Ser Asn His Gln
            420                 425                 430

Ala Arg Pro Asn Ser Phe Ala Glu Phe Leu Asn Lys Thr Tyr Ser Ser
        435                 440                 445

Asp Ser Gly Ser Gly Glu Asn Leu Tyr Phe Gln Ser Gly Ser Gly Ser
    450                 455                 460

His Gly Phe Pro Pro Glu Val Glu Glu Gln Asp Asp Gly Thr Leu Pro
465                 470                 475                 480

Met Ser Cys Ala Gln Glu Ser Gly Met Asp Arg His Pro Ala Ala Cys
                485                 490                 495

Ala Ser Ala Arg Ile Asn Val
            500
```

<210> SEQ ID NO 12
<211> LENGTH: 19
<212> TYPE: PRT
<213> ORGANISM: Artificial Sequence
<220> FEATURE:
<223> OTHER INFORMATION: synthetic degron

<400> SEQUENCE: 12

```
Thr Arg Gly Val Glu Glu Val Ala Glu Gly Val Val Leu Leu Arg Arg
1               5                   10                  15

Arg Gly Asn
```

<210> SEQ ID NO 13
<211> LENGTH: 7
<212> TYPE: PRT
<213> ORGANISM: Artificial Sequence
<220> FEATURE:
<223> OTHER INFORMATION: Consensus cleavage site for TEVp

<400> SEQUENCE: 13

```
Glu Asn Leu Tyr Phe Gln Gly
1               5
```

<210> SEQ ID NO 14

<211> LENGTH: 7
<212> TYPE: PRT
<213> ORGANISM: Artificial Sequence
<220> FEATURE:
<223> OTHER INFORMATION: Consensus cleavage site for TEVp

<400> SEQUENCE: 14

Glu Asn Leu Tyr Phe Gln Ser
1 5

<210> SEQ ID NO 15
<211> LENGTH: 8
<212> TYPE: PRT
<213> ORGANISM: Artificial Sequence
<220> FEATURE:
<223> OTHER INFORMATION: Consensus cleavage site for HRV 3C protease

<400> SEQUENCE: 15

Leu Glu Val Leu Phe Gln Gly Pro
1 5

<210> SEQ ID NO 16
<211> LENGTH: 4
<212> TYPE: PRT
<213> ORGANISM: Artificial Sequence
<220> FEATURE:
<223> OTHER INFORMATION: Consensus cleavage site for Factor Xa

<400> SEQUENCE: 16

Ile Glu Gly Arg
1

<210> SEQ ID NO 17
<211> LENGTH: 5
<212> TYPE: PRT
<213> ORGANISM: Artificial Sequence
<220> FEATURE:
<223> OTHER INFORMATION: Consensus cleavage site for Enterokinase

<400> SEQUENCE: 17

Asp Asp Asp Asp Lys
1 5

<210> SEQ ID NO 18
<211> LENGTH: 6
<212> TYPE: PRT
<213> ORGANISM: Artificial Sequence
<220> FEATURE:
<223> OTHER INFORMATION: Consensus cleavage site for Thrombin

<400> SEQUENCE: 18

Leu Val Pro Arg Gly Ser
1 5

<210> SEQ ID NO 19
<211> LENGTH: 17680
<212> TYPE: DNA
<213> ORGANISM: Artificial Sequence
<220> FEATURE:
<223> OTHER INFORMATION: SiR CRE-mCherryPEST

<400> SEQUENCE: 19
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180

-continued

```
ctttccattg acgtcaatgg gtggagtatt tacggtaaac tgcccacttg gcagtacatc    240
aagtgtatca tatgccaagt acgcccccta ttgacgtcaa tgacggtaaa tggcccgcct    300
ggcattatgc ccagtacatg accttatggg actttcctac ttggcagtac atctacgtat    360
tagtcatcgc tattaccatg gtgatgcggt tttggcagta catcaatggg cgtggatagc    420
ggtttgactc acggggattt ccaagtctcc accccattga cgtcaatggg agtttgtttt    480
ggcaccaaaa tcaacgggac tttccaaaat gtcgtaacaa ctccgcccca ttgacgcaaa    540
tgggcggtag gcgtgtacgg tgggaggtct atataagcag agctctctgg ctaactagag    600
aacccactgc ttactggctt atcgaaatta atacgactca ctatagggag acccaagctg    660
gctagattaa gcgtctgatg agtccgtgag gacgaaaccc ggagtcccgg gtcacgctta    720
acaaccagat caaagaaaaa acagacattg tcaattgcaa agcaaaaatg taacacccct    780
acaatggatg ccgacaagat tgtattcaaa gtcaataatc aggtggtctc tttgaagcct    840
gagattatcg tggatcaata tgagtacaag taccctgcca tcaaagattt gaaaaagccc    900
tgtataaccc taggaaaggc tcccgattta aataaagcat acaagtcagt tttgtcaggc    960
atgagcgccg ccaaacttaa tcctgacgat gtatgttcct atttggcagc ggcaatgcag   1020
ttttttgagg ggacatgtcc ggaagactgg accagctatg gaattgtgat tgcacgaaaa   1080
ggagataaga tcaccccagg ttctctggtg gagataaaac gtactgatgt agaagggaat   1140
tgggctctga caggaggcat ggaactgaca agagacccca ctgtccctga gcatgcgtcc   1200
ttagtcggtc ttctcttgag tctgtatagg ttgagcaaaa tatccgggca aaacactggt   1260
aactataaga caaacattgc agacaggata gagcagattt ttgagacagc cccttttgtt   1320
aaaatcgtgg aacaccatac tctaatgaca actcacaaaa tgtgtgctaa ttggagtact   1380
ataccaaact tcagattttt ggccggaacc tatgacatgt tttctcccgg gattgagcat   1440
ctatattcag caatcagagt gggcacagtt gtcactgctt atgaagactg ttcaggactg   1500
gtatcattta ctgggttcat aaaacaaatc aatctcaccg ctagagaggc aatactatat   1560
ttcttccaca agaactttga ggaagagata agaagaatgt ttgagccagg gcaggagaca   1620
gctgttcctc actcttattt catccacttc cgttcactag gcttgagtgg gaaatctcct   1680
tattcatcaa atgctgttgg tcacgtgttc aatctcattc actttgtagg atgctatatg   1740
ggtcaagtca gatccctaaa tgcaacggtt attgctgcat gtgctcctca tgaaatgtct   1800
gttctagggg gctatctggg agaggaattc ttcgggaaag ggacatttga aagaagattc   1860
ttcagagatg agaaagaact tcaagaatac gaggcggctg aactgacaaa gactgacgta   1920
gcactggcag atgatggaac tgtcaactct gacgacgagg actacttttc aggtgaaacc   1980
agaagtccgg aggctgttta tactcgaatc atgatgaatg gaggtcgact aaagagatct   2040
cacatacgga gatatgtctc agtcagttcc aatcatcaag cccgtccaaa ctcattcgcc   2100
gagtttctaa acaagacata ttcgagtgac tcaggttccg gagagaacct ctacttccaa   2160
tcgggatccg gtagccatgg cttcccgccg gaggtggagg agcaggatga tggcacgctg   2220
cccatgtctt gtgcccagga gagcgggatg gaccgtcacc ctgcagcctg tgcttctgct   2280
aggatcaatg tgtaagaagt tgaataacaa aatgccggaa atctacggat tgtgtatatc   2340
catcatgaaa aaaactaaca cccctccttt cgaaccatcc caaacatgag caagatcttt   2400
gtcaatccta gtgctattag agccggtctg gccgatcttg agatggctga agaaactgtt   2460
gatctgatca atagaaatat cgaagacaat caggctcatc tccaagggga acccatagag   2520
gtggacaatc tccctgagga tatggggcga cttcacctgg atgatggaaa atcgcccaac   2580
```

-continued

```
catggtgaga tagccaaggt gggagaaggc aagtatcgag aggactttca gatggatgaa   2640
ggagaggatc ctagcttcct gttccagtca tacctggaaa atgttggagt ccaaatagtc   2700
agacaaatga ggtcaggaga gagatttctc aagatatggt cacagaccgt agaagagatt   2760
atatcctatg tcgcggtcaa ctttcccaac cctccaggaa agtcttcaga ggataaatca   2820
acccagacta ctggccgaga gctcaagaag gagacaacac ccactccttc tcagagagaa   2880
agccaatcat cgaaagccag gatggcggct caaattgctt ctggccctcc agcccttgaa   2940
tggtcggcta ccaatgaaga ggatgatcta tcagtggagg ctgagatcgc tcaccagatt   3000
gcagaaagtt tctccaaaaa atataagttt ccctctcgat cctcagggat actcttgtat   3060
aattttgagc aattgaaaat gaaccttgat gatatagtta aagaggcaaa aaatgtacca   3120
ggtgtgaccc gtttagccca tgacgggtcc aaactccccc taagatgtgt actgggatgg   3180
gtcgctttgg ccaactctaa gaaattccag ttgttagtcg aatccgacaa gctgagtaaa   3240
atcatgcaag atgacttgaa tcgctataca tcttgctaac cgaacctctc ccctcagtcc   3300
ctctagacaa taaaatccga gatgtcccaa agtcaacatg aaaaaaacag gcaacaccac   3360
tgataaatcg atgaacctcc tacgtaagat agtgaaaaac cgcagggacg aggacactca   3420
aaaatcctct cccgcgtcag cccctctgga tgacgatgac ttgtggcttc cacccccctga   3480
atacgtcccg ctgaaagaac ttacaggcaa gaagaacatg aggaactttt gtatcaacgg   3540
aagggttaaa gtgtgtagcc cgaatggtta ctcgttcagg atcctgcggc acattctgaa   3600
atcattcgac gagatatatt ctgggaatca taggatgatc gggttagtca aagtggttat   3660
tggactggct ttgtcaggat ctccagtccc tgagggcctg aactgggtat acaaattgag   3720
gagaaccttt atcttccagt gggctgattc caggggccct cttgaagggg aggagttgga   3780
atactctcag gagatcactt gggatgatga tactgagttc gtcggattgc aaataagagt   3840
gattgcaaaa cagtgtcata tccagggcag agtctggtgt atcaacatga acccgagagc   3900
atgtcaacta tggtctgaca tgtctcttca gacacaaagg tccgaagagg acaaagattc   3960
ctctctgctt ctagaataac gtacgtcaga ttatatcccg caaatttatc acttgtttac   4020
ctctggagga gagaacatat gggctcaact ccaacccttg ggagcaatat aacaaaaaac   4080
atgttatggt gccattaaac cgctgcattt catcaaagtc aagttgatta cctttacatt   4140
ttgatcctct tggatgtgaa aaaaactatt aacatccctc aaaggacctg caggtacgcg   4200
gccgcggtac cgccaccatg gtgcccaaga agaagaggaa agtctccaac ctgctgactg   4260
tgcaccaaaa cctgcctgcc ctccctgtgg atgccacctc tgatgaagtc aggaagaacc   4320
tgatggacat gttcagggac aggcaggcct tctctgaaca cacctggaag atgctcctgt   4380
ctgtgtgcag atcctgggct gcctggtgca agctgaacaa caggaaatgg ttccctgctg   4440
aacctgagga tgtgagggac tacctcctgt acctgcaagc cagaggcctg gctgtgaaga   4500
ccatccaaca gcacctgggc cagctcaaca tgctgcacag gagatctggc ctgcctcgcc   4560
cttctgactc caatgctgtg tccctggtga tgaggagaat cagaaaggag aatgtggatg   4620
ctggggagag agccaagcag gccctggcct ttgaacgcac tgactttgac caagtcagat   4680
ccctgatgga gaactctgac agatgccagg acatcaggaa cctggccttc ctgggcattg   4740
cctacaacac cctgctgcgc attgccgaaa ttgccagaat cagagtgaag gacatctccc   4800
gcaccgatgg tgggagaatg ctgatccaca ttggcaggac caagaccctg gtgtccacag   4860
ctggtgtgga gaaggccctg tccctggggg ttaccaagct ggtggagaga tggatctctg   4920
```

-continued

```
tgtctggtgt ggctgatgac cccaacaact acctgttctg ccgggtcaga aagaatggtg   4980
tggctgcccc ttctgccacc tcccaactgt ccacccgggc cctggaaggg atctttgagg   5040
ccacccaccg cctgatctat ggtgccaagg atgactctgg gcagagatac ctggcctggt   5100
ctggccactc tgccagagtg ggtgctgcca gggacatggc cagggctggt gtgtccatcc   5160
ctgaaatcat gcaggctggt ggctggacca atgtgaacat tgtgatgaac tacatcagaa   5220
acctggactc tgagactggg gccatggtga ggctgctcga ggatggggac ggcagtggag   5280
gatccggagc cacgaacttc tctctgttaa agcaagcagg agacgtggaa gaaaaccccg   5340
gtcctaccgg tgtgagcaag ggcgaggagg ataacatggc catcatcaag gagttcatgc   5400
gcttcaaggt gcacatggag ggctccgtga acggccacga gttcgagatc gagggcgagg   5460
gcgagggccg cccctacgag ggcacccaga ccgccaagct gaaggtgacc aagggtggcc   5520
ccctgccctt cgcctgggac atcctgtccc ctcagttcat gtacggctcc aaggcctacg   5580
tgaagcaccc cgccgacatc cccgactact tgaagctgtc cttccccgag ggcttcaagt   5640
gggagcgcgt gatgaacttc gaggacggcg gcgtggtgac cgtgacccag gactcctccc   5700
tgcaggacgg cgagttcatc tacaaggtga agctgcgcgg caccaacttc ccctccgacg   5760
gccccgtaat gcagaagaag accatgggct gggaggcctc ctccgagcgg atgtaccccg   5820
aggacggcgc cctgaagggc gagatcaagc agaggctgaa gctgaaggac ggcggccact   5880
acgacgctga ggtcaagacc acctacaagg ccaagaagcc cgtgcagctg cccggcgcct   5940
acaacgtcaa catcaagttg gacatcacct cccacaacga ggactacacc atcgtggaac   6000
agtacgaacg cgccgagggc cgccactcca ccggcggcat ggacgagctg tacaagggat   6060
atctcagcca tggcttcccg ccggaggtgg aggagcagga tgatggcacg ctgcccatgt   6120
cttgtgccca ggagagcggg atggaccgtc accctgcagc ctgtgcttct gctaggatca   6180
atgtgtgact cgagggcgcg cctacccgcg gtagcttttc agtcgagaaa aaaacattag   6240
atcagaagaa caactggcaa cactttctca acctgagact tacttcaaga tgctcgatcc   6300
tggagaggtc tatgatgacc ctattgaccc aatcgagtta gaggctgaac ccagaggaac   6360
ccccattgtc cccaacatct tgaggaactc tgactacaat ctcaactctc ctttgataga   6420
agatcctgct agactaatgt tagaatggtt aaaaacaggg aatagacctt atcggatgac   6480
tctaacagac aattgctcca ggtctttcag agttttgaaa gattatttca agaaggtaga   6540
tttgggttct ctcaaggtgg gcggaatggc tgcacagtca atgatttctc tctggttata   6600
tggtgcccac tctgaatcca acaggagccg gagatgtata acagacttgg cccatttcta   6660
ttccaagtcg tcccccatag agaagctgtt gaatctcacg ctaggaaata gagggctgag   6720
aatcccccca gagggagtgt taagttgcct tgagagggtt gattatgata atgcatttgg   6780
aaggtatctt gccaacacgt attcctctta cttgttcttc catgtaatca ccttatacat   6840
gaacgcccta gactgggatg aagaaaagac catcctagca ttatggaaag atttaacctc   6900
agtggacatc gggaaggact tggtaaagtt caaagaccaa atatggggac tgctgatcgt   6960
gacaaaggac tttgtttact cccaaagttc caattgtctt tttgacagaa actacacact   7020
tatgctaaaa gatcttttct tgtctcgctt caactcctta atggtcttgc tctctccccc   7080
agagccccga tactcagatg acttgatatc tcaactatgc cagctgtaca ttgctgggga   7140
tcaagtcttg tctatgtgtg gaaactccgg ctatgaagtc atcaaaatat tggagccata   7200
tgtcgtgaat agtttagtcc agagagcaga aaagtttagg cctctcattc attccttggg   7260
agactttcct gtatttataa aagacaaggt aagtcaactt gaagagacgt tcggtccctg   7320
```

-continued tgcaagaagg ttctttaggg ctctggatca attcgacaac atacatgact tggtttttgt 7380
gtttggctgt tacaggcatt gggggcaccc atatatagat tatcgaaagg gtctgtcaaa 7440
actatatgat caggttcacc ttaaaaaaat gatagataag tcctaccagg agtgcttagc 7500
aagcgaccta gccaggagga tccttagatg ggttttgat aagtactcca agtggtatct 7560
ggattcaaga ttcctagccc gagaccaccc cttgactcct tatatcaaaa cccaaacatg 7620
gccacccaaa catattgtag acttggtggg ggatacatgg cacaagctcc cgatcacgca 7680
gatctttgag attcctgaat caatggatcc gtcagaaata ttggatgaca aatcacattc 7740
tttcaccaga acgagactag cttcttggct gtcagaaaac cgagggggggc ctgttcctag 7800 cgaaaaagtt attatcacgg ccctgtctaa gccgcctgtc aatccccgag agtttctgag 7860
gtctatagac ctcggaggat tgccagatga agacttgata attggcctca agccaaagga 7920
acgggaattg aagattgaag gtcgattctt tgctctaatg tcatggaatc taagattgta 7980
ttttgtcatc actgaaaaac tcttggccaa ctacatcttg ccactttttg acgcgctgac 8040
tatgacagac aacctgaaca aggtgtttaa aaagctgatc gacagggtca ccgggcaagg 8100
gcttttggac tattcaaggg tcacatatgc atttcacctg gactatgaaa agtggaacaa 8160
ccatcaaaga ttagagtcaa cagaggatgt attttctgtc ctagatcaag tgtttggatt 8220
gaagagagtg ttttctagaa cacacgagtt ttttcaaaag gcctggatct attattcaga 8280
cagatcagac ctcatcgggt tacgggagga tcaaatatac tgcttagatg cgtccaacgg 8340
cccaacctgt tggaatggcc aggatggcgg gctagaaggc ttacggcaga agggctggag 8400
tctagtcagc ttattgatga tagatagaga atctcaaatc aggaacacaa gaaccaaaat 8460
actagctcaa ggagacaacc aggttttatg tccgacatac atgttgtcgc cagggctatc 8520
tcaagagggg ctcctctatg aattggagag aatatcaagg aatgcacttt cgatatacag 8580
agccgtcgag gaaggggcat ctaagctagg gctgatcatc aagaaagaag agaccatgtg 8640
tagttatgac ttcctcatct atggaaaaac ccctttgttt agaggtaaca tattggtgcc 8700
tgagtccaaa agatgggcca gagtctcttg cgtctctaat gaccaaatag tcaacctcgc 8760
caatataatg tcgacagtgt ccaccaatgc gctaacagtg gcacaacact ctcaatcttt 8820
gatcaaaccg atgagggatt ttctgctcat gtcagtacag gcagtctttc actacctgct 8880
atttagccca atcttaaagg gaagagttta caagattctg agcgctgaag gggagagctt 8940
tctcctagcc atgtcaagga taatctatct agatccttct ttgggaggga tatctggaat 9000
gtccctcgga agattccata tacgacagtt ctcagaccct gtctctgaag ggttatcctt 9060
ctggagagag atctggttaa gctcccaaga gtcctggatt cacgcgttgt gtcaagaggc 9120
tggaaaccca gatcttggag agagaacact cgagagcttc actcgccttc tagaagatcc 9180
gaccacctta aatatcagag gaggggccag tcctaccatt ctactcaagg atgcaatcag 9240
aaaggcttta tatgacgagg tggacaaggt ggaaaattca gagtttcgag aggcaatcct 9300
gttgtccaag acccatagag ataattttat actcttctta atatctgttg agcctctgtt 9360
tcctcgattt ctcagtgagc tattcagttc gtctttttg ggaatccccg agtcaatcat 9420
tggattgata caaaactccc gaacgataag aaggcagttt agaaagagtc tctcaaaaac 9480
tttagaagaa tccttctaca actcagagat ccacgggatt agtcggatga cccagacacc 9540
tcagagggtt gggggggtgt ggccttgctc ttcagagagg gcagatctac ttagggagat 9600
ctcttgggga agaaaagtgg taggcacgac agttcctcac ccttctgaga tgttgggatt 9660

-continued

```
acttcccaag tcctctattt cttgcacttg tggagcaaca ggaggaggca atcctagagt   9720
ttctgtatca gtactcccgt cctttgatca gtcatttttt tcacgaggcc ccctaaaggg   9780
atacttgggc tcgtccacct ctatgtcgac ccagctattc catgcatggg aaaaagtcac   9840
taatgttcat gtggtgaaga gagctctatc gttaaaagaa tctataaact ggttcattac   9900
tagagattcc aacttggctc aagctctaat taggaacatt atgtctctga caggccctga   9960
tttccctcta gaggaggccc ctgtcttcaa aaggacgggg tcagccttgc ataggttcaa  10020
gtctgccaga tacagcgaag gagggtattc ttctgtctgc ccgaacctcc tctctcatat  10080
ttctgttagt acagacacca tgtctgattt gacccaagac gggaagaact acgatttcat  10140
gttccagcca ttgatgcttt atgcacagac atggacatca gagctggtac agagagacac  10200
aaggctaaga gactctacgt ttcattggca cctccgatgc aacaggtgtg tgagacccat  10260
tgacgacgtg accctggaga cctctcagat cttcgagttt ccggatgtgt cgaaaagaat  10320
atccagaatg gtttctgggg ctgtgcctca cttccagagg cttcccgata tccgtctgag  10380
accaggagat tttgaatctc taagcggtag agaaaagtct caccatatcg gatcagctca  10440
ggggctctta tactcaatct tagtggcaat tcacgactca ggatacaatg atggaaccat  10500
cttccctgtc aacatatacg gcaaggtttc ccctagagac tatttgagag ggctcgcaag  10560
gggagtattg ataggatcct cgatttgctt cttgacaaga atgacaaata tcaatattaa  10620
tagacctctt gaattggtct caggggtaat ctcatatatt ctcctgaggc tagataacca  10680
tccctccttg tacataatgc tcagagaacc gtctcttaga ggagagatat tttctatccc  10740
tcagaaaatc cccgccgctt atccaaccac tatgaaagaa ggcaacagat caatcttgtg  10800
ttatctccaa catgtgctac gctatgagcg agagataatc acggcgtctc cagagaatga  10860
ctggctatgg atcttttcag actttagaag tgccaaaatg acgtacctat ccctcattac  10920
ttaccagtct catcttctac tccagagggt tgagagaaac ctatctaaga gtatgagaga  10980
taacctgcga caattgagtt ctttgatgag gcaggtgctg ggcgggcacg gagaagatac  11040
cttagagtca gacgacaaca ttcaacgact gctaaaagac tctttacgaa ggacaagatg  11100
ggtggatcaa gaggtgcgcc atgcagctag aaccatgact ggagattaca gccccaacaa  11160
gaaggtgtcc cgtaaggtag gatgttcaga atgggtctgc tctgctcaac aggttgcagt  11220
ctctacctca gcaaacccgg cccctgtctc ggagcttgac ataagggccc tctctaagag  11280
gttccagaac cctttgatct cgggcttgag agtggttcag tgggcaaccg gtgctcatta  11340
taagcttaag cctattctag atgatctcaa tgttttccca tctctctgcc ttgtagttgg  11400
ggacgggtca ggggggatat caagggcagt cctcaacatg tttccagatg ccaagcttgt  11460
gttcaacagt cttttagagg tgaatgacct gatggcttcc ggaacacatc cactgcctcc  11520
ttcagcaatc atgaggggag gaaatgatat cgtctccaga gtgatagatc ttgactcaat  11580
ctgggaaaaa ccgtccgact tgagaaactt ggcaacctgg aaatacttcc agtcagtcca  11640
aaagcaggtc aacatgtcct atgacctcat tatttgcgat gcagaagtta ctgacattgc  11700
atctatcaac cggatcaccc tgttaatgtc cgattttgca ttgtctatag atggaccact  11760
ctatttggtc ttcaaaactt atgggactat gctagtaaat ccaaactaca aggctattca  11820
acacctgtca agagcgttcc cctcggtcac agggtttatc acccaagtaa cttcgtcttt  11880
ttcatctgag ctctacctcc gattctccaa acgagggaag tttttcagag atgctgagta  11940
cttgacctct tccacccttc gagaaatgag ccttgtgtta ttcaattgta gcagccccaa  12000
gagtgagatg cagagagctc gttccttgaa ctatcaggat cttgtgagag gatttcctga  12060
```

agaaatcata tcaaatcctt acaatgagat gatcataact ctgattgaca gtgatgtaga 12120
atcttttcta gtccacaaga tggttgatga tcttgagtta cagaggggaa ctctgtctaa 12180
agtggctatc attatagcca tcatgatagt tttctccaac agagtcttca acgtttccaa 12240
acccctaact gacccctcgt tctatccacc gtctgatccc aaaatcctga ggcacttcaa 12300
catatgttgc agtactatga tgtatctatc tactgcttta ggtgacgtcc ctagcttcgc 12360
aagacttcac gacctgtata acagacctat aacttattac ttcagaaagc aagtcattcg 12420
agggaacgtt tatctatctt ggagttggtc caacgacacc tcagtgttca aaagggtagc 12480
ctgtaattct agcctgagtc tgtcatctca ctggatcagg ttgatttaca agatagtgaa 12540
gactaccaga ctcgttggca gcatcaagga tctatccaga gaagtggaaa gacaccttca 12600
taggtacaac aggtggatca ccctagagga tatcagatct agatcatccc tactagacta 12660
cagttgcctg tgaaccggat actcctggaa gcctgcccat gctaagactc ttgtgtgatg 12720
tatcttgaaa aaaacaagat caccggatac tcctggaagc ctgcccatgc taagactctt 12780
gtgtgatgta tcttgaaaaa aacaagatcc taaatctgaa cctttggttg tttgattgtt 12840
tttctcattt ttgttgttta tttgttaagc gtgggtcggc atggcatctc cacctcctcg 12900
cggtccgacc tgggcatccg aaggaggacg cacgtccact cggatggcta agggagaagg 12960
gcgaattcca gcacactggc ggccgttact agtggatccg agctcggtac caagcttaag 13020
tttaaaccgc tgatcagcct cgactgtgcc ttctagttgc cagccatctg ttgtttgccc 13080
ctcccccgtg ccttccttga ccctggaagg tgccactccc actgtccttt cctaataaaa 13140
tgaggaaatt gcatcgcatt gtctgagtag gtgtcattct attctggggg gtggggtggg 13200
gcaggacagc aagggggagg attgggaaga caatagcagg catgctgggg atgcggtggg 13260
ctctatggct tctgaggcgg aaagaaccag ctggggctct agggggtatc cccacgcgcc 13320
ctgtagcggc gcattaagcg cggcgggtgt ggtggttacg cgcagcgtga ccgctacact 13380
tgccagcgcc ctagcgcccg ctcctttcgc tttcttccct tcctttctcg ccacgttcgc 13440
cggctttccc cgtcaagctc taaatcgggg gctcccttta gggttccgat ttagtgcttt 13500
acggcacctc gaccccaaaa aacttgatta gggtgatggt tcacgtagtg ggccatcgcc 13560
ctgatagacg gtttttcgcc ctttgacgtt ggagtccacg ttctttaata gtggactctt 13620
gttccaaact ggaacaacac tcaaccctat ctcggtctat tcttttgatt tataagggat 13680
tttgccgatt tcggcctatt ggttaaaaaa tgagctgatt taacaaaaat ttaacgcgaa 13740
ttaattctgt ggaatgtgtg tcagttaggg tgtggaaagt ccccaggctc cccagcaggc 13800
agaagtatgc aaagcatgca tctcaattag tcagcaacca ggtgtggaaa gtccccaggc 13860
tccccagcag gcagaagtat gcaaagcatg catctcaatt agtcagcaac catagtcccg 13920
cccctaactc cgcccatccc gcccctaact ccgcccagtt ccgcccattc tccgccccat 13980
ggctgactaa ttttttttat ttatgcagag gccgaggccg cctctgcctc tgagctattc 14040
cagaagtagt gaggaggctt ttttggaggc ctaggctttt gcaaaaagct cccgggagct 14100
tgtatatcca ttttcggatc tgatcaagag acaggatgag gatcgtttcg catgattgaa 14160
caagatggat tgcacgcagg ttctccggcc gcttgggtgg agaggctatt cggctatgac 14220
tgggcacaac agacaatcgg ctgctctgat gccgccgtgt tccggctgtc agcgcagggg 14280
cgcccggttc tttttgtcaa gaccgacctg tccggtgccc tgaatgaact gcaggacgag 14340
gcagcgcggc tatcgtggct ggccacgacg ggcgttcctt gcgcagctgt gctcgacgtt 14400

-continued

```
gtcactgaag cgggaaggga ctggctgcta ttgggcgaag tgccggggca ggatctcctg  14460
tcatctcacc ttgctcctgc cgagaaagta tccatcatgg ctgatgcaat gcggcggctg  14520
catacgcttg atccggctac ctgcccattc gaccaccaag cgaaacatcg catcgagcga  14580
gcacgtactc ggatggaagc cggtcttgtc gatcaggatg atctggacga agagcatcag  14640
gggctcgcgc cagccgaact gttcgccagg ctcaaggcgc gcatgcccga cggcgaggat  14700
ctcgtcgtga cccatggcga tgcctgcttg ccgaatatca tggtggaaaa tggccgcttt  14760
tctggattca tcgactgtgg ccggctgggt gtggcggacc gctatcagga catagcgttg  14820
gctacccgtg atattgctga agagcttggc ggcgaatggg ctgaccgctt cctcgtgctt  14880
tacggtatcg ccgctcccga ttcgcagcgc atcgccttct atcgccttct tgacgagttc  14940
ttctgagcgg gactctgggg ttcgaaatga ccgaccaagc gacgcccaac ctgccatcac  15000
gagatttcga ttccaccgcc gccttctatg aaaggttggg cttcggaatc gttttccggg  15060
acgccggctg gatgatcctc cagcgcgggg atctcatgct ggagttcttc gcccacccca  15120
acttgtttat tgcagcttat aatggttaca aataaagcaa tagcatcaca aatttcacaa  15180
ataaagcatt tttttcactg cattctagtt gtggtttgtc caaactcatc aatgtatctt  15240
atcatgtctg tataccgtcg acctctagct agagcttggc gtaatcatgg tcatagctgt  15300
ttcctgtgtg aaattgttat ccgctcacaa ttccacacaa catacgagcc ggaagcataa  15360
agtgtaaagc ctggggtgcc taatgagtga gctaactcac attaattgcg ttgcgctcac  15420
tgcccgcttt ccagtcggga aacctgtcgt gccagctgca ttaatgaatc ggccaacgcg  15480
cggggagagg cggtttgcgt attgggcgct cttccgcttc ctcgctcact gactcgctgc  15540
gctcggtcgt tcggctgcgg cgagcggtat cagctcactc aaaggcggta atacggttat  15600
ccacagaatc aggggataac gcaggaaaga acatgtgagc aaaaggccag caaaaggcca  15660
ggaaccgtaa aaaggccgcg ttgctggcgt ttttccatag gctccgcccc cctgacgagc  15720
atcacaaaaa tcgacgctca agtcagaggt ggcgaaaccc gacaggacta taaagatacc  15780
aggcgtttcc ccctggaagc tccctcgtgc gctctcctgt tccgaccctg ccgcttaccg  15840
gatacctgtc cgcctttctc ccttcgggaa gcgtggcgct ttctcatagc tcacgctgta  15900
ggtatctcag ttcggtgtag gtcgttcgct ccaagctggg ctgtgtgcac gaaccccccg  15960
ttcagcccga ccgctgcgcc ttatccggta actatcgtct tgagtccaac ccggtaagac  16020
acgacttatc gccactggca gcagccactg gtaacaggat tagcagagcg aggtatgtag  16080
gcggtgctac agagttcttg aagtggtggc ctaactacgg ctacactaga agaacagtat  16140
ttggtatctg cgctctgctg aagccagtta ccttcggaaa aagagttggt agctcttgat  16200
ccggcaaaca aaccaccgct ggtagcggtg gtttttttgt ttgcaagcag cagattacgc  16260
gcagaaaaaa aggatctcaa gaagatcctt tgatcttttc tacggggtct gacgctcagt  16320
ggaacgaaaa ctcacgttaa gggattttgg tcatgagatt atcaaaaagg atcttcacct  16380
agatcctttt aaattaaaaa tgaagtttta aatcaatcta aagtatatat gagtaaactt  16440
ggtctgacag ttaccaatgc ttaatcagtg aggcacctat ctcagcgatc tgtctatttc  16500
gttcatccat agttgcctga ctccccgtcg tgtagataac tacgatacgg gagggcttac  16560
catctggccc cagtgctgca atgataccgc gagacccacg ctcaccggct ccagatttat  16620
cagcaataaa ccagccagcc ggaagggccg agcgcagaag tggtcctgca actttatccg  16680
cctccatcca gtctattaat tgttgccggg aagctagagt aagtagttcg ccagttaata  16740
gtttgcgcaa cgttgttgcc attgctacag gcatcgtggt gtcacgctcg tcgtttggta  16800
```

tggcttcatt cagctccggt tcccaacgat caaggcgagt tacatgatcc cccatgttgt 16860
gcaaaaaagc ggttagctcc ttcggtcctc cgatcgttgt cagaagtaag ttggccgcag 16920
tgttatcact catggttatg gcagcactgc ataattctct tactgtcatg ccatccgtaa 16980
gatgcttttc tgtgactggt gagtactcaa ccaagtcatt ctgagaatag tgtatgcggc 17040
gaccgagttg ctcttgcccg gcgtcaatac gggataatac cgcgccacat agcagaactt 17100
taaaagtgct catcattgga aaacgttctt cggggcgaaa actctcaagg atcttaccgc 17160
tgttgagatc cagttcgatg taacccactc gtgcacccaa ctgatcttca gcatctttta 17220
ctttcaccag cgtttctggg tgagcaaaaa caggaaggca aaatgccgca aaaaagggaa 17280
taagggcgac acggaaatgt tgaatactca tactcttcct ttttcaatat tattgaagca 17340
tttatcaggg ttattgtctc atgagcggat acatatttga atgtatttag aaaaataaac 17400
aaataggggt tccgcgcaca tttccccgaa aagtgccacc tgacgtcgac ggatcgggag 17460
atctcccgat cccctatggt gcactctcag tacaatctgc tctgatgccg catagttaag 17520
ccagtatctg ctccctgctt gtgtgttgga ggtcgctgag tagtgcgcga gcaaaattta 17580
agctacaaca aggcaaggct tgaccgacaa ttgcatgaag aatctgctta gggttaggcg 17640
ttttgcgctg cttcgcgatg tacgggccag atatacgcgt 17680

<210> SEQ ID NO 20
<211> LENGTH: 15678
<212> TYPE: DNA
<213> ORGANISM: Artificial Sequence
<220> FEATURE:
<223> OTHER INFORMATION: plasmid encoding SiR vector

<400> SEQUENCE: 20
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctaga 900
ttaagcgtct gatgagtccg tgaggacgaa acccggagtc ccgggtcacg cttaacaacc 960
agatcaaaga aaaaacagac attgtcaatt gcaaagcaaa aatgtaacac ccctacaatg 1020
gatgccgaca agattgtatt caaagtcaat aatcaggtgg tctctttgaa gcctgagatt 1080
atcgtggatc aatatgagta caagtaccct gccatcaaag atttgaaaaa gccctgtata 1140

-continued

```
accctaggaa aggctcccga tttaaataaa gcatacaagt cagttttgtc aggcatgagc   1200
gccgccaaac ttaatcctga cgatgtatgt tcctatttgg cagcggcaat gcagtttttt   1260
gaggggacat gtccggaaga ctggaccagc tatggaattg tgattgcacg aaaaggagat   1320
aagatcaccc caggttctct ggtggagata aaacgtactg atgtagaagg gaattgggct   1380
ctgacaggag gcatggaact gacaagagac cccactgtcc ctgagcatgc gtccttagtc   1440
ggtcttctct tgagtctgta taggttgagc aaaatatccg ggcaaaacac tggtaactat   1500
aagacaaaca ttgcagacag gatagagcag atttttgaga cagccccttt tgttaaaatc   1560
gtggaacacc atactctaat gacaactcac aaaatgtgtg ctaattggag tactatacca   1620
aacttcagat tttggccgg aacctatgac atgtttttct cccggattga gcatctatat   1680
tcagcaatca gagtgggcac agttgtcact gcttatgaag actgttcagg actggtatca   1740
tttactgggt tcataaaaca aatcaatctc accgctagag aggcaatact atatttcttc   1800
cacaagaact ttgaggaaga gataagaaga atgtttgagc cagggcagga gacagctgtt   1860
cctcactctt atttcatcca cttccgttca ctaggcttga gtgggaaatc tccttattca   1920
tcaaatgctg ttggtcacgt gttcaatctc attcactttg taggatgcta tatgggtcaa   1980
gtcagatccc taaatgcaac ggttattgct gcatgtgctc ctcatgaaat gtctgttcta   2040
gggggctatc tgggagagga attcttcggg aaagggacat ttgaaagaag attcttcaga   2100
gatgagaaag aacttcaaga atacgaggcg gctgaactga caaagactga cgtagcactg   2160
gcagatgatg gaactgtcaa ctctgacgac gaggactact tttcaggtga aaccagaagt   2220
ccggaggctg tttatactcg aatcatgatg aatggaggtc gactaaagag atctcacata   2280
cggagatatg tctcagtcag ttccaatcat caagcccgtc caaactcatt cgccgagttt   2340
ctaaacaaga catattcgag tgactcaggt tccggagaga acctctactt ccaatcggga   2400
tccggtagcc atggcttccc gccggaggtg gaggagcagg atgatggcac gctgcccatg   2460
tcttgtgccc aggagagcgg gatggaccgt caccctgcag cctgtgcttc tgctaggatc   2520
aatgtgtaag aagttgaata acaaaatgcc ggaaatctac ggattgtgta tatccatcat   2580
gaaaaaaact aacacccctc ctttcgaacc atcccaaaca tgagcaagat ctttgtcaat   2640
cctagtgcta ttagagccgg tctggccgat cttgagatgg ctgaagaaac tgttgatctg   2700
atcaatagaa atatcgaaga caatcaggct catctccaag ggaacccat agaggtggac   2760
aatctccctg aggatatggg gcgacttcac ctggatgatg gaaaatcgcc caaccatggt   2820
gagatagcca aggtgggaga aggcaagtat cgagaggact ttcagatgga tgaaggagag   2880
gatcctagct tcctgttcca gtcatacctg gaaaatgttg gagtccaaat agtcagacaa   2940
atgaggtcag gagagagatt tctcaagata tggtcacaga ccgtagaaga gattatatcc   3000
tatgtcgcgg tcaactttcc caaccctcca ggaaagtctt cagaggataa atcaacccag   3060
actactggcc gagagctcaa gaaggagaca acacccactc cttctcagag agaaagccaa   3120
tcatcgaaag ccaggatggc ggctcaaatt gcttctggcc ctccagccct tgaatggtcg   3180
gctaccaatg aagaggatga tctatcagtg gaggctgaga tcgctcacca gattgcagaa   3240
agtttctcca aaaaatataa gtttccctct cgatcctcag ggatactctt gtataatttt   3300
gagcaattga aatgaacct tgatgatata gttaaagagg caaaaaatgt accaggtgtg   3360
acccgtttag cccatgacgg gtccaaactc cccctaagat gtgtactggg atgggtcgct   3420
ttggccaact ctaagaaatt ccagttgtta gtcgaatccg acaagctgag taaaatcatg   3480
caagatgact tgaatcgcta tacatcttgc taaccgaacc tctcccctca gtccctctag   3540
```

```
acaataaaat ccgagatgtc ccaaagtcaa catgaaaaaa acaggcaaca ccactgataa   3600
atcgatgaac ctcctacgta agatagtgaa aaaccgcagg gacgaggaca ctcaaaaatc   3660
ctctcccgcg tcagcccctc tggatgacga tgacttgtgg cttccacccc ctgaatacgt   3720
cccgctgaaa gaacttacag gcaagaagaa catgaggaac ttttgtatca acggaagggt   3780
taaagtgtgt agcccgaatg gttactcgtt caggatcctg cggcacattc tgaaatcatt   3840
cgacgagata tattctggga atcataggat gatcgggtta gtcaaagtgg ttattggact   3900
ggctttgtca ggatctccag tccctgaggg cctgaactgg gtatacaaat tgaggagaac   3960
ctttatcttc cagtgggctg attccagggg ccctcttgaa ggggaggagt tggaatactc   4020
tcaggagatc acttgggatg atgatactga gttcgtcgga ttgcaaataa gagtgattgc   4080
aaaacagtgt catatccagg gcagagtctg gtgtatcaac atgaacccga gagcatgtca   4140
actatggtct gacatgtctc ttcagacaca aaggtccgaa gaggacaaag attcctctct   4200
gcttctagaa taacgtacgt cagattatat cccgcaaatt tatcacttgt ttacctctgg   4260
aggagagaac atatgggctc aactccaacc cttgggagca atataacaaa aaacatgtta   4320
tggtgccatt aaaccgctgc atttcatcaa agtcaagttg attaccttta cattttgatc   4380
ctcttggatg tgaaaaaaac tattaacatc cctcaaagga cctgcaggta cgcggccgct   4440
acgcccgggc tacgctagca tgaaaaaaac taacacccct ccttaattaa tacggcgcgc   4500
ctacccgcgg tagcttttca gtcgagaaaa aaacattaga tcagaagaac aactggcaac   4560
actttctcaa cctgagactt acttcaagat gctcgatcct ggagaggtct atgatgaccc   4620
tattgaccca atcgagttag aggctgaacc cagaggaacc cccattgtcc ccaacatctt   4680
gaggaactct gactacaatc tcaactctcc tttgatagaa gatcctgcta gactaatgtt   4740
agaatggtta aaaacaggga atagacctta tcggatgact ctaacagaca attgctccag   4800
gtctttcaga gttttgaaag attatttcaa gaaggtagat ttgggttctc tcaaggtggg   4860
cggaatggct gcacagtcaa tgatttctct ctggttatat ggtgcccact ctgaatccaa   4920
caggagccgg agatgtataa cagacttggc ccatttctat tccaagtcgt cccccataga   4980
gaagctgttg aatctcacgc taggaaatag agggctgaga atcccccag agggagtgtt   5040
aagttgcctt gagagggttg attatgataa tgcatttgga aggtatcttg ccaacacgta   5100
ttcctcttac ttgttcttcc atgtaatcac cttatacatg aacgccctag actgggatga   5160
agaaaagacc atcctagcat tatggaaaga tttaacctca gtggacatcg ggaaggactt   5220
ggtaaagttc aaagaccaaa tatggggact gctgatcgtg acaaaggact ttgtttactc   5280
ccaaagttcc aattgtcttt ttgacagaaa ctacacactt atgctaaaag atcttttctt   5340
gtctcgcttc aactccttaa tggtcttgct ctctcccca gagccccgat actcagatga   5400
cttgatatct caactatgcc agctgtacat tgctggggat caagtcttgt ctatgtgtgg   5460
aaactccggc tatgaagtca tcaaaatatt ggagccatat gtcgtgaata gtttagtcca   5520
gagagcagaa aagtttaggc ctctcattca ttccttggga gactttcctg tatttataaa   5580
agacaaggta agtcaacttg aagagacgtt cggtccctgt gcaagaaggt tctttagggc   5640
tctggatcaa ttcgacaaca tacatgactt ggtttttgtg tttggctgtt acaggcattg   5700
ggggcaccca tatatagatt atcgaaaggg tctgtcaaaa ctatatgatc aggttcacct   5760
taaaaaaatg atagataagt cctaccagga gtgcttagca agcgacctag ccaggaggat   5820
ccttagatgg ggttttgata agtactccaa gtggtatctg gattcaagat tcctagcccg   5880
```

-continued agaccacccc ttgactcctt atatcaaaac ccaaacatgg ccacccaaac atattgtaga 5940
cttggtgggg gatacatggc acaagctccc gatcacgcag atctttgaga ttcctgaatc 6000
aatggatccg tcagaaatat tggatgacaa atcacattct ttcaccagaa cgagactagc 6060
ttcttggctg tcagaaaacc gagggggggcc tgttcctagc gaaaaagtta ttatcacggc 6120
cctgtctaag ccgcctgtca atccccgaga gtttctgagg tctatagacc tcggaggatt 6180
gccagatgaa gacttgataa ttggcctcaa gccaaaggaa cgggaattga agattgaagg 6240
tcgattcttt gctctaatgt catggaatct aagattgtat tttgtcatca ctgaaaaact 6300
cttggccaac tacatcttgc cactttttga cgcgctgact atgacagaca acctgaacaa 6360
ggtgtttaaa aagctgatcg acagggtcac cgggcaaggg cttttggact attcaagggt 6420
cacatatgca tttcacctgg actatgaaaa gtggaacaac catcaaagat tagagtcaac 6480
agaggatgta ttttctgtcc tagatcaagt gtttggattg aagagagtgt tttctagaac 6540
acacgagttt tttcaaaagg cctggatcta ttattcagac agatcagacc tcatcgggtt 6600
acgggaggat caaatatact gcttagatgc gtccaacggc ccaacctgtt ggaatggcca 6660
ggatggcggg ctagaaggct tacggcagaa gggctggagt ctagtcagct tattgatgat 6720
agatagagaa tctcaaatca ggaacacaag aaccaaaata ctagctcaag gagacaacca 6780
ggttttatgt ccgacataca tgttgtcgcc agggctatct caagaggggc tcctctatga 6840
attggagaga atatcaagga atgcactttc gatatacaga gccgtcgagg aaggggcatc 6900
taagctaggg ctgatcatca agaaagaaga gaccatgtgt agttatgact tcctcatcta 6960
tggaaaaacc cctttgttta gaggtaacat attggtgcct gagtccaaaa gatgggccag 7020
agtctcttgc gtctctaatg accaaatagt caacctcgcc aatataatgt cgacagtgtc 7080
caccaatgcg ctaacagtgg cacaacactc tcaatctttg atcaaaccga tgagggattt 7140
tctgctcatg tcagtacagg cagtctttca ctacctgcta tttagcccaa tcttaaaggg 7200
aagagtttac aagattctga gcgctgaagg ggagagcttt ctcctagcca tgtcaaggat 7260
aatctatcta gatccttctt tgggagggat atctggaatg tccctcggaa gattccatat 7320
acgacagttc tcagaccctg tctctgaagg gttatccttc tggagagaga tctggttaag 7380
ctcccaagag tcctggattc acgcgttgtg tcaagaggct ggaaacccag atcttggaga 7440
gagaacactc gagagcttca ctcgccttct agaagatccg accaccttaa atatcagagg 7500
aggggccagt cctaccattc tactcaagga tgcaatcaga aaggctttat atgacgaggt 7560
ggacaaggtg gaaaattcag agtttcgaga ggcaatcctg ttgtccaaga cccatagaga 7620
taattttata ctcttcttaa tatctgttga gcctctgttt cctcgatttc tcagtgagct 7680
attcagttcg tcttttttgg gaatccccga gtcaatcatt ggattgatac aaaactcccg 7740
aacgataaga aggcagttta gaaagagtct ctcaaaaact ttagaagaat ccttctacaa 7800
ctcagagatc cacgggatta gtcggatgac ccagacacct cagagggttg ggggggtgtg 7860
gccttgctct tcagagaggg cagatctact tagggagatc tcttggggaa gaaaagtggt 7920
aggcacgaca gttcctcacc cttctgagat gttgggatta cttcccaagt cctctatttc 7980
ttgcacttgt ggagcaacag gaggaggcaa tcctagagtt tctgtatcag tactcccgtc 8040
ctttgatcag tcattttttt cacgaggccc cctaaaggga tacttgggct cgtccacctc 8100
tatgtcgacc cagctattcc atgcatggga aaaagtcact aatgttcatg tggtgaagag 8160
agctctatcg ttaaaagaat ctataaactg gttcattact agagattcca acttggctca 8220
agctctaatt aggaacatta tgtctctgac aggccctgat ttccctctag aggaggcccc 8280

```
tgtcttcaaa aggacggggt cagccttgca taggttcaag tctgccagat acagcgaagg   8340
agggtattct tctgtctgcc cgaacctcct ctctcatatt tctgttagta cagacaccat   8400
gtctgatttg acccaagacg ggaagaacta cgatttcatg ttccagccat tgatgcttta   8460
tgcacagaca tggacatcag agctggtaca gagagacaca aggctaagag actctacgtt   8520
tcattggcac ctccgatgca acaggtgtgt gagacccatt gacgacgtga ccctggagac   8580
ctctcagatc ttcgagtttc cggatgtgtc gaaaagaata tccagaatgg tttctggggc   8640
tgtgcctcac ttccagaggc ttcccgatat ccgtctgaga ccaggagatt ttgaatctct   8700
aagcggtaga gaaaagtctc accatatcgg atcagctcag ggctcttat actcaatctt   8760
agtggcaatt cacgactcag gatacaatga tggaaccatc ttccctgtca acatatacgg   8820
caaggtttcc cctagagact atttgagagg gctcgcaagg ggagtattga taggatcctc   8880
gatttgcttc ttgacaagaa tgacaaatat caatattaat agacctcttg aattggtctc   8940
aggggtaatc tcatatattc tcctgaggct agataaccat ccctccttgt acataatgct   9000
cagagaaccg tctcttagag gagagatatt ttctatccct cagaaaatcc ccgccgctta   9060
tccaaccact atgaaagaag gcaacagatc aatcttgtgt tatctccaac atgtgctacg   9120
ctatgagcga gagataatca cggcgtctcc agagaatgac tggctatgga tcttttcaga   9180
ctttagaagt gccaaaatga cgtacctatc cctcattact taccagtctc atcttctact   9240
ccagagggtt gagagaaacc tatctaagag tatgagagat aacctgcgac aattgagttc   9300
tttgatgagg caggtgctgg gcgggcacgg agaagatacc ttagagtcag acgacaacat   9360
tcaacgactg ctaaaagact ctttacgaag gacaagatgg gtggatcaag aggtgcgcca   9420
tgcagctaga accatgactg gagattacag ccccaacaag aaggtgtccc gtaaggtagg   9480
atgttcagaa tgggtctgct ctgctcaaca ggttgcagtc tctacctcag caaacccggc   9540
ccctgtctcg gagcttgaca taagggccct ctctaagagg ttccagaacc ctttgatctc   9600
gggcttgaga gtggttcagt gggcaaccgg tgctcattat aagcttaagc ctattctaga   9660
tgatctcaat gttttcccat ctctctgcct tgtagttggg gacgggtcag gggggatatc   9720
aagggcagtc ctcaacatgt ttccagatgc caagcttgtg ttcaacagtc ttttagaggt   9780
gaatgacctg atggcttccg gaacacatcc actgcctcct tcagcaatca tgaggggagg   9840
aaatgatatc gtctccagag tgatagatct tgactcaatc tgggaaaaac cgtccgactt   9900
gagaaacttg gcaacctgga aatacttcca gtcagtccaa aagcaggtca acatgtccta   9960
tgacctcatt atttgcgatg cagaagttac tgacattgca tctatcaacc ggatcaccct  10020
gttaatgtcc gattttgcat tgtctataga tggaccactc tatttggtct tcaaaactta  10080
tgggactatg ctagtaaatc caaactacaa ggctattcaa cacctgtcaa gagcgttccc  10140
ctcggtcaca gggtttatca cccaagtaac ttcgtctttt tcatctgagc tctacctccg  10200
attctccaaa cgagggaagt ttttcagaga tgctgagtac ttgacctctt ccacccttcg  10260
agaaatgagc cttgtgttat tcaattgtag cagccccaag agtgagatgc agagagctcg  10320
ttccttgaac tatcaggatc ttgtgagagg atttcctgaa gaaatcatat caaatcctta  10380
caatgagatg atcataactc tgattgacag tgatgtagaa tcttttctag tccacaagat  10440
ggttgatgat cttgagttac agaggggaac tctgtctaaa gtggctatca ttatagccat  10500
catgatagtt ttctccaaca gagtcttcaa cgtttccaaa cccctaactg acccctcgtt  10560
ctatccaccg tctgatccca aaatcctgag gcacttcaac atatgttgca gtactatgat  10620
```

-continued gtatctatct actgctttag gtgacgtccc tagcttcgca agacttcacg acctgtataa 10680
cagacctata acttattact tcagaaagca agtcattcga gggaacgttt atctatcttg 10740
gagttggtcc aacgacacct cagtgttcaa aagggtagcc tgtaattcta gcctgagtct 10800
gtcatctcac tggatcaggt tgatttacaa gatagtgaag actaccagac tcgttggcag 10860
catcaaggat ctatccagag aagtggaaag acaccttcat aggtacaaca ggtggatcac 10920
cctagaggat atcagatcta gatcatccct actagactac agttgcctgt gaaccggata 10980
ctcctggaag cctgcccatg ctaagactct tgtgtgatgt atcttgaaaa aaacaagatc 11040
ctaaatctga acctttggtt gtttgattgt ttttctcatt tttgttgttt atttgttaag 11100
cgtgggtcgg catggcatct ccacctcctc gcggtccgac ctgggcatcc gaaggaggac 11160
gcacgtccac tcggatggct aagggagaag ggcgaattcc agcacactgg cggccgttac 11220
tagtggatcc gagctcggta ccaagcttaa gtttaaaccg ctgatcagcc tcgactgtgc 11280
cttctagttg ccagccatct gttgtttgcc cctcccccgt gccttccttg accctggaag 11340
gtgccactcc cactgtcctt tcctaataaa atgaggaaat tgcatcgcat tgtctgagta 11400
ggtgtcattc tattctgggg ggtggggtgg ggcaggacag caagggggag gattgggaag 11460
acaatagcag gcatgctggg gatgcggtgg gctctatggc ttctgaggcg gaaagaacca 11520
gctggggctc tagggggtat ccccacgcgc cctgtagcgg cgcattaagc gcggcgggtg 11580
tggtggttac gcgcagcgtg accgctacac ttgccagcgc cctagcgccc gctcctttcg 11640
ctttcttccc ttcctttctc gccacgttcg ccggctttcc ccgtcaagct ctaaatcggg 11700
ggctcccttt agggttccga tttagtgctt tacggcacct cgaccccaaa aaacttgatt 11760
agggtgatgg ttcacgtagt gggccatcgc cctgatagac ggtttttcgc cctttgacgt 11820
tggagtccac gttctttaat agtggactct tgttccaaac tggaacaaca ctcaacccta 11880
tctcggtcta ttcttttgat ttataaggga ttttgccgat ttcggcctat tggttaaaaa 11940
atgagctgat ttaacaaaaa tttaacgcga attaattctg tggaatgtgt gtcagttagg 12000
gtgtggaaag tccccaggct ccccagcagg cagaagtatg caaagcatgc atctcaatta 12060
gtcagcaacc aggtgtggaa agtccccagg ctccccagca ggcagaagta tgcaaagcat 12120
gcatctcaat tagtcagcaa ccatagtccc gcccctaact ccgcccatcc cgcccctaac 12180
tccgcccagt tccgcccatt ctccgcccca tggctgacta atttttttta tttatgcaga 12240
ggccgaggcc gcctctgcct ctgagctatt ccagaagtag tgaggaggct tttttggagg 12300
cctaggcttt tgcaaaaagc tcccgggagc ttgtatatcc attttcggat ctgatcaaga 12360
gacaggatga ggatcgtttc gcatgattga acaagatgga ttgcacgcag gttctccggc 12420
cgcttgggtg gagaggctat tcggctatga ctgggcacaa cagacaatcg gctgctctga 12480
tgccgccgtg ttccggctgt cagcgcaggg gcgcccggtt ctttttgtca agaccgacct 12540
gtccggtgcc ctgaatgaac tgcaggacga ggcagcgcgg ctatcgtggc tggccacgac 12600
gggcgttcct tgcgcagctg tgctcgacgt tgtcactgaa gcgggaaggg actggctgct 12660
attgggcgaa gtgccggggc aggatctcct gtcatctcac cttgctcctg ccgagaaagt 12720
atccatcatg gctgatgcaa tgcggcggct gcatacgctt gatccggcta cctgcccatt 12780
cgaccaccaa gcgaaacatc gcatcgagcg agcacgtact cggatggaag ccggtcttgt 12840
cgatcaggat gatctggacg aagagcatca ggggctcgcg ccagccgaac tgttcgccag 12900
gctcaaggcg cgcatgcccg acggcgagga tctcgtcgtg acccatggcg atgcctgctt 12960
gccgaatatc atggtggaaa atggccgctt ttctggattc atcgactgtg gccggctggg 13020

-continued

```
tgtggcggac cgctatcagg acatagcgtt ggctacccgt gatattgctg aagagcttgg  13080
cggcgaatgg gctgaccgct tcctcgtgct ttacggtatc gccgctcccg attcgcagcg  13140
catcgccttc tatcgccttc ttgacgagtt cttctgagcg ggactctggg gttcgaaatg  13200
accgaccaag cgacgcccaa cctgccatca cgagatttcg attccaccgc cgccttctat  13260
gaaaggttgg gcttcggaat cgttttccgg gacgccggct ggatgatcct ccagcgcggg  13320
gatctcatgc tggagttctt cgcccacccc aacttgttta ttgcagctta taatggttac  13380
aaataaagca atagcatcac aaatttcaca aataaagcat ttttttcact gcattctagt  13440
tgtggtttgt ccaaactcat caatgtatct tatcatgtct gtataccgtc gacctctagc  13500
tagagcttgg cgtaatcatg gtcatagctg tttcctgtgt gaaattgtta tccgctcaca  13560
attccacaca acatacgagc cggaagcata aagtgtaaag cctggggtgc ctaatgagtg  13620
agctaactca cattaattgc gttgcgctca ctgcccgctt tccagtcggg aaacctgtcg  13680
tgccagctgc attaatgaat cggccaacgc gcggggagag gcggtttgcg tattgggcgc  13740
tcttccgctt cctcgctcac tgactcgctg cgctcggtcg ttcggctgcg gcgagcggta  13800
tcagctcact caaaggcggt aatacggtta tccacagaat caggggataa cgcaggaaag  13860
aacatgtgag caaaaggcca gcaaaaggcc aggaaccgta aaaaggccgc gttgctggcg  13920
tttttccata ggctccgccc ccctgacgag catcacaaaa atcgacgctc aagtcagagg  13980
tggcgaaacc cgacaggact ataaagatac caggcgtttc cccctggaag ctccctcgtg  14040
cgctctcctg ttccgaccct gccgcttacc ggatacctgt ccgcctttct cccttcggga  14100
agcgtggcgc tttctcatag ctcacgctgt aggtatctca gttcggtgta ggtcgttcgc  14160
tccaagctgg gctgtgtgca cgaacccccc gttcagcccg accgctgcgc cttatccggt  14220
aactatcgtc ttgagtccaa cccggtaaga cacgacttat cgccactggc agcagccact  14280
ggtaacagga ttagcagagc gaggtatgta ggcggtgcta cagagttctt gaagtggtgg  14340
cctaactacg gctacactag aagaacagta tttggtatct gcgctctgct gaagccagtt  14400
accttcggaa aaagagttgg tagctcttga tccggcaaac aaaccaccgc tggtagcggt  14460
ggtttttttg tttgcaagca gcagattacg cgcagaaaaa aaggatctca agaagatcct  14520
ttgatctttt ctacggggtc tgacgctcag tggaacgaaa actcacgtta agggattttg  14580
gtcatgagat tatcaaaaag gatcttcacc tagatccttt taaattaaaa atgaagtttt  14640
aaatcaatct aaagtatata tgagtaaact tggtctgaca gttaccaatg cttaatcagt  14700
gaggcaccta tctcagcgat ctgtctattt cgttcatcca tagttgcctg actccccgtc  14760
gtgtagataa ctacgatacg ggagggctta ccatctggcc ccagtgctgc aatgataccg  14820
cgagacccac gctcaccggc tccagattta tcagcaataa accagccagc cggaagggcc  14880
gagcgcagaa gtggtcctgc aactttatcc gcctccatcc agtctattaa ttgttgccgg  14940
gaagctagag taagtagttc gccagttaat agtttgcgca acgttgttgc cattgctaca  15000
ggcatcgtgg tgtcacgctc gtcgtttggt atggcttcat tcagctccgg ttcccaacga  15060
tcaaggcgag ttacatgatc ccccatgttg tgcaaaaaag cggttagctc cttcggtcct  15120
ccgatcgttg tcagaagtaa gttggccgca gtgttatcac tcatggttat ggcagcactg  15180
cataattctc ttactgtcat gccatccgta agatgctttt ctgtgactgg tgagtactca  15240
accaagtcat tctgagaata gtgtatgcgg cgaccgagtt gctcttgccc ggcgtcaata  15300
cgggataata ccgcgccaca tagcagaact ttaaaagtgc tcatcattgg aaaacgttct  15360
```

-continued tcggggcgaa aactctcaag gatcttaccg ctgttgagat ccagttcgat gtaacccact 15420
cgtgcaccca actgatcttc agcatctttt actttcacca gcgtttctgg gtgagcaaaa 15480
acaggaaggc aaaatgccgc aaaaaaggga ataagggcga cacggaaatg ttgaatactc 15540
atactcttcc tttttcaata ttattgaagc atttatcagg gttattgtct catgagcgga 15600
tacatatttg aatgtattta gaaaaataaa caaatagggg ttccgcgcac atttccccga 15660
aaagtgccac ctgacgtc 15678

<210> SEQ ID NO 21
<211> LENGTH: 10156
<212> TYPE: RNA
<213> ORGANISM: Artificial Sequence
<220> FEATURE:
<223> OTHER INFORMATION: negative-sense vector RNA genome

<400> SEQUENCE: 21
acgcuuaaca aauaaaacaac aaaaaugaga aaaacaauca aacaaccaaa gguucagauu 60
uaggaucuug uuuuuuucaa gauacaucac acaagagucu uagcaugggc aggcuuccag 120
gaguauccgg uucacaggca acuguagucu aguagggaug aucuagaucu gauauccucu 180
agggugaucc accuguugua ccuaugaagg ugucuuucca cuucucugga uagauccuug 240
augcugccaa cgagucuggu agucuucacu aucuuguaaa ucaaccugau ccagugagau 300
gacagacuca ggcuagaauu acaggcuacc cuuuugaaca cugagguguc guuggaccaa 360
cuccaagaua gauaaacguu cccucgaaug acuugcuuuc ugaaguaaua aguuauaggu 420
cuguuauaca ggucgugaag ucuugcgaag cuagggacgu caccuaaagc aguagauaga 480
uacaucauag uacugcaaca uauguugaag ugccucagga uuuugggauc agacggugga 540
uagaacgagg ggucaguuag ggguuuggaa acguugaaga cucuguugga gaaaacuauc 600
augauggcua uaaugauagc cacuuuagac agaguucccc ucuguaacuc aagaucauca 660
accaucuugu ggacuagaaa agauucuaca ucacugucaa ucagaguuau gaucaucuca 720
uuguaaggau uugauaugau uucuucagga aauccucuca caagauccug auaguucaag 780
gaacgagcuc ucugcaucuc acucuugggg cugcuacaau ugaauaacac aaggcucauu 840
ucucgaaggg uggaagaggu caaguacuca gcaucucuga aaaacuuccc ucguuuggag 900
aaucggaggu agagcucaga ugaaaaagac gaaguuacuu gggugauaaa cccugugacc 960
gaggggaacg cucuugacag guguugaaua gccuuguagu uuggauuuac uagcauaguc 1020
ccauaaguuu ugaagaccaa auagaguggu ccaucuauag acaaugcaaa aucggacauu 1080
aacaggguga uccgguugau agaugcaaug ucaguaacuu cugcaucgca aauaaugagg 1140
ucauaggaca uguugaccug cuuuuggacu gacuggaagu auuuccaggu ugccaaguuu 1200
cucaagucgg acgguuuuuc ccagauugag ucaagaucua ucacucugga gacgauauca 1260
uuuccucccc ucaugauugc ugaaggaggc aguggaugug uuccggaagc caucagguca 1320
uucaccucua aaagacuguu gaacacaagc uuggcaucug gaaacauguu gaggacugcc 1380
cuugauaucc ccccugaccc guccccaacu acaaggcaga gagaugggaa aacauugaga 1440
ucaucuagaa uaggcuuaag cuuauaauga gcaccgguug cccacugaac cacucucaag 1500
cccgagauca aaggguucug gaaccucuua gagagggccc uuaugucaag cuccgagaca 1560
ggggccgggu uugcugaggu agagacugca accuguugag cagagcagac ccauucugaa 1620
cauccuaccu uacgggacac cuucuuguug gggcuguaau cuccagucau gguucuagcu 1680
gcauggcgca ccucuugauc cacccaucuu guccuucgua aagagucuuu uagcagucgu 1740

-continued

```
ugaauguugu cgucugacuc uaagguaucu ucuccgugcc cgcccagcac cugccucauc   1800
aaagaacuca auugucgcag guuaucucuc auacucuuag auagguuucu cucaacccuc   1860
uggaguagaa gaugagacug guaaguaaug agggauaggu acgucauuuu ggcacuucua   1920
aagucugaaa agauccauag ccagucauuc ucuggagacg ccgugauuau cucucgcuca   1980
uagcguagca cauguuggag auaacacaag auugaucugu ugccuucuuu cauagugguu   2040
ggauaagcgg cggggauuuu cugagggaua gaaaauaucu cuccucuaag agacgguucu   2100
cugagcauua uguacaagga gggaugguua ucuagccuca ggagaauaua ugagauuacc   2160
ccugagacca auucaagagg ucuauuaaua uugauauuug ucauucuugu caagaagcaa   2220
aucgaggauc cuaucaauac uccccuugcg agcccucuca aauagucucu aggggaaacc   2280
uugccguaua uguugacagg gaagaugguu ccaucauugu auccugaguc gugaauugcc   2340
acuaagauug aguauaagag ccccugagcu gauccgauau ggugagacuu uucucuaccg   2400
cuuagagauu caaaaucucc uggucucaga cggauaucgg gaagccucug gaagugaggc   2460
acagccccag aaaccauucu ggauauucuu uucgacacau ccggaaacuc gaagaucuga   2520
gaggucucca gggucacguc gucaaugggu cucacacacc uguugcaucg gaggugccaa   2580
ugaaacguag agucucuuag ccuugugucu cucuguacca gcucugaugu ccaugucugu   2640
gcauaaagca ucaauggcug gaacaugaaa ucguaguucu ucccgucuug ggucaaauca   2700
gacauggugu cuguacuaac agaaauauga gagaggaggu ucgggcagac agaagaauac   2760
ccuccuucgc uguaucuggc agacuugaac cuaugcaagg cugaccccgu ccuuuugaag   2820
acaggggccu ccucuagagg gaaaucaggg ccugucagag acauaauguu ccuaauuaga   2880
gcuugagcca aguuggaauc ucuaguaaug aaccaguuua uagauucuuu uaacgauaga   2940
gcucucuuca ccacaugaac auuagugacu uuuucccaug cauggaauag cugggucgac   3000
auagaggugg acgagcccaa guaucccuuu agggggccuc gugaaaaaaa ugacugauca   3060
aaggacggga guacugauac agaaacucua ggauugccuc cuccuguugc uccacaagug   3120
caagaaauag aggacuuggg aaguaauccc aacaucucag aagggugagg aacugucgug   3180
ccuaccacuu uucuucccca agagaucucc cuaaguagau cugcccucuc ugaagagcaa   3240
ggccacaccc ccccaacccu cugaggugucc ugggucaucc gacuaauccc guggaucucu   3300
gaguuguaga aggauucuuc uaaaguuuuu gagagacucu uucuaaacug ccuucuuauc   3360
guucgggagu uuuguaucaa uccaaugauu gacucgggga uucccaaaaa agacgaacug   3420
aauagcucac ugagaaaucg aggaaacaga ggcucaacag auauuaagaa gaguauaaaa   3480
uuaucucuau gggucuugga caacaggauu gccucucgaa acucugaauu uuccaccuug   3540
uccaccucgu cauauaaagc cuuucugauu gcauccuuga guagaauggu aggacuggcc   3600
ccuccucuga uauuuaaggu ggucggaucu ucuagaaggc gagugaagcu cucgaguguu   3660
cucucuccaa gaucuggguu uccagccucu ugacacaacg cgugaaucca ggacucuugg   3720
gagcuuaacc agaucucucu ccagaaggau aacccuucag agacagggucc ugagaacugu   3780
cguauaugga aucuuccgag ggacauucca gauaucccuc ccaaagaagg aucuagauag   3840
auuauccuug acauggcuag gagaaagcuc uccccuucag cgcucagaau cuuguaaacu   3900
cuucccuuua agauugggcu aaauagcagg uagugaaaga cugccuguac ugacaugagc   3960
agaaaauccc ucaucgguuu gaucaaagau ugagaguguu gugccacugu uagcgcauug   4020
guggacacug ucgacauuau auuggcgagg uugacuauuu ggucauuaga gacgcaagag   4080
```

-continued

```
acucuggccc aucuuuugga cucaggcacc aauauguuac cucuaaacaa aggggguuuu   4140

ccauagauga ggaagucaua acuacacaug gucucuucuu ucuugaugau cagcccuagc   4200

uuagaugccc cuuccucgac ggcucuguau aucgaaagug cauuccuuga uauucucucc   4260

aauucauaga ggagccccuc uugagauagc ccuggcgaca acauguaugu cggacauaaa   4320

accugguugu cuccuugagc uaguauuuug guucuugugu uccugauuug agauucucua   4380

ucuaucauca auaagcugac uagacuccag cccuucugcc guaagccuuc uagcccgcca   4440

uccuggccau uccaacaggu ugggccguug gacgcaucua agcaguauau uugauccucc   4500

cguaacccga ugaggucuga ucugucugaa uaauagaucc aggccuuuug aaaaaacucg   4560

uguguucuag aaaacacucu cuucaaucca aacacuugau cuaggacaga aaauacaucc   4620

ucuguugacu cuaaucuuug augguuguuc cacuuuucau aguccaggug aaaugcauau   4680

gugacccuug aauaguccaa aagcccuugc ccggugaccc ugucgaucag cuuuuuaaac   4740

accuuguuca gguugucugu cauagucagc gcgucaaaaa guggcaagau guaguuggcc   4800

aagaguuuuu cagugaugac aaaauacaau cuuagauucc augacauuag agcaaagaau   4860

cgaccuucaa ucuucaauuc ccguuccuuu ggcuugaggc caauuaucaa gucuucaucu   4920

ggcaauccuc cgaggucuau agaccucaga aacucucggg gauugacagg cggcuuagac   4980

agggccguga uaauaacuuu uucgcuagga acaggccccc cucgguuuuc ugacagccaa   5040

gaagcuaguc ucguucuggu gaaagaaugu gauuugucau ccaauauuuc ugacggaucc   5100

auugauucag gaaucucaaa gaucugcgug aucgggagcu ugugccaugu aucccccacc   5160

aagucuacaa uauguuuggg uggccauguu uggguuuuga uauaaggagu caaggggugg   5220

ucucgggcua ggaaucuuga auccagauac cacuuggagu acuuaucaaa accccaucua   5280

aggauccucc uggcuagguc gcuugcuaag cacuccuggu aggacuuauc uaucauuuuu   5340

uuaaggugaa ccugaucaua uaguuuugac agacccuuuc gauaaucuau auaugggugc   5400

ccccaaugcc uguaacagcc aaacacaaaa accaagucau guauguuguc gaauugaucc   5460

agagcccuaa agaaccuucu ugcacaggga ccgaacgucu cuucaaguug acuuaccuug   5520

ucuuuuauaa auacaggaaa gucucccaag gaaugaauga gaggccuaaa cuuuucugcu   5580

cucuggacua aacuauucac gacauauggc uccaauauuu ugaugacuuc auagccggag   5640

uuuccacaca uagacaagac uugaucccca gcaauguaca gcuggcauag uugagauauc   5700

aagucaucug aguaucgggg cucuggggga gagagcaaga ccauuaagga guugaagcga   5760

gacaagaaaa gaucuuuuag cauaagugug uaguuucugu caaaaagaca auuggaacuu   5820

ugggaguaaa caaaguccuu ugucacgauc agcagucccc auauuugguc uuugaacuuu   5880

accaaguccu ucccgauguc cacugagguu aaaucuuucc auaaaugcuag gauggucuuu   5940

ucuucauccc agucuagggc guucauguau aaggugauua cauggaagaa caaguaagag   6000

gaauacgugu uggcaagaua ccuuccaaau gcauuaucau aaucaacccu cucaaggcaa   6060

cuuaacacuc ccucuggggg gauucucagc ccucuauuuc cuagcgugag auucaacagc   6120

uucucuaugg gggacgacuu ggaauagaaa ugggccaagu cuguuauaca ucuccggcuc   6180

cuguuggauu cagagugggc accauauaac cagagagaaa ucauugacug ugcagccauu   6240

ccgcccaccu ugagagaacc caaaucuacc uucuugaaau aaucuuucaa aacucugaaa   6300

gaccuggagc aauugucugu uagagucauc cgauaagguc uauucccugu uuuuaaccau   6360

ucuaacauua gucuagcagg aucuucuauc aaaggagagu ugagauugua gucagaguuc   6420

cucaagaugu uggggacaau ggggguuccu cuggguucag ccucuaacuc gauuggguca   6480
```

-continued

```
auagggucau cauagaccuc uccaggaucg agcaucuuga aguaagucuc agguugagaa   6540
aguguugcca guuguucuuc ugaucuaaug uuuuuuucuc gacugaaaag cuaccgcggg   6600
uaggcgcgcc guauuaauua aggaggggug uuaguuuuuu ucaugcuagc guagcccggg   6660
cguagcggcc gcguaccugc agguccuuug agggauguua auaguuuuuu ucacauccaa   6720
gaggaucaaa auguaaaggu aaucaacuug acuuugauga aaugcagcgg uuuaauggca   6780
ccauaacaug uuuuuuguua uauugcuccc aaggguugga guugagccca uauguucucu   6840
ccuccagagg uaaacaagug auaaauuugc gggauauaau cugacguacg uuauucuaga   6900
agcagagagg aaucuuuguc cucuucggac cuuugugucu gaagagacau gucagaccau   6960
aguugacaug cucucggguu cauguugaua caccagacuc ugcccuggau augacacugu   7020
uuugcaauca cucuuauuug caauccgacg aacucaguau caucauccca agugaucucc   7080
ugagaguauu ccaacuccuc cccuucaaga gggccccugg aaucagccca cuggaagaua   7140
aagguucucc ucaauuugua uacccaguuc aggcccucag ggacuggaga uccugacaaa   7200
gccaguccaa uaaccacuuu gacuaacccg aucauccuau gauucccaga auauaucucg   7260
ucgaaugauu ucagaaugug ccgcaggauc cugaacgagu aaccauucgg gcuacacacu   7320
uuaacccuuc cguugauaca aaaguuccuc auguucuucu ugccuguaag uucuuucagc   7380
gggacguauu caggggggugg aagccacaag ucaucgucau ccagaggggc ugacgcggga   7440
gaggauuuuu gaguguccuc gucccugcgg uuuuucacua ucuuacguag gagguucauc   7500
gauuuaucag ugguguugcc uguuuuuuuc auguugacuu ugggacaucu cggauuuuau   7560
ugucuagagg gacugagggg agagguucgg uuagcaagau guauagcgau ucaagucauc   7620
uugcaugauu uuacucagcu ugucggauuc gacuaacaac uggaauuucu uagaguuggc   7680
caaagcgacc caucccagua cacaucuuag ggggaguuug gacccgucau gggcuaaacg   7740
ggucacaccu gguacauuuu uugccucuuu aacuauauca ucaagguuca uuuucaauug   7800
cucaaaauua uacaagagua ucccugagga ucgagaggga aacuuauauu uuuuggagaa   7860
acuuucugca aucuggugag cgaucucagc cuccacugau agaucauccu cuucauuggu   7920
agccgaccau ucaagggcug gagggccaga agcaauuuga gccgccaucc uggcuuucga   7980
ugauuggcuu ucucucugag aaggaguggg uguugucucc uucuugagcu cucggccagu   8040
agucuggguu gauuuauccu cugaagacuu uccuggaggg uugggaaagu ugaccgcgac   8100
auaggauaua aucucuucua cggucuguga ccauaucuug agaaaucucu cuccugaccu   8160
cauuugucug acuauuugga cuccaacauu uuccagguau gacuggaaca ggaagcuagg   8220
auccucuccu ucauccaucu gaaaguccuc ucgauacuug ccuucuccca ccuuggcuau   8280
cucaccaugg uugggcgauu uuccaucauc caggugaagu cgccccauau ccucagggag   8340
auuguccacc ucuaugguu ccccuuggag augagccuga uugucuucga uauuucuauu   8400
gaucagauca acaguuucuu cagccaucuc aagaucggcc agaccggcuc uaauagcacu   8460
aggauugaca aagaucuugc ucauguuugg gaugguucga aaggaggggu guuaguuuuu   8520
uucaugaugg auauacacaa uccguagauu uccggcauuu uguuauucaa cuucuuacac   8580
auugauccua gcagaagcac aggcugcagg gugacggucc aucccgcucu ccugggcaca   8640
agacaugggc agcgugccau cauccugcuc cuccaccucc ggcgggaagc cauggcuacc   8700
ggaucccgau uggaaguaga gguucucucc ggaaccugag ucacucgaau augucuuguu   8760
uagaaacucg gcgaaugagu uuggacgggc uugaugauug gaacugacug agacauaucu   8820
```

-continued

```
ccguauguga gaucucuuua gucgaccucc auucaucaug auucgaguau aaacagccuc   8880
cggacuucug guuucaccug aaaaguaguc cucgucguca gaguugacag uuccaucauc   8940
ugccagugcu acgucagucu uugucaguuc agccgccucg uauucuugaa guucuuucuc   9000
aucucugaag aaucuucuuu caaaugucce uuucccgaag aauuccucuc ccagauagcc   9060
cccuagaaca gacauuucau gaggagcaca ugcagcaaua accguugcau uuagggaucu   9120
gacuugaccc auauagcauc cuacaaagug aaugagauug aacacgugac caacagcauu   9180
ugaugaauaa ggagauuucc cacucaagcc uagugaacgg aaguggauga aauaagagug   9240
aggaacagcu gucuccugcc cuggcucaaa cauucuucuu aucucuuccu caaaguucuu   9300
guggaagaaa uauaguauug ccucucuagc ggugagauug auuuguuuua ugaacccagu   9360
aaaugauacc aguccugaac agucuucaua agcagugaca acugugccca cucugauugc   9420
ugaauauaga ugcucaaucc gggagaaaaa caugucauag guuccggcca aaaaucugaa   9480
guuugguaua guacuccaau uagcacacau uuugugaguu gucauuagag uaugguguuc   9540
cacgauuuua acaaaagggg cugucucaaa aaucugcucu auccugucug caauguuugu   9600
cuuauaguua ccaguguuuu gcccggauau uuugcucaac cuauacagac ucaagagaag   9660
accgacuaag gacgcaugcu cagggacagu ggggucucuu gucaguucca ugccuccugu   9720
cagagcccaa uucccuucua caucaguacg uuuuaucucc accagagaac cuggggugau   9780
cuuaucuccu uuucgugcaa ucacaauucc auagcugguc cagucuuccg gacaugucce   9840
cucaaaaaac ugcauugccg cugccaaaua ggaacauaca ucgucaggau uaaguuuggc   9900
ggcgcucaug ccugacaaaa cugacuugua ugcuuuauuu aaaucgggag ccuuuccuag   9960
gguuauacag ggcuuuuuca aaucuuugau ggcaggguac uuguacucau auugauccac  10020
gauaaucuca ggcuucaaag agaccaccug auuauugacu uugaauacaa ucuugucggc  10080
auccauugua ggggguguuac auuuuugcuu ugcaauugac aaugucuguu uuuucuuuga  10140
ucugguuguu aagcgu                                                   10156
```